United States Patent [19]
De Mesmaeker et al.

[11] Patent Number: 5,602,240
[45] Date of Patent: Feb. 11, 1997

[54] BACKBONE MODIFIED OLIGONUCLEOTIDE ANALOGS

[75] Inventors: Alain De Mesmaeker, Kaenerkinden, Switzerland; Jacques Lebreton, Marseilles, France; Adrian Waldner, Allschwil, Switzerland; Phillip D. Cook, Carlsbad, Calif.

[73] Assignees: Ciba Geigy AG., Basel, Switzerland; Isis Pharmaceuticals, Inc., Carlsbad, Calif.

[21] Appl. No.: 140,206

[22] PCT Filed: May 21, 1992

[86] PCT No.: PCT/US92/04305

§ 371 Date: Apr. 25, 1994

§ 102(e) Date: Apr. 25, 1994

[87] PCT Pub. No.: WO92/20823

PCT Pub. Date: Nov. 26, 1992

Related U.S. Application Data

[63] Continuation-in-part of Ser. No. 703,619, May 21, 1991, Pat. No. 5,378,825, which is a continuation-in-part of Ser. No. 566,836, Aug. 13, 1990, Pat. No. 5,223,618, and a continuation-in-part of Ser. No. 558,663, Jul. 27, 1990, Pat. No. 5,138,045.

[51] Int. Cl.$^6$ ............................. C07H 21/00; C12N 15/11
[52] U.S. Cl. ...................... 536/22.1; 536/23.1; 536/25.3; 536/25.34; 536/25.5; 536/25.6; 514/44
[58] Field of Search ...................... 536/22.1, 25.34, 536/25.3, 23.1, 25.5, 25.6; 514/44

[56] References Cited

U.S. PATENT DOCUMENTS

| | | | |
|---|---|---|---|
| 3,687,808 | 8/1972 | Merigan et al. | 195/28 |
| 4,469,863 | 9/1984 | Tsó et al. | 536/27 |
| 4,591,614 | 5/1986 | Miller et al. | 525/54.11 |
| 5,113,005 | 5/1992 | Celebuski et al. | 556/449 |
| 5,138,045 | 8/1992 | Cook et al. | 536/27 |
| 5,223,618 | 6/1993 | Cook et al. | 544/276 |
| 5,378,825 | 1/1995 | Cook et al. | 536/25.34 |
| 5,386,023 | 1/1995 | Sanghvi et al. | 536/25.3 |

FOREIGN PATENT DOCUMENTS

| | | |
|---|---|---|
| WO89/11486 | 11/1989 | WIPO . |
| WO89/12060 | 12/1989 | WIPO . |
| WO92/02534 | 2/1992 | WIPO . |
| WO92/03568 | 3/1992 | WIPO . |
| WO92/05186 | 4/1992 | WIPO . |
| WO93/18052 | 9/1993 | WIPO . |

OTHER PUBLICATIONS

Abdel-Magid et al., "Reductive Amination of Aldehydes and Ketones by Using Sodium Triacetoxyborohydride", *Tetra. Lts.* 1990 31: 5595-5598.

Alul et al., "Oxalyl-CPG: a labile support for synthesis of sensitive oligonucleotide derivatives," *Nucleic Acids Research*, 1991 19, 1527-1532.

Atkinson, T. et al., "Solid-phase Synthesis of Oligodeoxyribonucleotides by the Phosphite-triester Method" *Oligonucleotide Synthesis. A Practical Approach*, Chapter 3. M. J. Gait, Ed., IRL Press, Washington, DC 1985 pp. 49-81.

Balgobin et al., "Solid Phase Synthesis of DNA Under a Non-Depurinative Condition With a Base Labile 5'- Protecting Group (Fmoc) using Phosphiteamidite Approach," *Nucleosides and Nucleotides* 1987 6, 461-463.

Bankston et al., "A Short Synthesis of 5'-Tritryl- Protected threo- and erythro- 3'-Cyano-3'-doexythymidine Epimers Using Free-Radical Chemistry," *J. Het. Chem.*, 1992 29, 1405-1407.

Barton et al., "A 'One-Pot' Synthesis of Sulfenamides," *J. Org. Chem.*, 1991 56, 6702-6704.

Barton et al., "Stereoselectivity in Radical Reactions of 2'-Deoxynucleosides. A Synthesis of an Isostere of 3'-Azido-3'-Deoxythymidine-5'-Monophosphate," *Tetrahedron Letters*, 1989 30, 4969-4972.

Baud et al, "Improved Procedure for the Regiospecific Synthesis of 2'-Deoxyribonucleosides," *Tetrahedron Letters*, 1990 31, 4437-4440.

Beaucage, Serge L., Iyer, R., et al., "3H- 1,2- benzodithiole-3-one 1,1-dioxide as an improved sulfurizing reagent in the solid-phase synthesis of oligodeoxribonucleoside phosphorothiioates", *J. Am. Chem. Soc.* 1990, 112, 1253-1254.

Beaucage et al., "Advances in the Synthesis of Oligonucleotides by the Phosphoramidite Approach," *Tetrahedron*, 1992 48, 2223-2311.

Bellon et al., "4'-Thio-oligo-β-D-ribonucleotides: synthesis of β-4'-thio-oligouridylates, nuclease resistance, base pairing properties, and interaction with HIV-1 reverse transcriptase," *Nucleic Acids Res.*, 1993 21, 1587-1593.

Froelich et al., "An Improved Synthesis of 3'-Keto-5'-O-Tritylthymidine", *Nucleosides & Nucleosides* 1989 8(8), 1529-1535.

Biggadike, K. et al., "Short Convergent Route to Homochiral Carbocyclic 2'-Deoxynucleosides and Carbocyclic Ribonucleosides" *J. Chem. Society Chemical Communication* 1987 1083-1084.

Bodenteich et al., "Synthesis of Enantiomerically Pure Carbocyclic 3'-Azido-2',3'-Dideoxythymidine, A Potential Anti-Aids Drug," *Tetrahedron Letters*, 1987 28, 5311-5312.

Brown et al., "Modern machine-aided methods of oligodeoxyrobonucleotide systhesis" in *Oligonucleotides and Analogues: A Practical Approach*, Chapter 1, Eckstein, F., ed., IRL Press, Oxford, pp. 1-24 (1991).

(List continued on next page.)

*Primary Examiner*—James O. Wilson
*Attorney, Agent, or Firm*—Woodcock Washburn Kurtz Mackiewicz & Norris

[57] ABSTRACT

Oligonucleotide analogs are provided wherein phosphodiester inter-sugar linkages are replaced with four atom linking groups. Such linking groups include NR—C(O)—CH$_2$—CH$_2$, NR—C(S)—CH$_2$—CH$_2$, CH$_2$—NR—C(O)—CH$_2$, CH$_2$—NR—C(S)—CH$_2$, CH$_2$—CH$_2$—NR—C(O)—R—CH$_2$, and CH$_2$—C(S)—NR—CH$_2$. Methods for preparing and using these oligonucleotide analogs are also provided.

20 Claims, 2 Drawing Sheets

OTHER PUBLICATIONS

Camarasa et al., "Aldol Reaction of Nucleoside 5'- Carboxaldehydes with Acetone, Synthesis of 5'-C-Chain Extended Thymidine Derivatives," *Nucleosides and Nucleotides,* 1990 9, 533-546.

Ceruzzi et al., "The Intracellular and Extracellular Fate of Oligodeoxyribonucleotides in Tissue Culture Systems", *Nucleosides & Nucleotides* 1989 8, 815-818.

Cohen, J.S., Oligodeoxynucleotides, "Antisense Inhibitors of Gene Expression" CRC Press, Inc. Boca Raton FL (1989) (1-255, especially pp. 53-78; 79-80).

Cormier et al., "Synthesis of Hexanucleotide Analogues Containing Diisopropylsilyl Internucleotide Linkages" *Nucleic Acids Res.* 1988, 16, 4583-4594.

Cosstick et al., "Synthesis and properties of dithymidine phosphate analogues containing 3'- thiothymidine," *Nucleic Acids Res.,* 1990 18, 829-835.

Coull et al., "Synthesis and Characterization of a Carbamate-Linked Oligonucleoside", *Tetra. Ltrs.* 1987 28, 745-748.

Curran, "Radical Addition Reactions," in *Comprehensive Organic Synthesis,* Trost, B. M. and Fleming, I., Eds., Pergamon Press, Oxford, Vol. 4, pp. 715-831, 1991.

Damha et al., "An improved procedure for derivatization of controlled-pore glass beads for solid-phase oligonucleotide synthesis," *Nucleic Acids Research,* 1990 18 3813-3821.

Debart, F. et al., "Intermolecular Radical C—C Bond Formation: Synthesis of a Novel Dinucleoside Linker for Nonanionic Antisense Oligonucleosides", *Tetrahedron Letters* 33 1992, 2645-2648.

Egholm et al., "Peptide Nucleic Acids (PNA). Oligonucleotide Analogues with an Achiral Peptide Backbone," *J. Am. Chem. Soc.,* 1992 114, 1895-1897.

Egholm et al., "Recognition of Guanine and Adenine in DNA by Cytosine and Thymine Containing Peptide Nucleic Acids (PNA)" *J. Am. Chem. Soc.* 1992 114, 9677-9678.

Etzold et al., "The Extension of the Sugar Chain of Thymidine: a New Route to 5'-Deoxyhexose Nucleosides," J.C.S. *Chem. Comm.* 1968 422.

Fiandor et al., "Synthesis of 3'-deoxy-3'-(2- propynyl)thymidine and 3'-cyanamethyl-3'deoxythymidine, analogs of AZT," *Tet. Lett.,* 1990 31.

Fikes et al., "Preassociating α-Nucleophiles," *J. Am. Chem. Soc.,* 1992 114, 1493-1496.

Fleet, et al., "Methyl 5-0-Tert-Butyldiphenylsilyl-2-Deoxy-α beta)-D-Threo-Pentofuranoside as a Divergent Intermediate for the Synthesis of 3'-Substituted-2',3'-Dideoxynucleosides: Synthesis of 3'-Azido-3'- Deoxythymidine, 3'-Deoxy-3'-Fluorothymidine and 3'- Cyano-3'-Deoxythymidine", *Tetrahedron* 1988 44, 625-636.

Gait, M. J. et al., "Synthetic Analogues of Polynucleotides. Part XII. Synthesis of Thymidine Derivatives Containing an Oxyacetamido- or and Oxyformamido-Linkage Instead of a Phosphodiester Group", J. C. S Perkins I 1974 1684-1686.

Giannis et al., "Fragmentation and Witrig Olefination of Glucosamine Derivatives-A Simple Route to Open Chain Amino Sugars and Chiral Glyerols," *Tetrahedron,* 1988 44, 7177-7180.

Goodchild, "Conjugates of Oligonucleotides and Modified Oligonucleotides: A Review of Their Synthesis and Properties", *Bioconjuage Chemistry* 1990 1, 165-187.

Greene et al., "Protection for the Carbonyl Group" in Protective Groups in *Organic Synthesis,* Chapter 4, John Wiley & Sons, Inc., 1991, pp. 175-223.

Halford et al., "Synthetic Analogues of Polynucleotides" *Nature* 1968 217 638-640.

Hanamoto et al., "$SmI_2$-Promoted Ketyl Radical Addition to O-Benzyl Formaldoxime. A New Aminomethylation," *Tet. Letts.* 1991 32, 3555-3556.

Hart et al., "Bis(trimethylstannyl)benzopinacolate- Mediated Intermolecular Free-Radical Carbon-Carbon Bond-Forming Reactions: A New One-Carbon Homologation," *J. Am. Chem. Soc.,* 1988 110 1631-1633.

Hill et al., "3,4-Dihydro-2H-1,4-benzoxazines," *J. Chem. Soc.,* 1964 716, 3709-3713.

Hillgartner et al., "Bis(trimethylzinn)benzpinakolat, seine reversible radikalische Dissoziation und Reaktmonen," *Liebigs. Ann. Chem.* 1975 586-599.

Horwitz et al., "Nucleosides. V. The Nonomesylates of 1-(2'-Deoxy-β-D-lynofuranosyl) thymine," *J. Org. Chem.,* 1964 29, 2076-2078.

Hronowski et al., "Synthesis of New Carbocyclic Analogues of 3'-Azido-and 3'-Amino-2', 3'- dideoxynucleosides," *J. Chem. Soc., Chem. Commun.,* 1990 1547-1548.

Huang et al., "Building Blocks for Oligonucleotide Analogues with Dimethylene Sulfide, Sulfoxide, and Sulfone Groups Replacing Phosphodiester Linkages" *J. Org. Chem.* , 1991 56, 3869-3882.

Huang et al., "Non-Ionic Antisense Oligonucleotides containing sulfide and Sulfone Linkages in Place of Phosphodiester Groups in Natural Oligonucleotides" *J. of Cellular Biochemistry,* Abstracts, 20th Annual Meeting, CD209.

Hyrup et al., "Modification of the Binding Affinity of Peptide Nucleic Acids (PNA). PNA with Extended Backbones consisting of 2- Aminoethyl-β-alanine or 3-Aminopropylglycine Units," *J. Chem. Soc. Chem. Comm.,* 1993 518-519.

Inouye et al., "Selective Coloration of Spiro Pyridopyrans for Guanosine Derivatives," *J. Am. Chem. Soc.,* 1992 114, 778-780.

Jenkins et al., "9- (2-Methyl-β-D-ribofuranosyl)adenine (2'-Methyladenosine)," *Synthetic Procedures in Nucleic Acid Chemistry,* (vol. 1) 149-153.

Medich, J. R., et al., "Synthesis of the Carbocyclic Nuceloside (-)-Neplanocin A" *Tetrahedron Letters.* 1987 28, 4131-4134.

Jones, M. F. et al., "Synthesis of Carbocyclic Nucleosides: Preparation of (-)-5'-Homoaristeromycin and Analogues," *J. Chem. Soc. Perkin Trans. I,* 1988.

Jones, G. H. et al., "The Synthesis of 6'- Deoxyhomonucleoside- 6'-phosphonic Acids" *Journal of the American Chemical Society* 1968 90 5337-5338.

Jones, R. A., "Preparation of Protected Deoxyribonucleosides" in *Oligonucleotide Synthesis A Practical Approach* Gait, ed. , Oxford: IRL Press, Chapter 2, 1984, pp. 23-34.

Kappler, F. et al., Nucleic Acid Chemistry: Improved and New Synthetic Procedures, Methods and Techniques, Part 4, Ed. L. B. Townsend and R. S. Tipson, Wiley-Interscience Publication, 1991, p. 240.

Kawai et al., "Single-Stranded DNA & RNA Binding: Backbone-Modified Polynucleotide Analogues", *Third Chemical Congress of North America, Organic Chemistry,* 1988, Canada, Jun. 5-10, 1988, Abstract No. ORGN 318.

Kirshenbaum, M. R. et. al., "Novel Oligonucleotide Analogues with a Sulfur-based Linkage" *The Fifth San Diego Conference: Nucleic Acids: New Frontiers,* Poster Abstract 28, Nov. 14-16, 1990.

Köster et al., "Diakyl aluminum chloride: A reagent for removal of trityl group from trityl ethers of deoxynucleosides, deoxynucleotides, and oligodeoxynucleotides," *Tetrahedron Letters.* 1982 23, 2641-2644.

Lemaitre et al., "Specific antiviral activity of a poly (L-lysine)-conjugated oligodeoxyribonucleotide sequence complementary to vesicular stomatitis virus N protein mRNA initiation site", *Proc. Natl.Acad. Sci. USA* 1987 84, 648-652.

Letsinger et al., "Cholesteryl-conjugated oligonucleotides: Synthesis, properties, and activity as inhibitors of replication of human immunodeficiency virus in cell culture", *Proc. Natl.Acad. Sci. USA* 1989 86: 6553-6556.

Li et al., "Synthesis and Characterization of Oligonucleotides Containing 4-O-Methylthymine," *Biochemistry* 1987 26, 1086-1093.

Lim et al., "Facile Synthesis of a New Orange-Red 7-amino-6-nitro-3,4-Dihydro-2H-1,4-Benzoxazine, *Book of Abstracts,* 203 *ACS national Meeting,* San Francisco, CA., Apr. 5-10, 1992.

Lin et al., "Synthesis and Biological Activity of Several Amino Analogues of Thymidine," *J. Med. Chem.,* 1978 21, 109-112.

Loke et al., "Delivery of c-myc Antisense Phosphorothioate Oligodeoxynucleotides to Hematopoietic Cells in Culture by Liposome Fusion: Specific Reduction in c-myc Protein Expression Correlates with Inhibition of Cell Growth and DNA Synthesis," Top. Microbiol. *Immunol.,* 1988 141, 282-289.

Loke et al., "Characterization of oligonucleotide transport into living cells", *Proc. Natl .Acad. Sci. USA 1989 86 374-3478.*

Ma, Y. et al., "The 9-Fluorenylmethyloxycarbonyl Group as a 5'-OH Protection in Oligonucleotide Synthesis," Biopolymers, 1989 28, 965-993.

Ma, M. et al., "Design and synthesis of RNA miniduplexes via a synthetic linker approach. 2. Generation of covalently closed, double-stranded cyclic HIV-1 TAR RNA analogs with high Tat-binding affinity," *Nucleic Acids Research,* 1993 21, 2585-2589.

March, J., "Aliphatic Nucleophilic Substitution" in *Advanced Organic Chemistry, Reactions, Mechanisms, and Structure,* Chapter 10, New York: John Wiley & Sons.

Marcus-Sekura et al., "Comparative inhibition of chloramphenicol acetyltransferase gene expression by antisense oligonucleotide analogues having alkyl phosphotriester, methylphosphonate and phosphorothioate linkages," *Nucleic Acids Research* 1987 15, 5749-5763.

Matsuda et al., "Synthesis and Biological Activities of 3'-Deoxy-3'-Isocyano,-Isothiocyano, and -Isoselenocyano-Thymidines," *Nucleoside & Nucleotides* 1990 9, 587-597.

Matteucci, "Deoxyoligonucleotide Analogs Based on Formacetal Linkages," *Tetrahedron Letters,* 1990 31, 2385-2388.

Matteucci et al., "Deoxyoligonucleotides Bearing Neutral Analogues of Phosphodiester Linkages Recognize Duplex DNA via Triple-Helix Formation" *J. Am. Chem. Soc.* 1991 113, 7767-7768.

Matthews, J. A. et al., "Review: Analytical Strategies for the Use of DNA Probes" *Anal. Biochem.* 1988 169: 1-25.

Mazur et al., "Isosteres of Natural Phosphates. 11. Synthesis of a Phosphonic Acid Analogue of an Oligonucleotide," *Tetrahedron,* 1984 40, 3949-3956 .

Mertes et al., "Synthesis of Carbonate Analogs of Dinucleosides. 3'-Thymidinyl 5'-Thymidinyl Carbonate, 3'-Thymidinyl 5'-(5-Fluoro-2'-deoxyuridinyl) Carbonate, and 3'-(5-Fluoro-2'-deoxyuridinyl) 5'-Thymidinyl Carbonate", *J. Med. Chem.* (1969) 12: 154-157.

Miller, P. S. et al., "Biochemical and Biological Effects of Nonionic Nucleic Acid Methylphosphonates", *Biochemistry* 1981 20, 1874-1880.

Miller, P. S., "Oligonucleoside Methylphosphonates as Antisense Reagents" *Biotechnology* 1991 9. 358-362.

Miller, P. S. et al., "Effects of a Trinucleotide Ethyl Phosphotriester, G'''p (Et) G'''p (Et) U, on Mammalian Cells in Culture," *Biochemistry* 1977 16 1988-1996.

Milligan et al., "Current Concepts in Antisense Drug Design" *J. Med. Chem.* 1993 36(14) 1923-1937.

Mirabelli et al., "In vitro and in vivo pharmacologic activities of antisense oligonucleotides", *Anti-Cancer Drug Design* 1991 6, 647-661.

Moffatt, J. G., et al., "Synthesis of Isosteric Phosphonate Analogs of Some Biologically Important Phosphodiesters" *Journal of American Chemical Society* 1970 92, 5510-5513.

Motawia et al., "A New Route to 2',3'-Dideoxycytidine," *Liebigs Ann. Chem.,* 1990 599-602.

Mungall, W. S. and Kaiser, J. K., "Carbamate Analogues of Oligoneotides" *J. Org. Chem.* 1977 42 703-706.

Musicki et al., "Synthesis of Carbohydrate Sulfonates and Sulfonate Esters" *J. of Organic Chemistry* 1990, 55, 4231-4233.

Musicki, "Synthesis of Nucleoside Sulfonates and Sulfones" *Tetrahedron Letters* 1991, 32, 1267-1270.

Nair et al., "Regiospecific 5'-Silylation of Nucleosides," *Org. Prep. Proc. Int.,* 1990 22. 57-61.

Nelson et al., "A New and Versatile Reagent for Incorporating Multiple Primary Aliphatic Amines into Synthetic Oligonucleotides" *Nucleic Acid Res.* 1989 17 7179-7186.

Nicolaou, K. C. et al., "A Mild and General Method for the Synthesis of 0-Glycosides" *J. Am. Chem. Soc.* 1983 105 2430-2434.

Nicolaou, K. C. et al., "Carbocyclic Thromboxane $A_2$," *J. Am. Chem. Soc.,* 1980 102 1404-1409.

Nielsen et al., "Sequence-Selective Recognition of DNA by Strand Displacement with a Thymine-Substituted Polyamide," *Science* 1991 254, 1497-1500.

Niitsu et al., "Synthesis of a Series of Linear Pentaamines with Three and Four Methylene Chain Intervals" *Chem. Pharm. Bull* 1986 34(3) 1031-1038.

Ogilvie et al., "Synthesis of a Thymidine Dinucleotide Analogue Containing an Internucleotide Silyl Linkage" *Tet. Letts.* 1985 26 4159-4162.

Overman et al., "tert-Butyldiphenylsilylamines: A useful protecting group for primary amines", *Tetrahedron Letters* 1986, 27(37), 4391-4394.

Parkes et al., "A Short Synthesis of 3'-Cyano-3'-Deoxythymidine" *Tetrahedron Letters* 1988 29 2995-2996.

Pauling, "Molecular Architecture and Biological Reactions," *Chem. Eng. News,* 1946 24, 1375-1377.

Perkins et al., "Accelerated Displacement of Duplex DNA Strands by a Synthetic Circular Oligodeoxynucleotide," *J. Chem. Soc. Chem. Comm.,* 1993 215-216.

Pfitzner et al., "The synthesis of nucleoside-5'aldehydes", *J. Am. Chem. Soc.* 1963 85 3027.

Pon, R.T., "Solid-Phase Supports in Oligonucleotide Synthesis," *Protocols for Oligonucleotides and Analogs,* Chapter 19, Agrawal, S., ed., New Jersey: Humana press, 1993.

Poopeiko et al., "A Simple Method for Azido Group Reduction," *Syn. Lett., 1991* 342.

Prakash et al., "Molecular Recognition by Circular Oligonucleotides. Strong Binding of Single-stranded DNA and RNA," *J. Chem. Soc. Chem. Commun.,* 1991 1161-1163.

Quaedflieg et al., "Synthesis of (3'-5') methylene Acetal Linked Dinuclosides Containing Cytosine Bases" *Recl. Tray. Chim Pays-Bas* 1991 110 435-436.

Rawson, T. E. and Webb, T. R., "The Synthesis of 5'-Homo-2'-Deoxycytidine", Nucleosides & Necleotides 1990, 9, 89-96.

Rebek, Jr., "Molecular Recognition and Biophysical Organic Chemistry," *Ace. Chem. Res., 1990* 23 399-404.

Rentzeperis et al., "Contribution of Loops and Nicks to the Formation of DNA Dumbbells: Melting Behavior and Ligand Binding," *Biochemistry,* 1993 32, 2564-2572.

Robins et al., "Nucleic Acid Related Compounds. 42. A General Procedure for the Efficient Deoxygenation of Secondary Alcohols. Regiospecific and Stereoselective Conversation of Ribonucleosides to 2'-Deoxynucleosides," *J. Am. Chem. Soc.,* 1983 105, 4059-4065.

Samano et al., "Mild Periodinane Oxidation of Protected Nucleosides to Give 2'-and 3'-Ketonucleosides. The First Isolation of a Purine 2'-Deoxy-3'-ketonucleoside Derivative" *J. Org. Chem.* 1990 55 5186-5188.

Sanghvi et al., "Synthesis and Structure of Methylene(dimethylhydrazo) Linked Thymidine Dimer and Their Utility as Antisense Oligonucleotides," *Collect. Czech. Chem. Commun.,* 1993 58 158-162.

Schneider et al., "Building Blocks for Oligonucleotide Analogs with Dimethylene-Sulfide, Sulfoxide, and Sulfone Groups Replacing Phosphodiester Linkages" *Tet. Letters* 1990 31, 335-338.

Secrist III et al., Abstract 21, "Synthesis and Biological Activity of 4'-Thionucleosides," *Program & Abstracts, Tenth International Roundtable, Nucleosides, Nucleotides and their Biological Applications,* Park City, Utah, Sept. 16-20, 1992.

Shaw et al., "Modified deoxyoligonucleotides stable to exonuclease degradation in serum," *Nucleic Acids Research,* 1991 19 747-749.

Shum et al., Synthesis of 3'-5'-Bis (Deoxythymidylyl) Difluoromethylphosphonate, Third Chemical Congress of North America, Organic Chemistry, 1988, Canada, June 5-10, 1988, Abstract No. 319.

Sproat et al., "2'-O-Methyloligoribonucleotides: Synthesis and Applications," *Oligonucleotides and Analogs A Practical Approach,* F. Eckstein Ed., IRL Press, p. 55, 1991.

Stevenson et al., "Inhibition of Human Immunodeficiency Virus Type 1-mediated Cytopathic Effects by Poly(L-lysine)-conjugated Synthetic Antisense Oligodeoxyribonucleotides", *J. gen. Virol.* 1989 70 2673-2682.

Stirchak et al., "Uncharged stereoregular nucleic acid analogs: 2. Morpholino nucleoside oligomers with carbamate internucleoside linkages", *Nucleic Acids Research* 1989 17 6129-6134.

Stirchak et al., "Uncharged Stereoregular Nucleic Acid Analogues. 1. Synthesis of a Cytosine-Containing Oligomer with Carbamate Internucleoside Linkages", *J. Org. Chem.* 1987 52, 4202-4206.

Suami, T. "Sugar hydrazino derivatives" JP 49024457 (Japanese patent) 22 June 1974 (Abstract).

Tittensor et al., "The Preparation of Nucleoside Carbonates", *J. Chem. Soc +;l 1971, C, 2656-2662.*

Pudlo et al., "A new and noval approach towards the synthesis of 3'-deoxy-3'-hydroxymethyl ribofluranosides", *Tetrahedron Letters* 1990, 31 (22), 3101-3104.

Trainor et al., "The Design and Synthesis of Fluorescence-Tagged Dideoxynucleotides for Automated DNA Sequencing", Third Chemical Congress of North America, Organic Chemistry, 1988, Canada, June 5-10, 1988, Abstract No. ORGN 317.

Trapani et al., "N-1-Alkenyl-N,S-Diacyl-2-Aminobenzenethiols (Enamides) by Ring-Opening of 2,3-Dihydro-1, 3-benzothiazoles with Aliphatic Carboxylic Anhydrides," *Synthesis,* 84, 1988.

Tronchet et al., "Blocked Disaccharide Analogs Bearing an Oxyimino interglycosidic Bridge", *J. Carbohydrate Chemistry* 1991, 10(4), 723-728.

Trost et al., ed., *Comprehensive Organic Synthesis,* 1991 4, Pergamon Press, 758-776.

Tseng et al., "Antisense oligonucleotide technology in the development of cancer therapeutics", *Cancer Gene Therapy* 1994, 1(1), 65-71.

Tuladhar et al., "A Synthetic Route to Poly-N,N'-Dimethylethylenediamines," *Tet. Letts., 1992* 33 2203-2206.

Uhlmann et al., "Antisense Oligonucleotides: A New Therapeutic Principle," *Chem. Rev.* 1990 90 543-584.

van der Krol et al., "Modulation of Eukaryotic Gene Expression by Complementary RNA or DNA Sequences", *BioTechniques* 1988 6 958-961.

Vasseur et al., "Oligonucleosides: Synthesis of a Novel Methylhydroxylamine-Linked Nucleoside Dimer and Its Incorporation into Antisense Sequences," *J. Am. Chem. Soc.,* 1992 114 4006-4007.

Veeneman et al., "An Efficient Approach to the Synthesis of Thymidine Derivatives Containing Phosphate-Isosteric Methylene Acetal Linkages", *Tetrahedron* 1991 47, 8, 1547-1562.

Veeneman et al., "Synthesis of Oligodeoxynucleotides Containing Thymidines Linked Via an Internucleosidic-(3'-5')-Methylene Bond", *Recueil des Travaux Chimiques des Pays-Bas* 1990 109 7-8 449-451.

Verheyden et al., "Halo Sugar Nucleosides. I. Iodination of Primary Hydroxyl Groups of Nucleosides with Methyltriphenoxyphosphonium Iodide," *J. Org. Chem.,* 1970 35 2319-2326.

Verheyden et al., "Halo Sugar Nucleosides. II. Iodination of Secondary Hydroxyl Groups of Nucleosides with Methyltriphenoxyphosphonium Iodide," *J. Org. Chem.,* 1970 35 2868-2877.

Wilson, "Cellular Transport Mechanisms," *Ann. Rev. Biochem.,* 1978 47 933-965.

Wright et al., "Large Scale Synthesis of Oligonucleotides via Phosphoramidite Nucleosides and a High-loaded Polystyrene Support," *Tetrahedron Letters,* 1993 34, 3373-3376.

Wu, J.-C. et al., "New Synthesis of 2', 3-Dideoxy-3'-C-Cyano-2'-Substituted Thymidines by Michael Addition Reactions," *Tetrahedron,* 1989 855-862.

Wu, G.Y. et al., "Evidence for Targeted Gene Delivery to Hep G2 Hepatoma Cells in Vitro" *Biochem.,* 1988 27: 887-892.

Yamamoto et al., "One-Step Synthesis of 5'-Azido-nucleosides," *J. Chem. Soc. Perkin* I 1980 306-310.

Yang et al., "Construction of Glycosidic N-O Linkages in Oligosaccharides," *J. Am. Chem. Soc.,* 1991 113 4715-4716.

Zon, "Pharmaceutical Considerations" in *Oligodeoxynucleotides: Antisense Inhibitors of gene Expression*, ed. J. S. Cohen, Chapter 11, CRC Press, Boca Raton, Florida, 1989, 234-247.

Zon et al., "Phosphorothioate oligonucleotides" in *Oligonucleotides and Analogues A Practical Approach*, Chapter 4, F. Eckstein, Ed., IRL Press, pg. 87-108, 1991.

Zon, "Oligonucleoside Phosphorothioates" in *Protocols for Oligonucleotides and Analogs Synthesis and Properties*, Chapter 8, Agrawal, S., ed., New Jersey: Humana Press, 1993, pgs. 165-189.

Zuckermann et al., "Efficient Method for the Preparation of Peptoids [Oligo(N-substituted glycines)] by Submonomer Solid-phase Synthesis," *J. Am. Chem. Soc.*, 1992 114 10646-10647.

BACKBONE MODIFIED OLIGONUCLEOTIDE ANALOGS

CROSS REFERENCE TO RELATED APPLICATIONS

This application is a continuation-in-part of U.S. application Ser. No. 703,619, filed May 21, 1991, now U.S. Pat. No. 5,378,825, which is a continuation-in-part of U.S. application Ser. No. 566,836, filed Aug. 13, 1990, now U.S. Pat. No. 5,223,618, and U.S. Ser. No. 558,663, filed Jul. 27, 1990, now U.S. Pat. No. 5,138,045. Each of these patents is incorporated herein by reference.

FIELD OF TEE INVENTION

This invention relates to the design, synthesis and application of nuclease resistant oligonucleotide analogs which are useful for therapeutics, diagnostics and as research reagents. The oligonucleotide analogs of the invention have modified linkages instead of the phosphorodiester bonds that normally serve as inter-sugar linkages in wild type nucleic acids. The analogs of the invention are resistant to nuclease degradation and are capable of modulating the activity of DNA and RNA. Methods for synthesizing these oligonucleotide analogs and for modulating the production of proteins using the oligonucleotide analogs of the invention are also provided.

BACKGROUND OF THE INVENTION

It is well known that most of the bodily states in mammals, including most disease states, are effected by proteins. Such proteins, either acting directly or through their enzymatic functions, contribute in major proportion to many diseases in animals and man.

Classical therapeutics has generally focused upon interactions with such proteins in an effort to moderate their disease causing or disease potentiating functions. Recently, however, attempts have been made to moderate the actual production of such proteins by interactions with the molecules (i.e., intracellular RNA) that direct their synthesis. These interactions have involved the hybridization to RNA of complementary "antisense" oligonucleotides or certain analogs thereof. Hybridization is the sequence-specific hydrogen bonding of oligonucleotides or oligonucleotide analogs to RNA or to single stranded DNA. By interfering with the production of proteins, it has been hoped to effect therapeutic results with maximum effect and minimal side effects. Oligonucleotide analogs also may modulate the production of proteins by an organism by a similar mechanism.

The pharmacological activity of antisense oligonucleotides and oligonucleotide analogs, like other therapeutics, depends on a number of factors that influence the effective concentration of these agents at specific intracellular targets. One important factor for oligonucleotides is the stability of the species in the presence of nucleases. It is unlikely that unmodified oligonucleotides will be useful therapeutic agents because they are rapidly degraded by nucleases. Modifications of oligonucleotides to render them resistant to nucleases therefore are greatly desired.

Modifications of oligonucleotides to enhance nuclease resistance have generally taken place on the phosphorus atom of the sugar-phosphate backbone. Phosphorothioates, methyl phosphonates, phosphoramidates, and phosphorotriesters have been reported to confer various levels of nuclease resistance. However, phosphate-modified oligonucleotides of this type generally have suffered from inferior hybridization properties. Cohen, J. S., ed. *Oligonucleotides: Antisense Inhibitors of Gene Expression*, (CRC Press, Inc., Boca Raton, Fla., 1989).

Another key factor is the ability of antisense compounds to traverse the plasma membrane of specific cells involved in the disease process. Cellular membranes consist of lipid-protein bilayers that are freely permeable to small, nonionic, lipophilic compounds yet inherently impermeable to most natural metabolites and therapeutic agents. Wilson, D. B. *Ann. Rev. Biochem.* 47: 933–965 (1978). The biological and antiviral effects of natural and modified oligonucleotides in cultured mammalian cells have been well documented. Thus, it appears that these agents can penetrate membranes to reach their intracellular targets. Uptake of antisense compounds by a variety of mammalian cells, including HL-60, Syrian Hamster fibroblast, U937, L929, CV-1 and ATH8 cells, has been studied using natural oligonucleotides and certain nuclease resistant analogs, such as alkyl triesters. Miller, P. S., Braiterman, L. T. and Ts'O, P.O.P., *Biochemistry* 16: 1988–1996 (1977); methyl phosphonates, Marcus-Sekura, C. H., Woerner, A. M., Shinozuka, K., Zon, G., and Quinman, G. V., *Nuc. Acids Res.* 15: 5749–5763 (1987) and Miller, P. S., McParland, K. B., Hayerman, K. and Ts'O, P.O.P., *Biochemistry* 16: 1988–1996 (1977) and Loke, S. K., Stein, C., Zhang, X. H. Avigan, M., Cohen, J. and Neckers, L. M. *Top. Microbiol. Immunol.* 141: 282:289 (1988).

Modified oligonucleotides and oligonucleotide analogs often are less readily internalized than their natural counterparts. As a result, the activity of many previously available antisense oligonucleotides has not been sufficient for practical therapeutic, research or diagnostic purposes. Two other serious deficiencies of prior art oligonucleotides that have been designed for antisense therapeutics are inferior hybridization to intracellular RNA and the lack of a defined chemical or enzyme-mediated event to terminate essential RNA functions.

Modifications to enhance the effectiveness of the antisense oligonucleotides and overcome these problems have taken many forms. These modifications include base ring modifications, sugar moiety modifications, and sugar-phosphate backbone modifications. Prior sugar-phosphate backbone modifications, particularly on the phosphorus atom, have effected various levels of resistance to nucleases. However, while the ability of an antisense oligonucleotide to bind to specific DNA or RNA with fidelity is fundamental to antisense methodology, modified phosphorus oligonucleotides have generally suffered from inferior hybridization properties.

Replacement of the phosphorus atom has been an alternative approach in attempting to avoid the problems associated with modification on the pro-chiral phosphate moiety. Some modifications in which replacement of the phosphorus atom has been achieved are disclosed by: Matteucci, M. *Tetrahedron Letters* 31: 2385–2388 (1990), wherein replacement of the phosphorus atom with a methylene group is limited by available methodology which does not provide for uniform insertion of the formacetal linkage throughout the backbone, and its instability, making it unsuitable for work; Cormier, et al. *Nucleic Acids Research* 16: 4583–4594 (1988), wherein replacement of the phosphorus moiety with a diisopropylsilyl moiety is limited by methodology, solubility of the homopolymers and hybridization properties; Stirchak, et al. *Journal of Organic Chemistry* 52: 4202–4206 (1987), wherein replacement of the phosphorus linkage by short homopolymers containing carbamate or morpholino linkages is limited by methodology, the solubility of the resulting molecule, and hybridization properties; Mazur, et al. *Tetrahedron* 40: 3949–3956 (1984), wherein replacement of the phosphorus linkage with a phosphonic linkage has not been developed beyond the synthesis of a homotrimer molecule; and Goodchild, J., *Bioconjugate Chemistry* 1: 165–187 (1990), wherein ester linkages are enzymatically degraded by esterases and are therefore unsuitable to replace the phosphate bond in antisense applications.

The limitations of the available methods for modification of the phosphorus backbone have led to a continuing and long felt need for other modifications which provide resistance to nucleases and satisfactory hybridization properties for antisense oligonucleotide diagnostics, therapeutics, and research.

OBJECTS OF THE INVENTION

It is an object of the invention to provide oligonucleotide analogs for use in antisense oligonucleotide diagnostics, research reagents, and therapeutics.

It is a further object of the invention to provide oligonucleotide analogs which possess enhanced cellular uptake.

Another object of the invention is to provide such oligonucleotide analogs which have greater efficacy than unmodified antisense oligonucleotides.

It is yet another object of the invention to provide methods for synthesis and use of such oligonucleotide analogs.

These and other objects will become apparent to persons of ordinary skill in the art from a review of the present specification and the appended claims.

SUMMARY OF THE INVENTION

Compositions useful for modulating the activity of an RNA or DNA molecule in accordance with this invention generally comprise oligonucleotide analogs having at least portions of their backbone linkages modified. In these modifications, the phosphorodiester linkage of the sugar phosphate backbone found in wild type nucleic acids has been replaced with various four atom linking groups. Such four atom linking groups maintain a desired four atom spacing between the 3'-carbon of one sugar or sugar analog and the 4'-carbon of the adjacent sugar or sugar analog. Oligonucleotide analogs made in accordance with the teachings of the invention are comprised of a selected sequence which is specifically hybridizable with a preselected nucleotide sequence of single stranded or double stranded DNA or RNA. They are synthesized through, for example, known solid state synthetic methodology to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide or oligonucleotide analog of reasonable length which may be desired.

In the context of this invention, the term "nucleoside" refers to the unit made up of a heterocyclic base and its sugar. The term "nucleotide" refers to a nucleoside having a phosphate group on its 3' or 5' sugar hydroxyl group. Thus, nucleosides, unlike nucleotides, have no phosphate group. "oligonucleotide" refers to a plurality of joined nucleotide units formed in a specific sequence from naturally occurring bases and pentofuranosyl groups joined through a sugar group by native phosphodiester bonds. These nucleotide units may be nucleic acid bases such as guanine, adenins, cytosine, thymine or uracil. The sugar group can be a deoxyribose or ribose. This term refers to both naturally occurring and synthetic species formed from naturally occurring subunits.

The term "oligonucleotide analog" as used in connection with this invention, refers to moieties which function similarly to oligonucleotides but which have non-naturally occurring portions. Oligonucleotide analogs can have altered sugar moieties, altered base moieties or altered inter-sugar linkages. For the purposes of this invention, an oligonucleotide analog having non-phosphodiester bonds, i.e., an altered inter-sugar linkage, can alternately be considered as an "oligonucleoside." Such an oligonucleoside thus refers to a plurality of joined nucleoside units joined by linking groups other than native phosphodiester linking groups. Additionally, for the purposes of this invention, the terminology "oligomers" can be considered to encompass oligonucleotides, oligonucleotide analogs or oligonucleosides. Thus, in speaking of "oligomers" reference is made to a series of nucleosides or nucleoside analogs that are joined together via either natural phosphodiester bonds or via other linkages including the four atom linkers of this invention. Generally, while the linkage is from the 3' carbon of one nucleoside to the 5' carbon of a second nucleoside, the term "oligomer" can also include other linkages such as a 2'–5' linkage.

Oligonucleotide analogs can also comprise other modifications consistent with the spirit of this invention, particularly that increase nuclease resistance and, thus, facilitate antisense therapeutic, diagnostic, or research reagent use of a particular oligonucleotide. For example, when the sugar portion of a nucleoside or nucleotide is replaced by a carbocyclic or other moiety, it is no longer a sugar. Moreover, when other substitutions, such a substitution for the inter-sugar phosphorodiester linkage are made, the resulting material is no longer a true nucleic acid species. The compounds that result from such substitutions all are denominated as analogs. Throughout this specification, reference to the sugar portion of a nucleic acid species shall be understood to refer to either a true sugar or to a species taking the traditional space of the sugar of wild type nucleic acids. Moreover, reference to inter-sugar linkages shall be taken to include moleties serving to join the sugar or sugar analog portions together in the fashion of wild type nucleic acids.

In accordance with the present invention, novel types of antisense oligonucleotide analogs and oligonucleosides are provided which are modified to enhance cellular uptake, nuclease resistance, and hybridization properties and to provide a defined chemical or enzymatically mediated event to terminate essential RNA functions.

It has been found that certain classes of oligonucleotide analog compositions can be useful in therapeutics and for other objects of this invention. Such oligonucleotide analogs are formed from subunits, at least some of which have the structure:

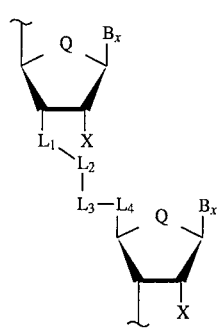

wherein $B_x$ is a variable base moiety; Q is O, $CH_2$, CHF or $CF_2$ and X is H; OH; $C_1$ to $C_{10}$ lower alkyl, substituted lower alkyl, alkaryl or aralkyl; F; Cl; Br; CN; $CF_3$; $OCF_3$; OCN; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino or substituted silyl. Moreover, X can be an RNA cleaving group; a group for improving the pharmacokinetic properties of an oligonucleotide; or a group for improving the pharmacodynamic properties of an oligonucleotide.

$L_1$ and $L_4$ are, independently, $CH_2$, C=O, C=S, C—$NH_2$, C—$NHR_3$, C—OH, C—SH, C—O—$R_1$ or C—S—$R_1$. $L_2$ and $L_3$ are, independently, $CR_1R_2$, C=$CR_1R_2$, C=$NR_3$, $P(O)R_4$, $P(S)R_4$, C=O, C=S, O, S, SO, $SO_2$, $NR_3$ or $SiR_5R_6$; or, together, form part of an alkene, alkyne, aromatic ring, carbocycle or heterocycle. $L_1$, $L_2$, $L_3$ and $L_4$, together, can comprise a —CH=N—NH—$CH_2$— or —$CH_2$—O—N=CH— moiety.

$R_1$ and $R_2$ are, independently, H; OH; SH; $NH_2$; $C_1$ to $C_{10}$ alkyl, substituted alkyl, alkenyl, alkaryl or aralkyl; alkoxy; thioalkoxy; alkylamino; aralkylamino; substituted alkylamino; heterocycloalkyl; heterocycloalkylamino; aminoalkylamino; polyalkylamino; halo; formyl; keto; benzoxy; carboxamido; thiocarboxamido; ester; thioester; carboxamidine; carbamyl; ureido or guanidino. They can also independently comprise an RNA cleaving group; a group for improving the pharmacokinetic properties of an oligonucleotide; or a group for improving the pharmacodynamic properties of an oligonucleotide;

$R_3$ is H, OH, $NH_2$, lower alkyl, substituted lower alkyl, alkoxy, lower alkenyl, aralkyl, alkylamino, aralkylamino, substituted alkylamino, heterocycloalkyl, heterocycloalkylamino, aminoalkylamino, polyalkylamino, an RNA cleaving group, a group for improving the pharmacokinetic properties of an oligonucleotide or a group for improving the pharmacodynamic properties of an oligonucleotide. $R_4$ is OH, SH, $NH_2$, O-alkyl, S-alkyl, NH-alkyl, O-alkylheterocyclo, S-alkylheterocyclo, N-alkylheterocyclo or a nitrogen-containing heterocycle.

$R_5$ and $R_6$ are, independently, $C_1$ to $C_6$ alkyl or alkoxy; provided that if $L_2$ is $P(O)R_4$ and $R_4$ is OH and X is OH and $B_x$ is uracil or adenine, then $L_3$ is not O; and that if $L_1$, $L_2$ and $L_4$ are $CH_2$ and X is H or OH and Q is O then $L_3$ is not S, SO or $SO_2$.

In accordance with preferred embodiments, the oligonucleotide analogs of the invention comprise sugar moieties, such that Q is O. In accordance with other embodiments, each of $L_1$ and $L_4$ are either $CR_1R_2$ or C=O, preferably $CR_1R_2$. It is also preferred that $L_2$ and $L_3$ be, independently, $CR_1R_2$, O, $P(O)R_4$, $P(S)R_4$ or $NR_3$ and especially that one of $L_2$ and $L_3$ be $CR_1R_2$ and the other of $L_2$ and $L_3$ be $P(O)R_4$ or $P(S)R_4$. Combinations where $L_2$ is O and $L_3$ is $P(O)R_4$ or $P(S)R_4$ are also preferred.

In accordance with other embodiments, the oligonucleotide analogs of this invention are such that each of $L_2$ and $L_3$ is $NR_3$ where $R_3$ is preferably H. More preferably, the oligonucleotide analogs have one of the following formulas:

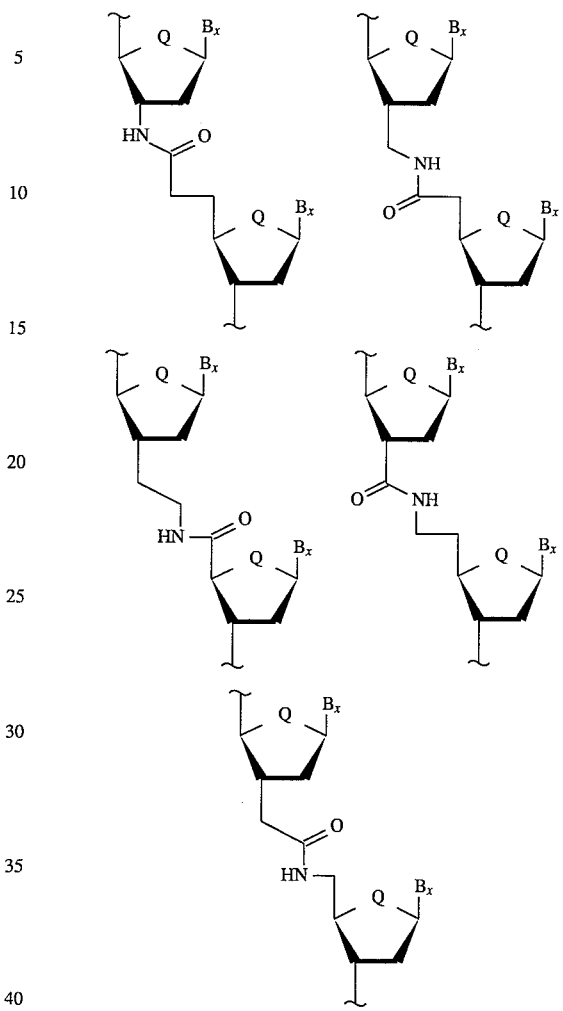

Alternatively, the analogs of the invention can be such that $L_2$ and $L_3$ taken together, form a portion of a cyclopropyl, cyclobutyl, ethyleneoxy, ethyl aziridine or substituted ethyl aziridine ring. $L_2$ and $L_3$ taken together can also form a portion of a $C_3$ to $C_6$ carbocycle or 4-, 5- or 6-membered nitrogen heterocycle.

Thus, $L_1$—$L_2$—$L_3$—$L_4$ can be selected from NR—C(O)—$CH_2$—$CH_2$, NR—C(S)—$CH_2$—$CH_2$, $CH_2$—NR—C(O)—$CH_2$, $CH_2$—NR—C(S)—$CH_2$, $CH_2$—$CH_2$—NR—C(O), $CH_2$—$CH_2$—NR—C(S), C(O)—NR—$CH_2$—$CH_2$, C(S)—NR—$CH_2CH_2$, $CH_2$—C(O)—NR—$CH_2$, and $CH_2$—C(S)—NR—$CH_2$ where R is hydrogen, alkyl, substituted alkyl, aralkyl, alkenyl, alkaryl, aminoalkyl, hydroxyalkyl, heterocycloalkyl, heterocycloaralkyl, an RNA cleaving group, a group for improving the affinity for the RNA complement or a group for improving the pharmacodynamic properties of the oligonucleotide. The remaining subunits of the oligonucleotides are natural or synthetic subunits as will be appreciated by persons of ordinary skill in the art.

It is preferred that the oligonucleotide analogs be such that X is H or OH, or, alternatively F, O-alkyl or O-alkenyl, especially where Q is O. The group $B_x$ is preferably adenine, guanine, uracil, thymine, cytosine, 2-aminoadenosine or 5-methylcytosine, although other non-naturally occurring species can be employed.

Other preferred embodiments are those where $L_1$ and $L_4$ are each $CH_2$, especially where $L_2$ and $L_3$ are each NH. Alternatively, one of $L_2$ and $L_3$, preferably, $L_3$, is O and the other of $L_2$ and $L_3$ is NH.

It is preferred that the oligonucleotide analogs of the invention comprise from about 4 to about 50 subunits, and even more preferably from about 5 to about 20 subunits having the given structure. While substantially each subunit of the oligonucleotide analogs can have said structure, it is also desirable for substantially alternating subunits to have said structure.

The oligonucleotide analogs of this invention are preferably prepared in a pharmaceutically acceptable carrier for therapeutic administration to patients. The analogs are believed to exhibit improved nuclease resistance as compared to corresponding wild type oligonucleotides. This invention is also directed to methods for modulating the production or activity of a protein in an organism comprising contacting the organism with an oligonucleotide analog specifically hybridizable with at least a portion of a nucleic acid sequence coding for said protein, wherein at least some of the subunits of the analog have the foregoing structure.

Additionally, the invention is directed to methods for treating an organism having a disease characterized by the undesired production of a protein comprising contacting the organism with an oligonucleotide analog hybridizable with at least a portion of a nucleic acid sequence coding for said protein, either alone or in a pharmaceutically acceptable carrier, wherein at least some of the subunits of the analog have the given structure.

In another aspect, the present invention provides compounds useful in preparing the above-described oligonucleotide analogs. In certain embodiments, these compounds have a structure:

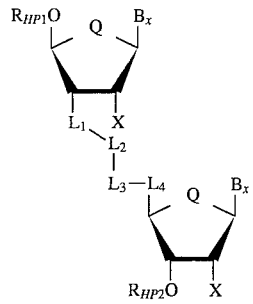

wherein $R_{HP1}$ and $R_{HP2}$ are, independently, H or hydroxyl protecting groups. In certain embodiments, these compounds are prepared by providing a first synthon having structure (I) and second synthon having structure (II):

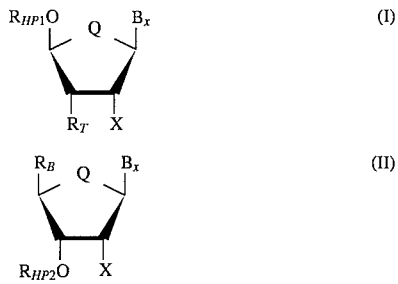

wherein:
(a) $R_T$ is $NH_2$ and $R_B$ is $R_A$—$CH_2$—$CH_2$;
(b) $R_T$ is $CH_2$—$NH_2$ and $R_B$ is $R_A$—$CH_2$;
(c) $R_T$ is $CH_2$—$CH_2$—$NH_2$ and $R_B$ is $R_A$;
(d) $R_T$ is $R_A$ and $R_B$ is $NH_2$—$CH_2$—$CH_2$; or (e) $R_T$ is $CH_2$—$R_A$ and $R_B$ is $NH_2$—$CH_2$;
where $R_A$ is C(O)OH, C(S)OH, or an activated derivative thereof; and
coupling the first and second synthons to form an amide or thioamide linkage through the $R_T$ and $R_B$ groups.

This invention also provides methods for synthesizing oligonucleotide analogs, including those useful in the practice of the therapeutic methods of the invention. Certain of these methods comprise providing a first moiety comprising the structure:

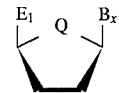

and a second moiety comprising the structure:

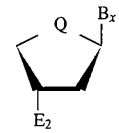

wherein $B_x$ is a variable base moiety; Q is O, $CH_2$, CHF or $CF_2$; and $E_1$ and $E_2$ are the same or different and are electrophilic reactive groups; and coupling said first and second moieties with a linking group through said electrophilic reactive groups to form said oligonucleotide analog. In accordance with preferred methods, the electrophilic reactive group of the first moiety comprises halomethyl, trifluoromethyl, sulfonylmethyl, p-methylbenzene sulfonylmethyl, or 3'-C-formyl, while the electrophilic reactive group of the second moiety comprises halogen, sulfonylmethyl, p-methyl-benzene sulfonyl methyl, or aldehyde. It is preferred that the linking group be hydrazine or hydroxylamine.

It is useful to formulate therapeutic compositions where at least one portion of said oligonucleotide analog is incorporated into a further oligonucleotide species to provide said further oligonucleotide analog with wild type phosphodiester bonds substantially alternating with areas so coupled. The incorporation is preferably achieved by phosphodiester linkage of a desired sequence of dinucleotides, said dinucleotides having been previously so coupled.

Precursor nucleosides are also contemplated by this invention having the structure:

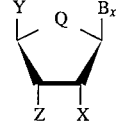

wherein $B_x$ is a variable base moiety Q is O, $CH_2$, CHF or $CF_2$; and X is H; OH; $C_1$ to $C_{10}$ lower alkyl, substituted lower alkyl, alkaryl or aralkyl; F; Cl; Br; CN; $CF_3$; $OCF_3$; OCN; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a group for improving the pharmacokinetic properties of an oligonucleotide; or a group for improving the pharmacodynamic properties of an oligonucleotide.

In such species, Y is hydroxyl, aminomethyl, hydrazinomethyl, hydroxymethyl, C-formyl, phthalimidohydroxymethyl, aryl-substituted imidazolidino, aminohydroxylmethyl, ortho-methylaminobenzenethio, methylphosphonate and methylalkylphosphonate. Z is H, hydroxyl, aminomethyl, hydrazinomethyl, hydroxymethyl, C-formyl, phthalimidohydroxymethyl, aryl substituted imidazolidino, aminohydroxylmethyl, ortho-methylaminobenzenethio, methylphosphonate or methyl alkylphosphonate. All of the foregoing is with the proviso that when Q is O and Y is hydroxymethyl and X is H or OH then Z is not C-formyl; and that when Q is O and X is H or OH and Z is hydroxyl then Y is not aminohydroxylmethyl, hydrazinomethyl or aryl substituted imidazolidino. It is preferred that X be H or OH and that Q be O.

Oligonucleotide analogs having modified sugar linkages have been found to be effective in accomplishing these goals. The oligonucleotide analogs preferably range from about 4 to about 50 nucleic acid base subunits in length, with from about 5 to about 20 being more preferred. Oligonucleotide analogs described in this invention are hybridizable with preselected nucleotide sequences of single stranded or double stranded DNA and RNA. The nucleic acid bases which comprise this invention can be pyrimidines such as thymine, uracil or cytosine or purines such as guanine or adenine, or modifications thereof such as 5-methylcytosine, arranged in a selected sequence. The sugar moiety can be of the ribose or deoxyribose type or a sugar mimic such as a carbocyclic ring. In accordance with one preferred embodiment of this invention, the oligonucleotide analogs or oligonucleosides hybridize to HIV mRNA encoding the tat protein, or to the TAR region of HIV mRNA. The oligonucleotide analogs or oligonucleosides can mimic the secondary structure of the TAR region of HIV mRNA to bind the tat protein. Other preferred antisense oligonucleotide analog or oligonucleoside sequences include complementary sequences for herpes, papilloma and other viruses.

The modified linkages of this invention preferably use a four atom linking group to replace the naturally occurring phosphodiester-5'-methylene linkage. Replacement of the naturally occurring linkage by four atom linkers of the present invention confers nuclease resistance and enhanced cellular uptake upon the resulting oligonucleotide analog. Preferably included within the four atom linker is a 3'-deoxy function on one of the linked sugars. The four atom linker is of the structure —$L_1$—$L_2$—$L_4$— wherein $L_1$ and $L_4$ are methylene carbon atoms or substituted carbon atoms and $L_2$ and $L_3$ are methylene carbon atoms, substituted carbon atoms, oxygen atoms, nitrogen or substituted nitrogen atoms, substituted phosphorus atoms, sulfur or substituted sulfur atoms or substituted silicon atoms. It is preferred that the modified linkage occur at substantially each linkage location. Alternatively, modification can occur at less than every location such as at alternating linkage locations or substantially randomly. The linkage can be neutral or can be positively or negatively charged.

This invention is also directed to methods for synthesizing such oligonucleosides. The invention provides for the coupling of a 3'-deoxy-3'-substituted, especially methyl substituted, nucleoside with a 5'-deoxy-5'-substituted nucleoside through the addition of a two atom fragment or substituted two atom fragment. The addition reaction can occur through a stepwise procedure involving the activation of the 3' and 5' positions of respective nucleosides to a variety of suitable electrophilic moieties, followed by the addition of a suitable linking group to react with the electrophiles. In the alternative, the procedure can occur in a concerted manner. Such methods can employ solid supports via a DNA synthesizer, by manual manipulation of the support, or otherwise.

This invention is also directed to methods for modulating the production of proteins by an organism comprising contacting the organism with a composition formulated in accordance with the foregoing considerations. It is preferred that the RNA or DNA portion which is to be modulated be preselected to comprise that portion of DNA or RNA which codes for the protein whose formation or activity is to be modulated. The targeting portion of the composition to be employed is, thus, selected to be complementary to the preselected portion of DNA or RNA, that is to be an antisense oligonucleotide for that portion.

This invention is also directed to methods for treating an organism having a disease characterized by the undesired production of a protein. This method comprises contacting the organism with a composition in accordance with the foregoing considerations. The composition is preferably one which is designed to specifically bind with messenger RNA which codes for the protein whose production or activity is to be modulated. The invention further is directed to diagnostic methods for detecting the presence or absence of abnormal RNA molecules or abnormal or inappropriate expression of normal RNA molecules in organisms or cells.

This invention is also directed to methods for the selective binding of RNA for research and diagnostic purposes. Such selective, strong binding is accomplished by interacting such RNA or DNA with compositions of the invention which are resistant to degradative nucleases and which hybridize more strongly and with greater fidelity than known oligonucleotides or oligonucleotide analogs.

DETAILED DESCRIPTION OF PREFERRED EMBODIMENTS

Figure 1:
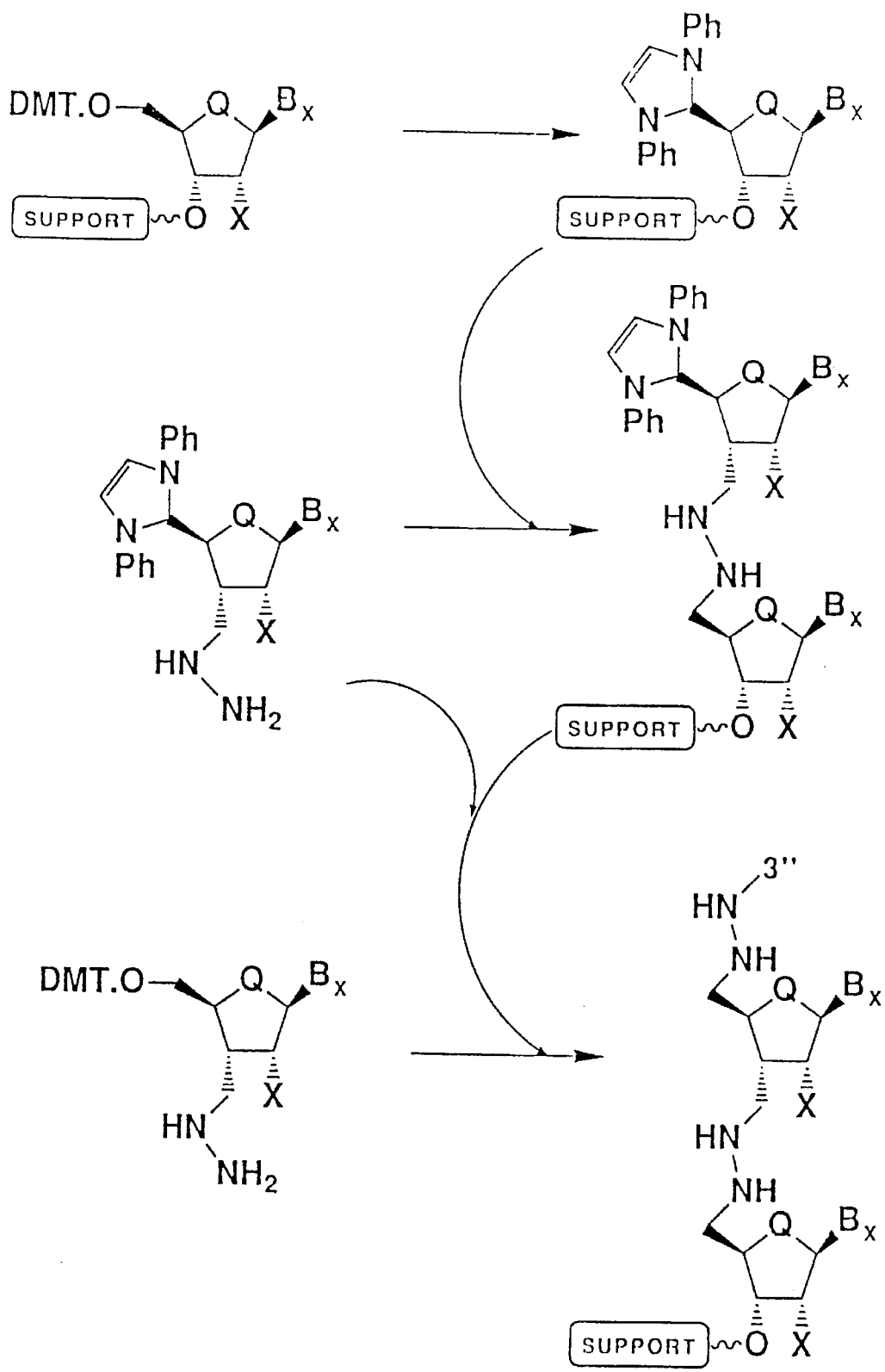
FIG. 1 is a schematic, synthetic scheme in accordance with certain embodiments of the invention.

The biological activity of the antisense oligonucleotides previously available has not generally been sufficient for practical therapeutic research or diagnostic use. This invention is directed to modified oligonucleotides, i.e. oligonucleotide analogs or oligonucleosides, and to methods for effecting useful modifications. These modified oligonucleotides and oligonucleotide analogs exhibit increased stability relative to their naturally occurring counterparts. Extracellular and intracellular nucleases generally do not recognize and, therefore, do not bind to the backbone modified oligonucleotide analogs or oligonucleosides of the present invention. Any binding by a nuclease to the backbone will not result in cleavage of the nucleosidic linkages due to the lack of sensitive, phosphorus-oxygen bonds. In addition, the resulting, novel neutral or positively charged backbones of the present invention can be taken into cells by simple passive transport rather than requiring complicated protein mediated processes. Another advantage of the present invention is that the lack of a negatively charged backbone facilitates the sequence specific binding of the oligonucleotide analogs or oligonucleosides to targeted RNA, which has a negatively charged backbone, and which will accordingly repel incoming similarly charged oligonucleotides. Still another advantage of the present invention is that sites for attaching functional groups which can initiate catalytic cleavage of targeted RNA are found in these structure types.

In accordance with preferred embodiments, this invention is directed to replacing inter-sugar phosphate groups to yield ologonucleotides having linkages as found in the structure:

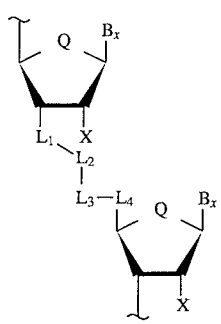

wherein $B_x$ is a variable base moiety;

Q is O, $CH_2$, CHF or $CF_2$;

X is H; OH; $C_1$ to $C_{10}$ lower alkyl, substituted lower alkyl, alkaryl or aralkyl; F; Cl; Br; CN; $CF_3$; $OCF_3$; OCN; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a group for improving the pharmacokinetic properties of an oligonucleotide; or a group for improving the pharmacodynamic properties of an oligonucleotide;

$L_1$ and $L_4$ are, independently, $CH_2$, C=O, C=S, C—$NH_2$, C—$NHR_3$, C—OH, C—SH, C—O—$R_1$ or C—S—$R_1$; and $L_2$ and $L_3$ are, independently, $CR_1R_2$, $C=CR_1R_2$, $C=NR_3$, $P(O)R_4$, $P(S)R_4$, C=O, C=S, O, S, SO, $SO_2$, $NR_3$ or $SiR_5R_6$; or, together, form part of an alkene, alkyne, aromatic ring, carbocycle or heterocycle;

$L_1$, $L_2$, $L_3$ and $L_4$, together, comprise a —CH=N—NH—$CH_2$— or —$CH_2$—O—N=CH— moiety; or $L_1$—$L_2$—$L_3$—$L_4$ is selected from NR—C(O)—$CH_2$—$CH_2$, NR—C(S)—$CH_2$—$CH_2$, $CH_2$—NR—C(O)—$CH_2$, $CH_2$—NR—C(S)—$CH_2$, $CH_2$—$CH_2$—NR—C(O), $CH_2$—$CH_2$—NR—C(S), C(O)—NR—$CH_2$—$CH_2$—, C(S)—NR—$CH_2$—$CH_2$, $CH_2$—C(O)—NR—$CH_2$, and $CH_2$—C(S)—NR—$CH_2$ where R is hydrogen, alkyl, substituted alkyl, aralkyl, alkenyl, alkaryl, aminoalkyl, hydroxyalkyl, heterocycloalkyl, heterocycloaralkyl, an RNA cleaving group, a group for improving the affinity for the RNA complement or a group for improving the pharmacodynamic properties of the oligonucleotide;

$R_1$ and $R_2$ are, independently, H; OH; SH; $NH_2$; $C_1$ to $C_{10}$ alkyl, substituted alkyl, alkenyl, alkaryl or aralkyl; alkoxy; thioalkoxy; alkylamino; aralkylamino; substituted alkylamino; heterocycloalkyl; heterocycloalkylamino; aminoalkylamino; polyalkylamino; halo; formyl; keto; benzoxy; carboxamido; thiocarboxamido; ester; thioester; carboxamidine; carbamyl; ureido; guanidino; an RNA cleaving group; a group for improving the pharmacokinetic properties of an oligonucleotide; or a group for improving the pharmacodynamic properties of an oligonucleotide;

$R_3$ is H, OH, $NH_2$, lower alkyl, substituted lower alkyl, alkoxy, lower alkenyl, aralkyl, alkylamino, aralkylamino, substituted alkylamino, heterocyclocalkyl, heterocycloalkylamino, aminoalkylamino, polyalkylamino, an RNA cleaving group, a group for improving the pharmacokinetic properties of an oligonucleotide and a group for improving the pharmacodynamic properties of an oligonucleotide;

$R_4$ is OH, SH, $NH_2$, O-alkyl, S-alkyl, NH-alkyl, O-alkylheterocycle, S-alkylheterocycle, N-alkylheterocycle or a nitrogen-containing heterocycle; and $R_5$ and $R_6$ are, independently, $C_1$ to $C_6$ alkyl or alkoxy; provided that if $L_2$ is $P(O)R_4$ and $R_4$ is OH and X is OH and $B_x$ is uracil or adenine, then $L_3$ is not O; and that if $L_1$, $L_2$ and $L_4$ are $CH_2$ and X is H or OH and Q is O then $L_3$ is not S, SO or $SO_2$.

In accordance with preferred embodiments of the invention $L_1$ and $L_4$ are methylene groups. In such preferred embodiments one of $L_2$ or $L_3$ can comprise an amino group and the other comprise an amino group or an oxygen. Thus, in certain preferred embodiments $L_2$ and $L_3$ together are hydrazino, aminohydroxy or hydroxyamino. In other preferred embodiments one of $L_1$ or $L_4$ together with one of $L_2$ or $L_3$ are a CH=N group and the other of $L_2$ or $L_3$ is an oxygen or nitrogen atom thus the linker includes oxime and hydrazone groupings, respectively. Such oxime or hydrazone linking groups can be reduced to the above referenced aminohydroxy or hydrazine groups.

In other preferred embodiments, the $L_1$—$L_2$—$L_4$ series contains a N-substituted or N-unsubstituted amide or thioamide functionality.

In still other preferred embodiments of the present invention, $L_2$ and $L_3$ are substituted carbon, amino, substituted amine, oxygen, sulfur, oxides of sulfur, phosphorus or silicon. The substituents on carbon include hydrogen, hydroxy, thio, amino, lower alkyl, substituted lower alkyl, alkoxy, thioalkoxy, lower alkenyl, aralkyl, alkylamino, aralkylamino, substituted alkylamino, heterocycloalkyl, heterocycloalkylamino, aminoalkylamino, polyalkylamino, halogen, formyl, keto, benzoxy, carboxamido, thiocarboxamido, ester, thioester, carboxamidine, carbamyl, ureido, guanidino, an RNA cleaving group, a group for improving the pharmacokinetic properties of an oligonucleotide or a group for improving the pharmacodynamic properties of an oligonucleotide. Additional preferred embodiments include $L_2$ and $L_3$ together being C=C. Further preferred embodiments include $L_2$ and $L_3$ together being a C—C, C=C, C—N or N—C two atom pair of a ring structure including carbocyclic, aromatic, heteroaromatic or heterocyclic rings. Still another preferred embodiment of the present invention provides that $L_1$ and $L_4$ independently are carboxy, thiocarboxy, methylamino, methylhydroxy, methylthio, ether or thioether.

The invention is also directed to methods for the preparation of oligonucleosides with modified inter-sugar linkages. These modifications can be effected using solid supports which can be manually manipulated or used in conjunction with a DNA synthesizer using methodology commonly known to those skilled in DNA synthesizer arts. Generally, the procedure involves functionalizing the sugar moieties of two nucleosides which will be adjacent to one another in the selected sequence. In a 5' to 3' sense, the "upstream" nucleoside is generally modified at the 3' sugar site and is referred to hereinafter as "synthon 1". In one process of the invention, ribo- and 2'-deoxyribonucleosides of adenine, guanine, cytosine, uracil, thymine and their analogs are modified to give their 3'-deoxy-3-hydroxymethyl analogs. These 3'-hydroxymethyl groups are then converted into various types of electrophilic centers. This can be accomplished in a number of ways such as the following, preferred scheme.

One class of starting materials, 3'-deoxy-3'-hydroxymethyl ribonucleosides, can be prepared as described by Townsend et al., *Tetrahedron Letters*, 31: 3101–3104 (1990), Samano, V. and M. J. Morris, *Journal of Organic Chemistry*, 55: 5186–5188 (1990) and Bergstrom, D. E., *Nucleosides and Nucleotides* 8(8): 1529–1535 (1989). Appropriate, known, selective sugar hydroxyl protection of these nucleosides followed by standard 2'-deoxygenation procedures will afford the 2',3'-dideoxy-3'-hydroxymethyl-ribonucleosides. Nucleosides of this type can be selectively protected and the 3'-hydroxymethyl moiety functionalized to a variety of suitable electrophilic moieties. In accordance with preferred embodiments of this invention, such electrophilic moieties include halomethyl, trifluoromethyl, sulfonylmethyl, p-methylbenzene sulfonylmethyl, hydrazinomethyl or 3'-C-formyl.

The "downstream" nucleoside is generally modified at the 5' sugar site and is referred to hereinafter as "synthon 2". Modification to produce ribo and 2'-deoxyribonucleosides of adenine, guanine, cytosine, uracil, thymine and their analogs, with their 5'-hydroxymethylene group converted into various types of electrophilic centers can be accomplished through various procedures using commercially available nucleosides. For example, 5'-deoxy-5'-halo nucleoside, 5'-deoxy-5'-tosyl nucleosides, and 5'-aldehydic nucleosides have been prepared by Jones, G. H. and J. G. Moffatt in *Journal of the American Chemical Society* 90: 5337–5338 (1968).

In general, synthon 1 can be represented as comprising the structure:

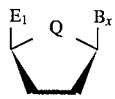

while synthon 2 generally comprises the structure:

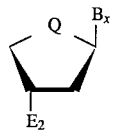

wherein $B_x$ is a variable base moiety; Q is O, $CH_2$, CHF or $CF_2$; and $E_1$ and $E_2$ are the same or different and are electrophilic reactive groups.

The two synthons are coupled via a linking group reactive with the electrophilic reactive groups or otherwise. Coupling between synthon 1 and synthon 2 can occur either stepwise or in a concerted manner and can result in dinucleosides linked through the modified linkage of the present invention or can result in a chain of nucleosides, each of which can be linked to the next through said modified linkage.

Coupling via a concerted action can occur between the electrophilic centers of synthon 1 and synthon 2 such as in the presence of ammonia or an ammonia derivative to produce a dinucleoside. A preferred embodiment of the present invention is the coupling of known, bromomethyl type synthons by the addition of hydrazine to produce a preferred linkage having $-L_1-L_2-L_3-L_4-$ equal to $-CH_2NHNHCH_2-$. Another preferred embodiment of the present invention is the coupling of bromomethyl type synthons by the addition of hydroxylamine to produce a linkage having $-L_1-L_2-L_3-L_4-$ equal to $-CH_2NHOCH_2-$ or $-CH_2ONHCH_2-$.

Another procedure whereby inter-sugar linkages can be modified to provide the dinucleoside structure described herein is via a Wittig reaction. Preferably, the starting material of such reaction is a 3'-keto nucleoside such as described by Townsend, et al. in *Tetrahedron Letters* 31: 3101–3104 (1990); Samano, V. and M. J. Morris in *Journal of Organic Chemistry* 55: 5186–5188 (1990); and Bergstrom, D. E., et al. in *Nucleosides and Nucleotides* 8(8):1529–1535 (1989); or a 5'-aldehydic nucleoside as described by Jones, G. H. and J. G. Moffatt in *Journal of the American Chemical Society* 90: 5337–5338 (1968). The starting material is preferably reacted with a phosphorus ylide having a benzyl or other protecting group. One preferred ylide useful for this invention is triphenylphosphorane-benzyloxymethylidine. Another useful ylide preferably used for this invention is triphenylphosphorane-benzyloxyethylidine. Reduction of the vinyl group and hydrogenolysis of the benzyl protecting group provides hydroxymethyl and hydroxyethyl moieties respectively, in the 5' or 3' positions of the desired nucleoside of guanine, adenine, cytosine, thymine, uracil or the analogs of these nucleosides. In addition, the Wittig reaction can be used to provide the 5' and 3' hydroxy alkyl moieties of carbocyclic nucleosides.

Conversion of the hydroxyl groups to provide electrophilic centers and subsequent coupling of a 3' electrophilic center with a 5' nucleophilic center will afford dinucleosides of the present invention. In one embodiment of the invention, the hydroxyl groups are converted to provide electrophilic centers such as bromides, triflates, and tosylates. Coupling affords dinucleosides connected by a carbon chain with one or two heteroatoms. Preferably such heteroatoms are O, NH, $NR_3$, S, SO, $SO_2$, $P(O)R_4$, $P(S)R_4$ or $SiR_5R_6$ as depicted in the generic formula provided previously.

Other useful dinucleosides which likely can be derived from a Wittig reaction involving 3' or 5' carbonyl nucleosides and triphenylphosphorine methylidine diphenylphosphonate are phosphonate dinucleosides. This reaction provides a methyl or ethyl phosphonate which can be condensed with the corresponding 5'- or 3'-hydroxy group to provide 3'- or 5'-phosphonate linked oligonucleosides. Chemistry of this type has been described in the preparation of phosphonates of dinucleosides for the study of biochemical processes, Moffatt, J. G., et al., *Journal of American Chemical Society* 92: 5510–5513 (1970) and Mazur, A., B. E. Tropp, and R. Engel, *Tetrahedron* 40: 3949–3956 (1984). Utilizing this type of coupling, a preferred embodiment is prepared by the coupling a 3'-keto nucleoside to a 5'-nucleoside with a symmetrical bis(methyltriphenylphosphane)phenylphosphate to provide 3',5'-dimethylphosphonate linked oligonucleotides In addition to the Wittig reaction, 3'-hydroxymethyl nucleosides can also be prepared by inversion of alpha carbocyclic nucleosides. This will provide the desired 3' hydroxymethyl group on the "down" or alpha face. This group can be protected and the 3"-hydroxyl group (identifying the exo-cyclic methyl linked to the sugar 3' position as 3" methyl) can be converted to a hydroxymethyl group or to a longer alkyl group. One method of converting the 3" group involves oxidation to a keto group, followed by a Wittig reaction with triphenylphosphorine methylidine diphenylphosphonate and reduction. Longer hydroxyalkyl groups can be placed in the 3"-position in this manner. This embodiment also provides a 4'-desmethyl-3'-hydroxymethyl nucleoside synthon. Coupling this 4'-desmethyl nucleoside and a normal 3'-hydroxy- nucleoside using a two atom coupler will provide dinucleoside synthons as described in prior pending application Ser. No. 566,836 filed Aug. 13, 1990, which application is assigned to the assignee of this application. Coupling of the 4'-desmethyl hydroxyl group with appropriate 3'-synthons as described above will provide a number of other types of novel dinucleoside synthons.

Yet another approach to functionalize the methyl group of 3'-deoxy-3'-methyl nucleosides can be elaborated from 3'-deoxy-3'-cyanonucleosides. Parkes, K. E. B., and K. Taylor, *Tetrahedron Letters* 29: 2995–2996 (1988) described a general method of synthesis of 3'-cyano nucleosides. In this method, 5'-trityl protected 2'-deoxynucleosides are 3'-iodinated with methyltriphenylphosphonium iodide. These materials are then treated with hexamethylditin, t-butylisonitrile, and 2,2'-azo-bisisobutyronitrile (AIBN) to provide the radical addition of a cyano group to the 3'-position. Conversion of the cyano group to an aldehyde was accomplished in high yield. Subsequently, the intermediate was converted to hydroxymethyl functions, which are valuable precursors to the electrophilic synthon 1.

An additional procedure whereby inter-sugar linkages can be modified to provide dinucleosides utilizes 3'-C-formyl derivatized nucleosides as synthon 1 and 5'-aminohydroxy derivatized nucleosides as synthon 2. Direct coupling of synthons 1 and 2 gave a dinucleoside coupled via an oxime linkage. In this instance, the oxime is present as E/Z isomers. The isomeric compounds are separated utilizing HPLC. Further in this instance, the oxime nitrogen atom is adjacent to a carbon atom on the 3'-end of the upstream nucleoside. Dinucleosides having the oxime nitrogen adjacent to a carbon atom on the 5' or downstream nucleoside are synthesized utilizing a 5'-C-formyl derivatized nucleoside as synthon 2 and a 3'-deoxy-3'-aminohydroxymethyl derivatized nucleoside as synthon 1. In this instance, oxime E/Z isomers are also obtained. In both instances the oxime linked dimers are useful for direct incorporation into an oligomer or can be reduced to the corresponding hydroxyamino linked dinucleoside. Reduction of oxime linked dinucleosides either as the dinucleoside or as a dinucleoside moiety in an oligomer with sodium cyanoborohydride yields the corresponding aminohydroxyl linked compounds. The hydroxyamino linked dinucleoside or a large oligomer could be alkylated at the amino moiety of the aminohydroxyl linkage to yield a corresponding N-alkylamino linkage.

The 3'-C-formyl derivatized synthon 1 can be formed via several synthetic pathways. The presently preferred method utilizes a radical carbonylation of the corresponding 3'-deoxy-3' iodo nucleoside. The iodo compound is treated with CO, AIBN, i.e., 2,2'-azobisisobutrylonitrile, and TTMS, i.e. tris(trimethylsilyl)silane. Alternately, it can be synthesized from either a 3'-deoxy-3' cyano sugar or nucleoside. Both 5'-C-formyl (also identified as 5'-aldehydo) and 3'-C-formyl group can be blocked in a facile manner utilizing o-methylaminobenzenthiol as a blocking group. Both of the 5' and the 3' -C-formyl groups can be deblocked with silver nitrate oxidation.

In an alternate method of 3'-C-formyl nucleoside synthesis, 1-O-methyl-3'-deoxy-3'-O-methylaminobenzene thiol-5'-O-trityl-β-D-erythro-pento furanoside can be used for its preparation. This compound then serves as a precursor for any 3'-deoxy-3'-C-formyl nucleoside. The 1-O-methyl-3'-deoxy-3'-O-methyl amino benzenethiol-5' -O-trityl-β-D-erythro-pentofuranoside is reacted with an appropriate base utilizing standard glycosylation conditions followed by deblocking to yield the nucleoside. In even a further alternate method, a 3'deoxy-3'-cyano nucleoside is prepared from either the corresponding 3' deoxy-3'-iodo nucleoside or via a glycosylation reaction with 1-O-methyl-3'-deoxy-3'-O-cyano-5'-O-trityl-β-D-erythro-pentofuranoside.

The 3"-O-amino-3"-hydroxymethyl nucleoside and the corresponding 5'-O-amino nucleoside can be conveniently prepared via a protected phthalimido intermediate via Mitsunobu conditions using N-hydroxyphthalimide, triphenylphosphine and diisopropylazodicarboxylate. This in turn is prepared by a Mitsunobu reaction on the unprotected hydroxyl group of the nucleoside. In forming the 3"-O-amino-3"-hydroxymethyl nucleoside, trityl serves as a blocking group for the 5'-hydroxyl group of the nucleoside. For both purine and pyrimidine nucleosides, prior to reacting with N-hydroxyphthalimide the 3'-hydroxy group is protected with TBDPS. With pyrimidine bases, in forming the 5'-O-amino nucleoside the 3'-hydroxyl can be protected with TBDPS blocking groups after introduction of the phthalimido on the 5' position.

A further procedure whereby inter-sugar linkages can be modified to provide phosphonate linked dinucleotides utilizes the Michaelis-Arbuzov procedure of Mazur et al., Tetrahedron, 20: 3949 (1984) for formation of 3'-C-phosphonate dimers. This procedure would utilize a 3'-hydroxymethyl nucleosides as synthon 1. This is treated with N-bromosuccinimide to yield the corresponding 3"-bromomethyl derivative. Synthon 2 is selected as a 5'-phosphite. Coupling of synthons 1 and 2 gives a dinucleoside coupled via a 3'-C-phosphonate linkage. The corresponding 5'-C-phosphonate dimers could be obtained by first reacting a suitable blocked phosphite with synthon 1 followed by deblocking to yield the 3'-$CH_2$-phosphite intermediate. Synthon 2 is selected as a 5'-bromonucleoside. The 3'-$CH_2$-phosphite intermediate is then reacted with synthon 2 to give the 5'-C-phosphate dimer. By selecting tribenzylphosphite as the blocked phosphite after coupling to synthon 1 the benzyl groups can be removed by hydrogenolysis. Alternately a 5'-deoxy-5'-bromonucleoside is reacted with a phosphite ester resulting in a 5'-phosphonate. This, in turn, is reacted with 3' -hydroxymethyl nucleoside to yield the 5'-C-phosphonate linked dimer.

Resulting dinucleosides from any of the above described methods, linked by hydrazines, hydroxyl amines and other linking groups of the inventions, can be protected by a dimethoxytrityl group at the 5'-hydroxyl and activated for coupling at the 3'-hydroxyl with cyanoethyldiisopropylphosphite moieties. These dimers can be inserted into any desired sequence by standard, solid phase, automated DNA synthesis utilizing phosphoramidite coupling chemistries. Therefore, the protected dinucleosides are linked with the units of a specified DNA sequence utilizing normal phosphodiester bonds. The resulting oligonucleotide analog or oligomer has a mixed backbone—part normal phosphodiester links and part novel four atoms links of the inventions. In this manner, a 15-mer, sequence-specific oligonucleotide can easily be synthesized to have seven hydroxylamine, hydrazine or other type linked dinucleosides. Such a structure will provide increased solubility in water compared to native phosphodiester linked oligonucleotides.

Oligonucleosides containing an uniform backbone linkage can be synthesized by use of CPG-solid support and standard nucleic acid synthesizing machines. i.e., Biosystems Inc. 380B and 394 and Milligen/Biosearch 7500 and 8800s. The initial nucleoside (number 1 at the 3'-terminus) is attached to a solid support such as controlled pore glass. Each new nucleoside is attached in sequence specific order either by manual manipulation or by the automated synthesizer system. In the case of a methylenehydrazine linkage, the repeating nucleoside unit can be 6f two general types, e.g., a nucleoside with a 5'-protected aldehydic function and a 3'-deoxy-3'-C-hydrazinomethyl group, or a nucleoside bearing a 5'-deoxy-5'-hydrazino group protected by an acid labile group and a 3'-deoxy-3'-C-formyl group. In each case, the conditions which are repeated for each cycle to add the subsequent sequence required base include: acid washing to remove the 5'-aldehydo protecting group; addition of the next nucleoside with a 3'-methylenehydrazino group to form the respective hydrazone connection; and reduction with any of a variety of agents to afford the desired methylenehydrazine linked CPG-bound oligonucleosides. One such useful reducing agent is sodium cyanoborohydride.

A preferred method is depicted in FIG. 1. This method employs a solid support on which a synthon 2 with a protected 5' site is bound. Preferably, the 5' site of said synthon can be protected with DMT. Thereafter, the 5' site of the synthon 2 is liberated with mild acid, washed, and oxidized to produce an intermediate product. In one preferred method, the aldehyde derivative reacts with N,N-diphenylethylene diamine to produce an intermediate product, 5'-diphenylimidazolidino protected synthon 2. In a more preferred method, the 5'-diphenylimidazolidino protected synthon 2 is directly loaded on the support. With either method, the intermediate product can be subsequently deblocked to provide a synthon 2 with a nucleophilic 5' position. Addition of a synthon 1 with a protected 5'-aldehyde group, such as a 5'-diphenylimidazolidino protected 3'-deoxy-3'-C-hydrazine base, can then react, such as by the addition of sodium cyanoborohydride, with the attached synthon 2. Following a wash, a dinucleoside linked through a hydrazino moiety is formed. Thereafter, the cycle can be repeated as desired by the addition of a synthon 1 species followed by acid/base deprotection to create a polysynthon—a resulting oligomer of a desired sequence—linked together through modified inter-sugar linkages. In some preferred embodiments of this invention, the synthon 1 species can be a 5'-DMT protected 3'-C-hydrazine base.

One preferred embodiment of this stepwise process utilizes a diphenylethyldiamine adduct (1,3-disubstituted imidazolidino) to protect the electrophilic center of synthon 2 during attachment to the solid support. Moffatt, J. G., et al., *Journal of American Chemical Society* 90: 5337–5338 (1968). Synthon 2 preferably can be attached to a solid support such as a controlled pore glass support or other suitable supports known to those skilled in the art. Attachment can take place via a standard procedure. Gait, M. J., ed., *Oligonucleotide Synthesis, A Practical Approach* (IRL Press 1984). Alternatively, preparation can occur by directly oxidizing the protected bound nucleoside with various standard oxidizing procedures. Bound synthon 2 is preferably reacted with hydrazine to produce a Schiff's base which can be subsequently reduced. Hydroxylamine is also a preferred reactant useful in this method.

Figure 2:
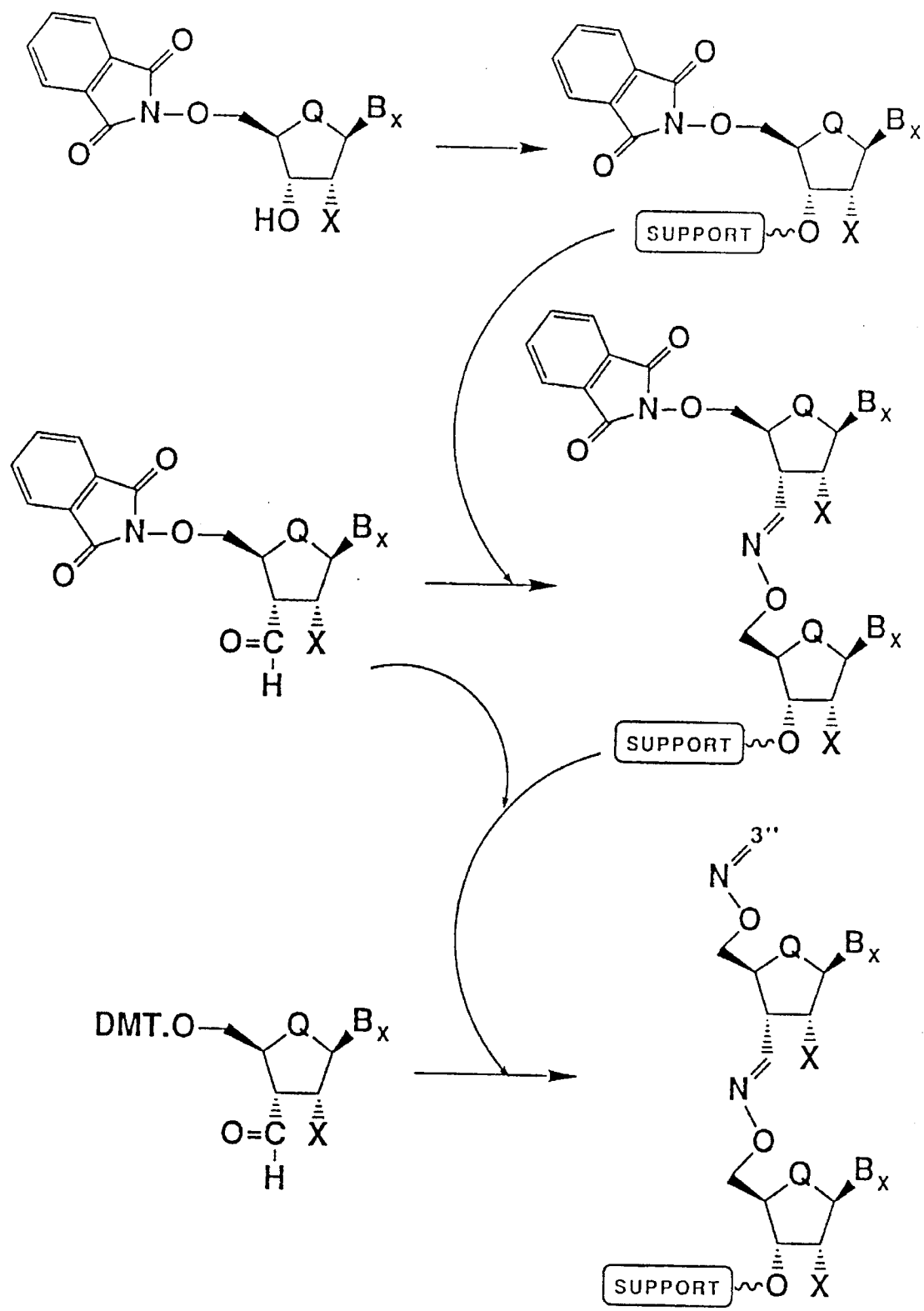
FIG. 2 is a schematic, synthetic scheme in accordance with further embodiments of the invention.

A further method of synthesizing uniform backbone linked oligonucleosides is depicted in FIG. 2. This method also employs a solid support on which a synthon 2, with a protected 5' site is bound. In this instance, the 5' site of the synthon is protected with a phthalimido group. Thereafter, the 5' site of the synthon 2 is liberated with methylhydrazine in DCM and washed with DCM:methanol. The aminohydroxyl group at the 5' position of synthon 1 is also protected with a phthalimido group. Such synthon 1 is a 5'-phthalimido protected 3'-deoxy-3'-C-formyl nucleoside. Synthon 1 is reacted with synthon 2 followed by deprotection at the 5' position and washing to liberate the next 5'-aminohydroxy reaction site. The cycle is repeated with the further addition of synthon 1 sufficient times until the desired sequence is constructed. Each nucleoside of this sequence is linked together with an oxime linkage. The terminal nucleoside of the desired oligonucleoside is added to the sequence as a 5'-DMT blocked 3'-deoxy-3'-C-formyl nucleoside. The oxime linked oligonucleoside can be removed from the support. If a aminohydroxyl linked oligonucleoside is desired the oxime linkages are reduced with sodium cyanoborohydride. Alternately, reduction can be accomplished while the oxime linked oligonucleoside is still connected to the support.

Also in accordance with this invention, nucleosides are provided having the structure:

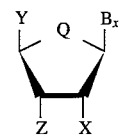

wherein $B_x$ is a variable base moiety; Q is O, $CH_2$, CHF or $CF_2$; X is H; OH; $C_1$ to $C_{10}$ lower alkyl, substituted lower alkyl, alkaryl or aralkyl; F; Cl; Br; CN; $CF_3$; $OCF_3$; OCN; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a group for improving the pharmacokinetic properties of an oligonucleotide; or a group for improving the pharmacodynamic properties of an oligonucleotide.

In such species, Y is hydroxyl, aminomethyl, hydrazinomethyl, hydroxymethyl, C-formyl, phthalimidohydroxymethyl, aryl-substituted imidazolidino, aminohydroxylmethyl, methylaminobenzenethio, methylphosphonate and methyl-alkyl phosphonate; and Z is H, hydroxyl, aminomethyl, hydrazinomethyl, hydroxymethyl, C-formyl, phthalimidohydroxymethyl; aryl substituted imidazolidino, aminohydroxylmethyl, ortho-methylaminobenzenethio, methylphosphonate or methyl alkylphosphonate.

All of the foregoing is with the proviso that when Q is O and Y is hydroxymethyl and X is H or OH then Z is not C-formyl; and when Q is O and X is H or OH and Z is hydroxyl then Y is not aminohydroxylmethyl, hydrazinomethyl or aryl-substituted imidazolidino.

The oligonucleotide analogs of this invention can be used in diagnostics, therapeutics, and as research reagents and kits. For therapeutic use the oligonucleotide analog is administered to an animal suffering from a disease modulated by some protein. It is preferred to administer to patients suspected of suffering from such a disease an amount of oligonucleotide analog that is effective to reduce the symptomology of that disease. One skilled in the art can determine optimum dosages and treatment schedules for such treatment regimens.

It is generally preferred to administer the therapeutic agents in accordance with this invention internally, such as orally, intravenously, or intramuscularly. Other forms of administration, such as transdermally, topically, or intralesionally can also be useful. Inclusion in suppositories can also be useful. Use of pharmacologically acceptable carriers is also preferred for some embodiments.

EXAMPLES

The following examples are illustrative, but not limiting, of the invention.

SYNTHESIS OF UNIFORM
METHYLENEHYDRAZINE (3'-$CH_2$—NH—NH—$CH_2$—5') LINKED
OLIGONUCLEOSIDES

EXAMPLE 1

Synthesis of CPG-bound nucleosides; diphenylimidazolidino protected 5'-aldehydic thymidine and 5'-deoxy-5'-hydrazino-thymidine.

CPG-bound thymidine (30 micromoles of thymidine on one gram of CPG support, ABI, Foster City, Calif.) is treated at ambient temperature with a mixture of DMSO, benzene, DCC, pyridine, and trifluoroacetic acid (15 ml/15 ml/2.48 g/0.4 ml/0.2 ml, similar to the oxidation procedure of Pfitzer, K. E. and J. G. Moffatt, *Journal of American Chemical Society* 85: 3027 (1963), to provide 5'-aldehydic nucleosides. The mixture is filtered after storing overnight. The support is washed with oxalic acid (1.3 g in 5 ml benzene/DMSO, 1 to 1) and treated with 1,2-dianilinoethylene (3.0 g) for one hour, filtered, and washed with acetonitrile to afford the 5'-diphenylimidazolidino protected 5'-aldehydic thymidine. Treatment of the support-bound 5'-aldehydo thymidine with a solution of hydrazine hydrate/sodium cyanoborohydrate in acetonitrile provides CPG-3'-bound 5'-deoxy-5'-hydrazino thymidine, which is stored as its hydrochloride salt.

EXAMPLE 2

Synthesis of 5'-diphenylimidazolidino protected-3'-deoxy-3'-C-hydrazinomethyl thymidine.

Commercially available 3'-O-acetylthymidine was oxidized and subsequently protected as its N,N-diphenylethylenediamine derivative (1,3-diphenylimidazolidino). This provides the known 5'-deoxy-5'-diphenylimidazolidino-3'-acetylthymidine. Pfitzer, K. E. and J. G. Moffatt, *Journal of American Chemical Society* 85: 3027 (1963). Hydrolysis of this material was achieved by methanolic ammonia treatment at ambient temperature for 15 hours. 5'-Deoxy-5'-diphenylimidazolidinothymidine (4.5 g) was dissolved in DMF (100 ml) and treated with triphenylmethyl phosphonium iodide at room temperature for 15 hours. The solvent was removed under reduced pressure and the resulting residue recrystallized from methanol to provide the 3'-deoxy-3'-iodo derivative.

The 3'-deoxy-3'-iodo-5'-diphenylimidazolino thymidine was dissolved in toluene and treated with hexamethylditin, t-butylisonitrile, and AIBN. This radical reaction provides the 3'-deoxy-3'-cyano derivative which was subsequently reduced with diisobutylaluminum hydride (DIBAL-H) in toluene/THF at 0° C., to afford 3'-deoxy-3'-C-formyl-5'-diphenylimidazolidino thymidine. This material was treated with hydrazine hydrate and sodium borohydride in acetonitrile to afford 5'-diphenylimidazolidino Protected-3'-deoxy-3'-C-hydrazinomethyl thymidine. The material is conveniently stored as the acetate salt.

EXAMPLE 3

Synthesis of uniform methylenehydrazine linked oligonucleosides via an Applied Biosystems Inc 380B DNA Synthesizer.

CPG-bound thymidine with a diphenylimidazolidino protected 5'-aldehyde that will become the 3'-terminal nucleoside is placed in an Applied Biosystems, Inc. (ABI) column (250 mg, 10 micromoles of bound nucleoside) and attached to an ABI 380B automated DNA Synthesizer. The automated (computer controlled) steps of a cycle that are required to couple a desmethyl nucleoside unit to the growing chain are as follows.

| STEP | REAGENT OR SOLVENT MIXTURE | TIME (min:sec) |
|---|---|---|
| 1 | 3% DCA in dichloroethane | 3:00 |
| 2 | Dichloroethane wash | 1:30 |
| 3 | 5'-Deoxy-(1,3-diphenylimidazolidino)-3'-deoxy-3'-C-methylene hydrazine nucleoside (the second nucleoside); 20 micromoles in 30 ml of acetonitrile | 2:50 |
| 4 | Sodium borohydride (50 micromole in 1:1 THF/EtOH, 50 ml) | 3:00 |
| 5 | Dichloroethane wash | 2:00 |
| 6 | Recycle starting at step 1 (acid wash) | 3:00 |

This procedure yields as its product nucleoside the 5'-dimethyoxy trityl substituted nucleoside unit.

At the completion of the synthesis, base deprotection and oligomer removal from the support is accomplished by standard procedures. Trityl-on HPLC purification followed by acetic acid deprotection and precipitation provides the oligonucleosides as the acetate salts.

SYNTHESIS OF INTERMITTENT METHYLENEHYDRAZINE (3'-CH$_2$—NH—NH—CH$_2$—5')LINKED OLIGONUCLEOSIDES

EXAMPLE 4

Synthesis of 5'-Deox-7-5'-hydrazinothymidine Hydrochloride

To provide 5'-Benzylcarbazyl-5'-deoxythymidine, 5'-O-tosylthymidine, *Nucleosides & Nucleotides* 9: 89 (1990) (1.98 g, 5 mmol), benzylcarbazide (4.15 g, 25 mmol), activated molecular sieves (3 A, 2 g), and anhydrous dimethyl-acetamide (100 ml) were stirred together with exclusion of moisture at 110° C. (bath temperature) for 16 hours. The products were cooled and concentrated under reduced pressure (bath temperature <50° C.). The residue was purified on a silica gel column (5×45 cm) with CH$_2$Cl$_2$/MeOH (9:1, vol/vol) as the solvent. The homogeneous fractions were pooled, evaporated to dryness and the foam recrystalized from EtOH to yield 0.7 g (36%) of 5'-benzylcarbazyl-5'-deoxythymidine; mp 201° C.; $^1$H NMR (Me$_2$SO-d$_6$) δ1.79 (s, 3, CH$_3$), 2.00–2.18 (m, 2, C$_2$, CH$_2$), 2.95 (t, 2, C$_5$,CH$_2$), 3.75 (m, 1, C$_4$,H), 4.18 (m, 1, C$_3$,H), 4.7 (brs, 1, O$_2$NH), 5.03 (s, 2, PhCH$_2$), 5.2 (d, 1, C$_3$,H), 6.16 (t, 1, C$_1$,H), 7.2–7.4 (m, 5, C$_6$H$_5$), 7.6 (s, 1, C$_6$H), 8.7 (brs, 1, CH$_2$NH), 11.2 (brs, 1, C$_3$NH).

To provide the hydrochloride salt of 5-'-deoxy-5'-hydrazinothymidine as a hygroscopic powder, a mixture of the above carbazate (0.78 g, 2 mmol) and palladium on charcoal (10%, 150 mg) in anhydrous MeOH/HCl (30 ml, 2%, HCl by weight) was stirred under an atmosphere of hydrogen at room temperature for 1.5 hours. The methanolic solution was filtered through Celite to remove the catalyst. The filter cake was washed with EtOH (2×25 ml). The filtrate was concentrated under vacuum and the residue was dried overnight to remove traces of HCl. The yellow residue was dissolved in methanol (3 ml) and added dropwise to a rapidly stirred solution of ethyl acetate (150 ml). The filtered precipitate was washed with ethyl acetate (3×100 ml) and the pale yellow solid was dried under vacuum to yield 0.51 g (88%) of 5'-deoxy-5'-hydrazinothymidine hydrochloride (hygroscopic powder); $^1$H NMR (Me$_2$SO-d$_6$) δ1.81 (s, 3, CH$_3$), 2.02–2.22 (m, 2, C$_2$,CH$_2$), 3.2 (m, 2, C$_5$,CH$_2$), 3.8, (m, 1, $C_4$,H), 4.2 (m, 1, $C_3$,H), 6.17 (t, 1, $C_1$,H), 7.54 (s, 1, $C_6$H), 11.18 (brs, 1, $C_3$NH), the hydrazino and 3'-OH were not seen because the sample was wet.

EXAMPLE 5

Synthesis of 5'-Trityl-1-[2,3-dideoxy-3-C-(formyl)-β-D-erythro-pentofuranosyl]uracil and thymine To a stirred solution of 3'-cyano-2',3'-dideoxy-5' -O-trityl uridine (0.96 g, 2 mmol), (see *Tetrahedron Letters* 29: 2995 (1988) for synthesis of the thymidine analog) in dry THF (20 ml) under argon was added a solution of DIBAL-H in toluene (Aldrich) (1M, 4 ml) at −10° C. over a period of 10 min. After 30 mins the reaction was quenched with MeOH (5 ml) at −10° C. The mixture was further stirred at ambient temperature for 30 mins and diluted with $CH_2Cl_2$ (25 ml) before concentrating under vacuum. This process was repeated with $CH_2Cl_2$ (3×25 ml) in order to remove the residual THF. The residue was purified by flash chromatography on silica gel (25 g). Elution with $CH_2Cl_2$ (9:1, v/v) and crystallization from $CH_2Cl_2$/MeOH gave 5' -O-trityl-3'-C-formyl-2',3'-dideoxyuridine (0.53 g, 53%); mp 100° C.; $^1$H NMR ($CDCl_3$) δ2.25–2.8 (m, 2, $CH_2$), 3.4 (m, 1, $C_3$,H), 3.45–3.6 (m, 2, $C_5$,$CH_2$), 4.37 (m, 1, $C_4$, H), 5.4 (d, 1, $C_5$H), 6.1 (m, 1, $C_1$,H), 7.2–7.4 (m, 15, $C_6H_5$), 7.81 (d, 1, $C_6$H), 7.95 (brs, 1, NH), 9.61 (s, 1, HC=O).

EXAMPLE 6

Synthesis of 1-Methyl-5-(t-butyldiphenylsilyl)-2,3-dideoxy-3-C-(formyl)-D-erythropentofuranose The 3'-C-formyl sugar precursor was obtained as an oil in 90% yield using the DIBAL-H reduction for the 3'-C-cyanosugar, *Tetrahedron Letters* 44: 625 (1988), described above.

EXAMPLE 7

Synthesis of Methylenehydrazine Linked (3'-$CH_2$—NH—NH—$CH_2$—5') 5'-Dimethoxytrityl-3'-β-cyanoethoxydiisopropylphosphoramidite Dinucleosides To a stirred solution of 5'-O-trityl-1-[2,3-dideoxy-3-C-(formyl)-β-D-erythro-pentofuranosyl] thymine (1 mmol), '-deoxy-5'-hydrazinothymidine hydrochloride (1, mmol), and dry THF (25 ml) under argon was added dried molecular sieves (1 g). The reaction was allowed to proceed overnight and then was treated with bromocresol green (5 mg). Sodium cyanoborohydride (4 mmol) was then added, followed by dropwise addition via syringe of p-toluenesulfonic acid in THF (4 mmol in 4 ml) in such a way that the tan color of the reaction mixture was maintained. Stirring was continued for two hours after the addition. The mixture was filtered and the solids were washed with dry MeOH (3×10 ml). The combined filtrates were pooled and concentrated. The residue was purified by column chromatography to afford methylenehydrazine linked (3'—$CH_2$—NH—NH—$CH_2$—5') thymidine dimers. The hydrazino linkage of this material was monobenzoylated via the transient method described in Gait, M. J., ed., *Oligonucleotide Synthesis, A Practical Approach* (IRL Press 1984). The 5'-hydroxyl and 3'-hydroxyl are converted to the 5'-O-dimethoxytrityl-3'-β-cyanoethoxydiisopropylphosphoramidite according to standard procedures.

EXAMPLE 8

Synthesis of Intermittent Methylenehydrazine (3'-$CH_2$—NH—NH—$CH_2$—5') Linked Oligonucleosides CPG-bound thymidine (or any other nucleoside that is to become the 3'-terminal base) is placed in an Applied Biosystems, Inc. (ABI) column (250 mg, 10 micromoles of bound nucleoside) and attached to an ABI 380B automated DNA Synthesizer. The standard, automated (computer controlled) steps utilizing phosphoramidite chemistries are employed to place the methylenehydrazine thymidine dimer into the sequence at any desired location.

EXAMPLE 9

Alternate synthesis of 5'-O-trityl-1-[2,3-dideoxy-3-C(formyl)-β-D-erythro-pentofuranosyl]-uracil and -thymine A mixture of 3'-deoxy-3'-iodo-5'-O-tritylthymidine (0.59 g, 4 mmol); *Tet. Letters*, 29: 2995 (1988), tris(trimethylsilyl) silane (2.87 g, 1.2 mmol), AIBN (12 mg, 0.072 mmol), and toluene (20 ml) were mixed in a glass container and saturated with argon (bubbling at room temperature). The glass vessel was inserted into a stainless steel pressure reactor, pressurized with carbon monoxide (80 psi), closed, and heated (90° C., bath) for 26 hrs. The reaction mixture was cooled (0° C.) and CO was allowed to escape carefully (under the fume hood). The product was purified by flash column chromatography on silica gel (20 g). Elution with EtOAc:Hexanes (2:1, v/v) and pooling the appropriate fractions furnished 0.30 g (61%) of the title compound as a foam.

A radical carbonylation of 2',3'-dideoxy-3'-iodo-5' -O-trityluridine in a similar manner gives the 3'-C-formyl uridine derivative.

EXAMPLE 10

Synthesis of 5'-O-phthalimidothymidine and 2'-deoxy-5'-O-phthalimidouridine

To a stirred mixture of thymidine (1.21 g, 5 mmol), N-hydroxyphthalimide (1.09 g, 6.6 mmol), triphenylphosphine (1.75 g, 6.6 mmol), in dry DMF (25 ml) was added diisopropylazodicarboxylate (1.5 ml, 7.5 mmol) over a period of 30 min at 0° C. The stirring was continued for 12 hrs at room temperature. The solvent was evaporated under vacuo and the residue washed with diethyl ether (2×50 ml). The residue was suspended in hot EtOH (50 ml), cooled and filtered to furnish 1.54 g (80%) of the title compound as a white powder.

An analogous reaction on 2'-deoxyuridine gave the corresponding 2'-deoxy-5'-phthalimidouridine; mp 241°–242° C.

EXAMPLE 11

Synthesis of 5'-O-Phthalimido-3'-O-tert-butyl(diphenyl)-silylthlmidine and 2'-deoxy-5'-O-phthalimido-3'-O-tert-butyl(diphenyl)silyluridine Treatment of 5'-O-phthalimidothymidine or 2'-deoxy-5'-O-phthalimidouridine with tert-butyl(diphenyl)chlorosilane in pyridine and imidazole in a standard manner afforded 5'-O-Phthalimido-3'-O-tert-butyl(diphenyl)silylthymidine and 2'-deoxy-5'-O-phthalimido-3'-O-tert-butyl(diphenyl)silyluridine as crystalline products. $^1$H NMR of the thymidine derivative in $CDCl_3$: δ1.10 (s, 9, $C(CH_3)_3$), 1.95 (s, 3, $CH_3$), 2.2 (m, 2, $C_2$, $CH_2$), 3.63–4.15 (m, 3, $C_3$, H and $C_5$, $CH_2$), 4.80 (m, 1, $C_4$, H), 6.45 (t, 1, $C_1$, H), 7.4 (m, 15, ArH, $C_6$H), 8.2 (br s, 1, NH).

EXAMPLE 12

Synthesis of 5'-O-amino-3'-O-tert-butyl(diphenyl)silylthymidine

To a stirred mixture of 5'-O-phthalimido-3'-O-tert-butyl-(diphenyl)silylthymidine in dry $CH_2Cl_2$ (10 ml) was added methylhydrazine (3 mmol) under anhydrous conditions at room temperature. The solution was stirred for 12 hrs, cooled (0° C.) and filtered. The precipitate was washed with $CH_2Cl_2$ (2×10 ml) and combined filtrates were concentrated. The residue was purified by flash column chromatography (silica gel, 20 g). Elution with $CH_2Cl_2$:MeOH (9:1, v/v) furnished the desired 5'-O-amino-3'-O-tert-butyl(diphenyl)silylthymidine as a crystalline product (65%): $^1H$ NMR ($CDCl_3$) δ1.0 (s, 9, $C(CH_3)_3$), 1.80 (s, 3, $CH_3$), 1.81 and 2.24 (2 m, 2, $C_2$, $CH_2$), 3.25 and 3.60 (2 m, 2, $C_5$, $CH_2$), 4.0 (m, 1, $C_3$, H), 4.25 (m, 1, $C_4$, H), 5.4 (v br, s, $NH_2$), 6.25 (t, 1, $C_1$, H), 7.2 (s, 1, $C_6H$), 7.25–7.60 (m, 10, ArH), 8.4 (br s, 1, NH).

EXAMPLE 13

Synthesis of (3'-CH=N—O—$CH_2$—5') and (3'—$CH_2$—NH—O—$CH_2$—5') linked oligonucleosides A mixture of 3'-deoxy-3'-C-formyl-5'-O-tritylthymidine (0.99 g, 2 mmol), and 5'-O-amino-3'-O-tert-butyl(diphenyl)silylthymidine (0.99 g, 2 mmol) in dry $CH_2Cl_2$ (25 ml) was stirred for 1 hr at room temperature. The solvent was evaporated under vacuo and the residue dissolved in dry THF (20 ml). A THF solution of tetrabutylammonium fluoride (1M, 5 ml) was added to the stirred reaction mixture. The stirring was continued for 1 hr at room temperature, and the solvent evaporated to furnish a gummy residue. The residue was purified by short silica gel (20 g) column chromatography, and on elution with $CH_2Cl_2$:MeOH (99:4, v/v) furnished the desired dimer as a foam. The product was dissolved in anhydrous MeOH (50 ml) and to this a saturated methanolic HCl solution (2.5 ml) was added. The reaction mixture was stirred at room temperature for 15 hrs. Anhydrous pyridine (10 ml) was added to the above solution and the solvents evaporated to furnish the crude oxime linked dinucleoside. The oxime was purified by silica gel (20 g) column chromatography. Elution with $CH_2Cl_2$:MeOH (92:8, v/v) furnished 0.69 g (70%) of the oxime linked dimer as a mixture of E/Z isomers. $^1H$ NMR (DMSO-$d_6$) δ1.78 and 1.80 (2 s, 6H, 2 $CH_3$), 2.02–2.40 (m, 4, $2C_2$, $CH_2$), 3.15 (m, 1, $C_3$, H), 3.45 and 3.65 (2 m, 2, $C_5$, $CH_2$), 3.95 (m, 2, 2 $C_4$, H), 4.15–4.25 (m, 3, $C_3$, H, and $C_5$, $CH_2$), 5.20 (t, 1, $_5$,OH), 5.40 (d, 1, $_3$,OH) 6.05 (t, 1, $C_1$, H), 6.18 (t, 1, $C_1$, H), 6.85 (d, 1, $C_3$,,H), 7.4 and 7.44 (2 s, 1, $C_6H$), 7.46 (d, 1, $C_3$,,H), 7.78 and 7.80 (2 s, 1, $C_6H$) and 11.25 (2 br s, 2, NH).

The two geometrical isomers (E/Z) were separated by reverse phase HPLC and fully characterized by various analytical techniques. The isomeric dimer was further converted to its 5'-O-dimethoxytrityl derivative at the 5'-hydroxyl group of the dimer and its 3'-O-β-cyanoethoxydiisopropylphosphoramidite derivative at the 3'-hydroxyl group of the dimer, utilizing standard chemistry. $^{31}P$ NMR of this derivatized dimer in DMSO-$d_6$ resonated at δ 150.4, 150.7 and 150.8 ppm. The protected dimer can be conveniently stored and used for coupling utilizing an automated DNA synthesizer (ABI 380B) as and when required for specific incorporation into oligomers of therapeutic value. As is shown below, an oligomer bearing an oxime linked nucleoside dimer is reduced to an oligomer bearing a corresponding hydroxylamine linked nucleoside dimer.

EXAMPLE 14

Synthesis of Intermittent (3'—CH=N—O—$CH_2$—5') or (3'—$CH_2$—NH—O—$CH_2$—5') linked Oligonucleosides An appropriate 2'-deoxynucleoside that will become the 3'-terminal nucleoside of an oligonucleoside is bound to a CPG column for use on an ABI 380B automated DNA synthesizer. Standard phosphoramidite chemistry program steps were employed to place the dimer bearing the (3'—CH=N—O—$CH_2$—5') or (3'—$CH_2$—NH—O—$CH_2$—5') linkages into the desired position or positions of choice within the sequence.

EXAMPLE 15

Synthesis of uniform (3'—CH=N—O—$CH_2$—5') or (3'—$CH_2$—NH—O—$CH_2$—5') linked oligonucleosides via an ABI 380B DNA synthesizer, utilizing 3 nucleoside subunits.

Subunit 1: CPG-bound 5'-O-phthalimidothymidine was prepared according to the procedure of *Nucleic Acids Research*, 18: 3813 (1990), and used as a 3'-terminal unit for oligonucleoside synthesis.

Subunit 2: A bifunctional (3'-C-formyl and 5'-O-phthalimido deoxyribonucleoside) is derived by standard glycosylation of methyl 2,3-dideoxy-3-cyano-5-O-(phthalimido)-β-D-erythro-pentofuranoside with an appropriate base and DIBAL-H reduction of the nucleoside product.

Subunit 3: A 5'-O-DMT-3'-C-formyl thymidine is employed for the incorporation of the last (the 5'-end of the oligonucleoside) nucleoside.

The automated steps of a cycle that is required to synthesize a uniform linkage (on a 10 μM scale: loading of unit 1 on CPG) are as follows:

| STEP | REAGENT/SOLVENT | Time/min |
|---|---|---|
| 1 | 5% Methylhydrazine in DCM | 10 |
| 2 | DCM:MeOH (9:1, v/v) | 5 |
| 3 | DCM wash | 2 |
| 4 | 3'-C-formyl-5'-O-phthalimido-deoxyribo nucleoside (Unit 2, 20 μM, in 20 ml of DCM) | 3 |
| 5 | DCM:Acetone (9:1, v/v): Capping | 2 |
| 6 | DCM wash | 3 |
| Foregoing steps 1 through 6 are repeated for each addition of a nucleoside unit depending on desired sequence and length. The final unit is then added: | | |
| 8 | Final nucleoside (20 μM in 20 ml DCM) or Unit 3 | 5 |

$NaCNBH_3$ REDUCTION STEP FOR CONVERSION OF (3'—CH=N—O—$CH_2$—5') LINKAGE TO (3'—$CH_2$—NH—O—$CH_2$—5') IN A DIMER LINKAGE OR LINKAGES OF AN OLIGONUCLEOSIDE

EXAMPLE 16

Reduction of a Dimer

To a solution of a dimer (0.49 g, 1 mmol) in glacial acetic acid (AcOH) (5 ml) was added sodium cyanoborohydride (0.19, 3 mmol) in AcOH (1 ml), under an argon atmosphere at room temperature. The suspension was stirred for 1 hr, and an additional amount of $NaBH_3CN$ in AcOH (1 ml) was added and stirring continued for 1 hr. The excess of AcOH was removed under reduced pressure at room temperature. The residue was coevaporated with toluene (2×50 ml) and purified by silica gel (25 g) column chromatography. Elution with $CH_2Cl_2$:MeOH (9:1, v/v) and pooling of appropriate fractions, followed by evaporation furnished 0.36 g (75%) of crystalline dimer.

EXAMPLE 17

Reduction of an Oligonucleoside

CPG-bound oligonucleoside (1 µM), that contains one (or more) backbone modified linkages is taken off the DNA synthesizer after completion of its synthesis cycles. A 1.0M $NaBH_3CN$ solution in THF:AcOH (10 ml, 1:1 v/v) is pumped through the CPG-bound material in a standard way utilizing a syringe technique for 30 min. The column is washed with THF (50 ml), and reduced oligonucleoside is generated from the support column in a standard way.

EXAMPLE 18

Alternative Reduction of an Oligonucleoside

As an alternative to the above reduction, reduction can also be accomplished after removal from the CPG support. At the completion of synthesis the oligonucleoside is removed from the CPG-support by standard procedures. The 5'-O-trityl-on oligonucleoside is purified by HPLC and then reduced by the $NaBH_3CN/AcOH/THF$ method as described above.

EXAMPLE 19

Synthesis of (3'—$CH_2$—O—N=CH—5') and (3'—$CH_2$—NH—$CH_2$—5') Linked Oligonucleosides 3'-C-formyl-5'-O-tritylthymidine was reduced with an excess of $NaBH_4$ to furnish 3'-hydroxymethylthymidine which on treatment with triphenylphosphine, N-hydroxyphthalimide and diisopropylazodicarboxylate in THF furnished 3'-phthalimidomethyl analog which upon hydrazinolysis using methylhydrazine gave 3'-hydroxymethyl-(O-amino)-5'-O-tritylthymidine in an overall yield of 64%.

1-(4-C-formyl-3-O-tert-butyl(diphenyl)silyl-2-deoxy-β-D-erythro-pentofuranosyl)thymidine was prepared as per the procedure of *Nucleosides and Nucleotides*, 9:533 (1990). The coupling of this nucleoside with 3'-hydroxymethyl-(O-amino)-5'-O-tritylthymidine in DCM as described above gave the oxime which on $NaCNBH_3CN$ reduction gave the dimer. The dimer is suitably protected and activated as the 5'O-DMT and 3'-O-phosphoramide derivative for insertion into desired locations of oligonucleosides by standard DNA synthesizer chemistry.

EXAMPLE 20

Synthesis of (3'—$CH_2$—$P(O)_2$—O—$CH_2$—5') and (3'—$CH_2$—O—$P(O)_2$—$CH_2$5') Linked Oligonucleosides A. Synthesis of 3'-C-phosphonate dimer 3'-hydroxymethyl-5'-(O-tert-butyl(diphenyl)silyl)thymidine is converted into its bromide by treatment with NBS. The bromide is subjected to an Arbuzov reaction to furnish the phosphor, ate diester. Cleavage of the phosphonate diester with trimethylbromosilane gives the free acid which on treatment with 3'-(O-tert-butyl(diphenyl)silyl)thymidine and DCC in pyridine yields the dimer.

B. Synthesis of 3'-C-phosphonate linked Oligonucleosides

The above dimer can be incorporated into an oligonucleoside by suitably protecting and activating the dimer as the 5'O-DMT and 3'-O-phosphoramide derivative for insertion into desired locations in oligonucleosides by standard DNA synthesizer chemistry.

C. Synthesis of 5'-C-phosphonate linked Oligonucleosides

The corresponding 5'-C-phosphonate dimers could be obtained by a reacting a 5'-deoxy-5'-bromonucleoside with a phosphite ester, resulting in a 5'-phosphonate. This in turn is reacted with a 3'-hydroxymethyl nucleoside to yield the 5'-C-phosphonate linked dimer.

EXAMPLE 21

Synthesis of Compound (13), Structure (III) wherein $R_{E1}$ is O-(dimethoxytrityl), $R_{E2}$ is O-(2-cyanoethyl- N,N,N',N'-tetraisopropyl phosphordiamidyl), and $R_{E3}$ is H.

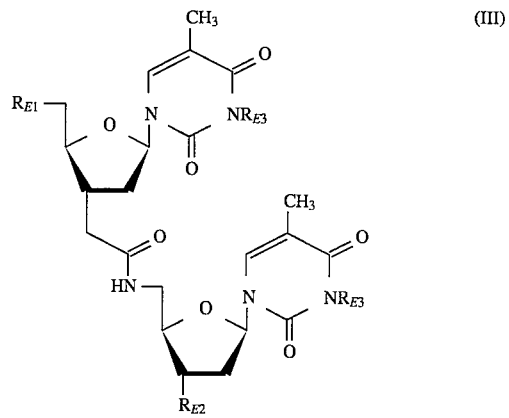

(III)

A. Compound (2), Structure (IV) wherein $R_{E1}$ is O-(t-butyldiphenylsilyl), $R_{E2}$ is O-(p-toluene thioformyl), and $R_{E3}$ is H.

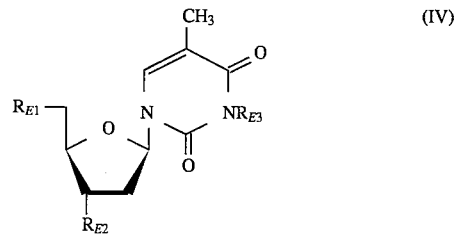

(IV)

Compound (1) [structure (IV) wherein $R_{E1}$=O-t-butyldiphenylsilyl, $R_{E2}$=OH, $R_{E3}$=H; 11.45 g; 23.82×10$^{-3}$ mole] is dissolved under argon in $CH_2Cl_2$ (100 ml). To this solution is added $NEt_3$ (2.41 g; 23.82.10$^{-3}$ mole), DMAP (4-N,N-dimethylamino pyridine; 2.911 g; 23.82×10$^{-3}$ mole), and p-toluene thiochloroformate (4.446 gr.; 23.82× 10$^{-3}$ mole). After 20 hours of stirring at room temperature, the mixture is diluted with $CH_2Cl_2$ (50 ml), washed with aq. $NaH_2PO_4$ (2×50 ml) then with brine (2×50 ml), and dried over $Na_2SO_4$. After evaporation of the solvent, the residue is chromatographed on silica gel (Hexane:AcOEt, 4: 1). Compound (2) is isolated as a pale yellow solid (13.074 g; 20.72×10$^{-3}$ mole; 87%). $^1$H-NMR (CDCl$_3$, 500 MHz, δ(ppm), J(Hz)): 2.41 ($H_{2''}$, ddd, $^2J$=13.5, $^3J_{2'\text{-}3}$=5.9; $^3J_{2'\text{-}1}$= 9.3); 2.73 ($H_{2'}$, dd, $^3J_{2'\text{-}1}$=5.0); 4.36 ($H_{4'}$, ddd, $^3J_{3'\text{-}4'}$=0.9); 5.94 ($H_{2'}$, dd); 6.51 ($H_{1'}$,dd); 7.58 ($H_6$, q, $^4J$=1.0) MS (FD: m/e): 631 (M$^+$).

B. Compound (3), Structure (IV) wherein $R_{E1}$ is O-(t-butyldiphenylsilyl), $R_{E2}$ is allyl, and $R_{E3}$ is H.

Compound (2) (5.0 g; 7.926×10$^{-3}$ mole) is dissolved under argon in degassed benzene (79 ml: 0.1M; degassed with a stream of argon for 30 minutes). After addition of allyl tri-n-butyltin (13.12 g; 39.63×10$^{-3}$ mole) and AIBN (azo-bis isobutyronitrile; 0.65 g; 3.963×10$^{-3}$ mole), the mixture is heated under reflux. After 4 hours, AIBN (0.26 g; 1.58×10$^{-3}$ mole) is added again. No starting material is detected after 20 hours by analytical thin-layer chromatography (silica gel; Hexane:AcOEt, 1:1). The solvent is evaporated under reduced pressure and the residue is chromatographed on silica gel (Hexane:AcOEt, gradient 6:1→2:1). Compound (3) is isolated as a white solid (3.12 g; 6.18×10$^{-3}$ mole; 78%). $^1$H-NMR (CDCl$_3$, 500 MHz, δ (ppm), J(Hz)): 2.15–2.19 (2H$_{2'}$, m); 2.46 (H$_{3'}$, m); 5.70 (CH=CH$_2$; m); 6.11 (H$_{1'}$, dd $^3$J$_{1'\text{-}2}$=5.1 and 6.1); 7.51 (H$_6$, q, $^4$J=1.1). MS(FD; m/e): 505 (M$^+$).

C. Compound (4), Structure (IV) wherein R$_{E1}$ is O-(t-butyldiphenylsilyl), R$_{E2}$ is CH$_2$C(O)H, and R$_{E3}$ is H.

Olefinic derivative (3) (3.11 g; 6.162×10$^{-3}$ mole) is dissolved in a mixture of 2:1 dioxane-H$_2$O (60 ml). OsO$_4$ (0.157 g; 0.616×10$^{-3}$ mole) is added, followed by a solution of NaIO$_4$ (2.89 g; 13.55×10$^{-3}$ mole) in H$_2$O (25 ml). The suspension is stirred at room temperature for 4 hours. CH$_2$Cl$_2$ then is added (100 ml). The organic phase is washed with brine (2×50 ml) and dried over Na$_2$SO$_4$. After evaporation of the solvent, the residue is chromatographed on silica-gel (Hexane:AcOEt, 1:1). Compound (4) is obtained as a pale yellow solid (1.561 g; 3.08×10$^{-3}$ mole; 50%. $^1$H-NMR (CDCl$_3$, 500 MHz, δ(ppm), J(Hz)): 2.07 (H$_{2'}$, ddd, $^2$J=14.9, $^3$J$_{2'\text{-}1}$=7.0, $^3$J$_{2'\text{-}3}$=7.9); 2.39 (H$_{2'}$, ddd, $^3$J$_{2'\text{-}1}$=3J= 4.9, $^3$J$_{2'\text{-}3}$=8.3); 2.84 (H$_{3'}$, m); 3.72 (H$_{4'}$, ddd, $^3$J$_{3'\text{-}4'}$=7.5); 6.14 (H$_{1'}$, dd); 9.72 (CHO; dd).

D. Compound (5), Structure (IV) wherein R$_{E1}$ is O-(t-butyldiphenylsilyl), R$_{E2}$ is CH$_2$C(O)OCH$_3$, and R$_{E3}$ is H.

Aldehyde (4) (2.23 g; 4.401×10$^{-3}$ mole) is dissolved in DMF (20 ml). MeOH (0.846 g; 26.40×10$^{-3}$ mole) and PDC (pyridinium dichromate; 10.137 g; 26.40×10$^{-3}$ mole) are added. The resulting dark brown solution is stirred at room temperature for 20 hours, then diluted with CH$_2$Cl$_2$ (60 ml), and washed with NaH$_2$PO$_4$ (2×50 ml) and with brine (2×50 ml). After drying over Na$_2$SO$_4$, the solvent is evaporated and the residue is chromatographed on silica gel (Hexane:AcOEt, 2:1). Compound (5) (1.531 g; 2.869×10$^{-3}$ mole; 65%) is isolated as a white solid. $^1$H-NMR (CDCl$_3$, 500 MHz, δ (ppm), J(Hz)): 2.17 (H$_{2'}$, ddd, $^2$J=14.3, $^3$J$_{2'\text{-}1}$=7.0, $^3$J$_{2'\text{-}3}$= 7.2); 2 33 (H$_{2'}$, ddd, $^3$J$_{2'\text{-}1}$=5.0, $^3$J$_{2'\text{-}3}$=8.3); 2.82 (H$_{3'}$, m); 3.68 (COOMe, s); 6.15 (H$_1$', dd).

E. Compound (6), Structure (IV) wherein R$_{E1}$ is O-(t-butyldiphenylsilyl), R$_{E2}$ is CH$_2$C(O)OH, and R$_{E3}$ is H.

Ester derivative (5) (7.197 g; 13.4×10$^{-3}$ mole) is dissolved in a 1:1 mixture of THF-H$_2$O (50 ml). A solution of NaOH 0.1N (26.8 ml; 26.81×10$^{-3}$ mole) is added. After 18 hours of stirring at room temperature, an additional amount of 0.1N NaOH (13.4 ml; 13.4×10$^{-3}$ mole) is introduced and the mixture is stirred for 2 hours, neutralized with HCl 1N, and extracted with CH$_2$Cl$_2$ (2×50 ml). The organic phase is washed with brine (2×50 ml) and dried over Na$_2$SO$_4$. After evaporation of the solvent, compound (6) is obtained as a white solid (6.38 g; 16.03×10$^{-3}$ mole; 91%). $^1$H-NMR (CDCl$_3$, 250 MHz, δ(ppm)): 6.14 (H$_{1'}$, dd).

F. 5'-Azido-2',5'-dideoxy-thymidine (7), Structure (IV) wherein R$_{E1}$ is azido, R$_{E2}$ is hydroxl, and R$_{E3}$ is H.

The synthesis of compound (7) was accomplished according to a procedure described by T. Lin, W. Prusoff, *J. Med. Chem.*, 21, 109 (1978) from the commercially available pyrimidine thymidine (Aldrich Chemical Co., Milwaukee, Wis.).

G. Compound (S), Structure (IV) wherein R$_{E1}$ is azido, R$_{E2}$ is O-(t-butyldiphenylsilyl), and R$_{E3}$ is H.

Compound (7) (3.0 g; 11.22×10$^{-3}$ mole) is dissolved under argon in DMF (20 ml). Imidazole (1.3 g; 19.08×10$^{-3}$ mole) and t-butyl diphenyl chlorosilane (4.627 g; 16.83×10$^{-3}$ mole) are added. The mixture is stirred 48 hours at room temperature. The DMF is evaporated under reduced pressure and the residue is dissolved in CH$_2$Cl$_2$ (60 ml) and NaH$_2$PO$_4$ aq. (60 ml). The organic phase is washed with NaH$_2$PO$_4$ aq. (50 ml) and with brine (50 ml) and is dried over Na$_2$SO$_4$. After evaporation of the solvent, the remaining material is chromatographed on silica gel (CHCl$_3$:MeOH 20:1). Compound (8) is obtained as a pale yellow oil (5.39 g; 10.66× 10$^{-3}$ mole; 95%). $^1$H-NMR (CDCl$^3$, 250 MHz, δ (ppm), J(Hz)): 1.95 (H$_{2'}$, ddd); 2.36 (H$_{2'}$, ddd); 6.38 (H$_{1'}$, dd).

H. Compound (9), Structure (IV) wherein R$_{E1}$ is amino, R$_{E2}$ is O-(t-butyldiphenylsilyl), and R$_{E3}$ is H.

Compound (8) (7.3 g; 14.43×10$^{-3}$ mole) is dissolved in degassed benzene (144 ml; 0.1M; degassed with a stream of argon for 30 minutes). After addition of AIBN (0.237 g; 1.44×10$^{-3}$ mole) and n-tributyltin hydride (9.244 g; 31.76× 10$^{-3}$ mole), the solution is heated at 80° C. for 15 hours. An additional amount of AIBN (0.237 g; 1.44×10$^{-3}$ mole) is introduced and the heating is continued for 5 hours. The solvent is evaporated and the residue is chromatographed on silica gel (Hexane:AcOEt 1:2). Compound (9) is obtained as a pale yellow solid (4.605 g; 9.6×10$^{-3}$ mole; 85%). $^1$H-NMR (CDCl$_3$, 500 MHz, δ (ppm), J(Hz)): 1.93 (H$_{2'}$, ddd, $^2$J=13.5, $^3$J$_{2'\text{-}1}$=6.8); 2.35 (H$_{2'}$, ddd, $^3$J$_{2'\text{-}1}$=6.2, $^3$J$_{2'\text{-}3}$=4.2); 3.87 (H$_{4'}$, ddd, $^3$J$_{3'\text{-}4}$=3.7); 4.25 (H$_{3'}$, ddd); 6.31 (H$_{1'}$, dd).

I. Compound (10), Structure (Ill) wherein R$_{E1}$ is O-(t-butyldiphenylsilyl), R$_{E2}$ is (O-t-butyldiphenylsilyl), and R$_{E3}$ is H.

Compound (6) (0.468 g; 0.896.10$^{-3}$ mole) is dissolved in MeCN (30 ml). To this colorless solution are added N-methyl morpholine (0.099 g; 0.986. 10$^{-3}$ mole), N-hydroxy benzotriazole (0.06 g; 0.448. 10$^{-3}$ mole), O-(1H-N-hydroxy benzotriazole-1-yl) -N,N,N',N'-tetramethyluronium tetrafluoroborate (0.317 g; 0.986. 10$^{-3}$ mole). The mixture is stirred 30 minutes at room temperature. Compound (9) (0.43 g; 0.896×10$^{-3}$ mole) then is dissolved in MeCN (5 ml) and is added with N-methyl morpholine (0.136 g; 1.344× 10$^{-3}$ mole). After 20 hours at room temperature, the acetonitrile is evaporated under reduced pressure. The residue is dissolved in CH$_2$Cl$_2$ (60 ml) and NaH$_2$PO$_4$ (30 ml). The organic phase is washed with NaH$_2$PO$_4$ (2×30 ml) and with brine (2×30 ml). After drying over Na$_2$SO$_4$, the solvent is evaporated. The residue is chromatographed on silica gel (Hexane:AcOEt, 1:1). Compound (10) is obtained as a pale yellow solid (0.692 g; 0.703. 10$^{-3}$ mole; 79%) $^1$H-NMR (CDCl$_3$, 500 MHz, δ(ppm), J(Hz)): 5.79 (H$_{1'}$, dd, $^3$J$_{1'\text{-}2}$=7.0 ); 6.20 (H$_1$', dd $^3$J$_{1'\text{-}2}$=6.4); 6.95 (H$_6$, q, $^4$J=1.0); 7.27 (H$_6$, q, $^4$J=1.0).—MS (EI; m/e): 984 (M$^+$).

J. Compound (11), Structure (III) wherein R$_{E1}$ is hydroxyl, R$_{E2}$ is hydroxyl, and R$_{E3}$ is H.

The compound (10) (0.68 g; 0.69×10$^{-3}$ mole) is dissolved under argon in THF (10 ml). Acetic acid (0.124 g; 2.07×10$^{-3}$ mole) and tetra-n-butyl amonium fluoride (1.88 ml of a 1.1M solution in THF; 2.07×10$^{-3}$ mole) are added. After 26 hours at room temperature, the mixture is coevaporated with toluene (3×) under reduced pressure. The residue is chromatographed on silica gel (AcOEt:MeOH, 20:1). Compound (11) is isolated as a white solid (0.295 g; 0.581×10$^{-3}$ mole; 84%). $^1$H-NMR (DMSO-d$_6$, 500 MHz, δ (ppm), J(Hz)): 5.95 (H$_1$', dd $^3$J$_{1'\text{-}2}$=6.2, $^3$J$_{1'\text{-}2}$=4.0); 6.22 (H$_{1'}$, dd, $^3$J$_{1'\text{-}2}$=6.2, $^3$J$_{1'\text{-}2}$=7.9); 7.47 (H$_6$, q, $^4$J=0.8); 7.85 (H$_6$, q, $^4$J=0.8).

K. Compound (12), Structure (Ill) wherein R$_{E1}$ is O-(dimethoxytrityl), R$_{E2}$ is hydroxl, and R$_{E3}$ is H.

Compound (11) (0.29 g; 0.571×10⁻³ mole) is dissolved under argon in pyridine (10 ml). DMTCl (4,4'-dimethoxy triphenylmethyl chloride; 0.194 g; 0.571×10⁻³ mole) is added. After 18 hours stirring at room temperature, an additional amount of DMTCl (0.097 g; 0.285×10⁻³ mole) is introduced. The reaction mixture is quenched with MeOH (1 ml) and after 40 hours is diluted with $CH_2Cl_2$ (50 ml) and $Na_2CO_3$ aq. (50 ml). The organic phase is washed with brine (2×30 ml) and dried over $Na_2SO_4$. The solvent is coevaporated with toluene (3×) under reduced pressure. The residue is chromatographed on silica gel (AcOEt:MeOH, gradient 50:1→10:1+1% N-methyl morpholine). Compound (12) (0.426 g; 0.526×10⁻³ mole; 92%) is isolated as a pale yellow solid. ¹H-NMR ($CDCl_3$, 500 MHz, δ(ppm)): 1.44 (Me, d); 1.88 (Me, d); 3.80 (2×OMe, s); 7.66 ($H_6$, q).

L. Compound (13), Structure (III) wherein $R_{E1}$ is O-(dimethoxytrityl), $R_{E2}$ is O-(2-cyanoethyl-N,N,N',N'-tetraisopropyl phosphordiamidyl), and $R_{E3}$ is H.

Compound (12) (0.413 g; 0.52×10⁻³ mole) is added under argon to a solution of 2-cyanoethyl-N,N,N',N'-tetraisopropyl phosphordiamidite (0.172 g; 0.572×10⁻³ mole) and N,N'-diisopropylammonium tetrazolide (0.107 g; 0.624×10⁻³ mole) in $CH_2Cl_2$ (20 ml). After 16 hours at room temperature, an additional amount of 2-cyanoethyl-N,N,N',N'-tetraisopropyl phosphordiamidite (0.172 g; 0.572×10⁻³ mole) is introduced. After 24 hours at room temperature, the mixture is quenched with $NaHCO_3$ aq. (20 ml). The organic phase is washed with brine (2×30 ml) and dried over $Na_2SO_4$. After evaporation of the solvent, the residue is chromatographed on silica gel (Toluene:AcOEt, 1:1+1% N-methyl morpholine). Compound (13) (0.299 g; 0.296×10⁻³ mole; 57%) is isolated as a white solid. ³¹P-NMR ($CDCl_3$, 101 MHz, δ(ppm)): 148.89 and 149.31.

EXAMPLE 22

Synthesis of Compound (17), Structure (IV) wherein $R_{E1}$ is O-(t-butyldiphenylsilyl), $R_{E2}$ is C(O)OH, and $R_{E3}$ is H.

A. Compound (14), Structure (IV) wherein $R_{E1}$ is O-(t-butyldiphenylsilyl), $R_{E2}$ is styryl, and $R_{E3}$ is H.

Compound (2) (3.558 g; 5.569×10⁻3 mole), prepared as in Example 21A, is dissolved under argon in degassed benzene (19 ml; 0.3M; degassed with a stream of argon for 30 minutes). After addition of AIBN (0.183 g; 1.113×10⁻³ mole) and 1-phenyl 2-n-tributyltinethylene (21.90 g; 55.69× 10⁻³ mole), the solution is heated at 80° C. AIBN (0.183 g; 1.113×10⁻³ mole) is added every 10 hour to a total of 0.915 g (5.566×10⁻³ mole). When no starting material is remaining (as determined by thin-layer using chromatography silica gel, Hexane:AcOEt, 1:1) the solvent is evaporated and the residue is chromatographed on silica gel (gradient Hexane:AcOEt, 10:1→4:1). Compound (14) is isolated as a white solid (2.367 g; 4.177×10⁻³ mole; 75%). ¹H-NMR ($CDCl_3$, 500 MHz, δ (ppm), J(Hz) ): 2.34 ($H_{2'}$, ddd, ²J=14.0, ³$J_{2'-2}$= 3.0, ³$J_{2'-3}$=8.2), 2.46 ($H_{2'}$, ddd, ³$J_{3'-4'}$=9.1); 6.21 ($H_{1'}$, dd); 7.58 ($H_6$, q, ⁴J=1.0).

B. Compound (15), Structure (IV) wherein $R_{E1}$ is O-t-butyldiphenylsilyl, $R_{E2}$ is formyl, and $R_{E3}$ is H.

Derivative (14) (2.193 g; 3.869×10⁻³ mole) is dissolved in a 2:1 mixture of dioxane:$H_2O$ (30 ml). $OsO_4$ (0.098 g; 0.386×10⁻³ mole) is added, followed by a solution of $NaIO_4$ (1.82 g; 8.512×10⁻³ mole) in $H_2O$ (8 ml). The resulting suspension is stirred 3 hours at room temperature and extracted with $CH_2Cl_2$ (3×50 ml). The organic phase is washed with brine (2×30 ml) and dried over $Na_2SO_4$. After evaporation of the solvent, the residue is chromatographed on silica gel (Hexane:AcOEt, 1:1). Aldehyde (15) is isolated as a white solid (1.334 g; 2.708×10⁻³ mole; 70%). ¹H-NMR ($CDCl_3$, 250 MHz, δ (ppm), J(Hz)): 2.26 ($H_{2'}$, ddd, ²J=15.3, ³$J_{2'-1}$=6.1, ³$J_{2'-3}$=9.4); 2.77 ($H_{2'\ ddd}$, ³$J_{2'-1}$=³$J_{2'-3}$=6.2); 3.36 ($H_{3'}$, m); 6×10 ($H_{1'}$, dd).

C. Compound (16), Structure (IV) wherein $R_{E1}$ is O-(t-butyldiphenylsilyl), $R_{E2}$ is C(O)OCH₃, and $R_{E3}$ is H.

Aldehyde (15) (1.091 g; 2.214×10⁻³ mole) is dissolved in DMF (10 ml). MeOH (0.425 g; 13.287×10⁻³ mole) and PDC (pyridinium dichromate; 4.998 g; 13. 287×10⁻³ mole) are added. The resulting dark brown solution is stirred 20 hours at room temperature, diluted with $CH_2Cl_2$ (50 ml), and washed with $NaH_2PO_4$ (2×50 ml) and with brine (2×50 ml). After drying over $Na_2SO_4$, the solvent is evaporated and the residue is chromatographed on silica gel (Hexane:AcOEt, 1:1). Compound (16) (0.661 g;.1.264×10⁻³ mole; 57%) is obtained as a white solid. ¹H-NMR ($CDCl_3$, 500 HHz, δ (ppm), J(Hz)): 2.28 ($H_{2'}$, ddd, ²J=14.5, ³$J_{2'-1}$=5.6, ³$J_{2'-3}$= 9.1); 2.76 ($H_{2'}$, ddd, ³$J_{2'-1}$=³$J_{2'-3}$=6.9); 3.42 ($H_{3'}$, ddd); 4.28 ($H_{4'}$, ddd, ³$J_{3'-4'}$=7.0); 6.21 ($H_{1'}$, dd).

D. Compound (17), Structure (IV) wherein $R_{E1}$ is O-(t-butyldiphenylsilyl), $R_{E2}$ is C(O)OH, and $R_{E3}$ is H.

Ester derivative (16) (2.2 g; 4.209×10⁻³ mole) is dissolved in a 1:1 mixture of THF-$H_2O$ (50 ml). A solution of NaOH 0.1N (126.3 ml; 12.627×10⁻³ mole) is added. After 16 hours of stirring at room temperature, the mixture is neutralized with HCl 1N, extracted with $CH_2Cl_2$ (2×50 ml). The organic phase is washed with brine (2×50 ml) and dried over $Na_2SO_4$. After evaporation of the solvent, compound (17) is obtained as a white solid (2.015 g; 3.985×10⁻³ mole; 94%). ¹H-NMR ($CDCl_3$, 250 MHz, δ (ppm)); 6.22 ($H_{1'}$, dd).

EXAMPLE 23

Synthesis of Compound (26), Structure (V) wherein $R_{E1}$ is O-(dimethyoxytrityl), $R_{E2}$ is O-(2-cyanoethyl-N,N,N',N'-tetraisopropyl phosphordiamidyl), and $R_{E3}$ is H.

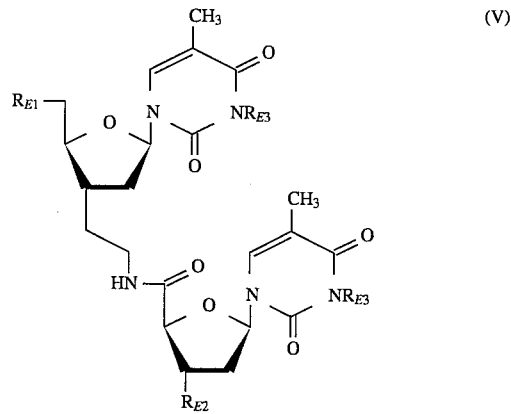

A. Compound (18 ), Structure (IV) wherein $R_{E1}$ is O-(t-butyldiphenylsilyl), $R_{E2}$ is hydroxyethyl, and $R_{E3}$ is H.

Compound (4) (5.323 g; 10.5×10⁻³ mole), prepared as in Example 21C, is dissolved in MeOH (60 ml). $NaBH_4$ (1.192 g; 31.51×10⁻³ mole) is added portionwise at 0° C. When hydrogen evolution deceased, the reaction mixture was stirred at room temperature for 2 hours. $NaH_2PO_4$ aq. (20 ml) is added carefully. The MeOH is evaporated and the residue extracted with $CH_2Cl_2$ (2×50 ml). The organic phase is washed with brine (50 ml) and dried over $Na_2SO_4$. The solvent is evaporated and the residue is chromatographed on silica gel (Hexane-AcOEt 1:1). Compound (18) is isolated as a white solid (5.01 g; 9.84×10$^{-3}$ mole; 94%). $^1$H-NMR (CDCl$_3$, 500 MHz, δ (ppm), J(Hz)): 2.15 (H$_{2'}$, ddd $^2$J=13.5, $^3$J$_{2'-1}$=7.0, $^3$J$_{2'-3}$=9.0); 2.27 (H$_{2'}$, ddd, $^3$J$_{2'-1}$=4.0, $^3$J$_{2'-3}$=8 0); 2.49 (H$_{3'}$, m); 3.77 (H$_{4'}$, ddd); 6.11 (H$_{1'}$, dd).

B. Compound (19), Structure (IV) wherein R$_{E1}$ is O-(t-butyldiphenylsilyl), R$_{E2}$ is ethoxy-toluene sulfonyl, and E$_{E3}$ H.

Compound (18) (0.334 g; 0.656×10$^{-3}$ mole) is dissolved under argon in CHCl$_3$ (15 ml). DMAP (0.241 g; 1.969×10$^{-3}$ mole), pyridine (0.208 g; 2.626×10$^{-3}$ mole), and tosylchloride (0.375 g; 1.969×10$^{-3}$ mole) are added sequentially. After 24 hours of stirring at room temperature, additional amounts of reagents are introduced: DMAP (0.12 g; 0.984×10$^{-3}$ mole); pyridine (0.102 g; 1.313×10$^{-3}$ mole); tosyl chloride (0.187 g; 0.984×10$^{-3}$ mole). The reaction mixture is diluted with CH$_2$Cl$_2$ (60 ml) after 40 hours and washed with NaH$_2$PO$_4$ aq. (2×50 ml) and with brine (2×50 ml). The organic phase is dried over Na$_2$SO$_4$. After evaporation of the solvent, the residue is chromatographed on silica gel (Hexane:AcOEt, 2:1). Compound (19) (0.369 g; 0.556×10$^{-3}$ mole; 84%) is isolated as a pale yellow solid. $^1$H-NMR (CDCl$_3$, 250 MHz, δ (ppm): 2.44 (pMe-Ph-SO$_3$—,s).

C. Compound (20), having atructure (IV) wherein R$_{E1}$ is O-(t-butyldiphenylsilyl), R$_{E2}$ is azidoethyl, and R$_{E3}$ is H.

Compound (19) (0.365 g; 0.55×10$^{-3}$ mole) is dissolved in DMF (10 ml) under an atmosphere of dry argon. To this solution are added LiN$_3$ (0.135 g; 2.75×10$^{-3}$ mole) and NaI (0.165 g; 1.1×10$^{-3}$ mole). The mixture is heated at 100° C. for 17 hours, then cooled to room temperature. Ether (100 ml) is added, then brine (50 ml). The organic phase is washed with brine (2×50 ml) and dried over Na$_2$SO$_4$. After evaporation of the solvents under reduced pressure, the residue is chromatographed on silica gel (Hexane:AcOEt, 3:1). Compound (20) is isolated as a pale yellow oil (0.259 g; 0.485×10$^{-3}$ mole; 88%). $^1$H-NMR (CDCl$_3$; 500 MHz, δ (ppm), J(Hz) ): 2.13 (H$_{2'}$, ddd, $^2$J=13.5, $^3$J$_{2'-3}$=8.7, $^3$J$_{2'-1}$=7.0); 2.26 (H$_{2'}$, ddd, $^3$J$_{2'-3}$=7.9, $^3$J$_{2'-1}$=4.0); 2.47 (H$_{3'}$, m); 3.73 (H$_{4'}$, ddd $^3$J$_{4'-3}$=8.0); 6.11 (H$_{1'}$, dd).

D. Compound (21 ), Structure (IV) wherein R$_{E1}$ is O-(t-butyldiphenylsilyl), R$_{E2}$ is aminoethyl, and R$_{E3}$ is H.

Azide derivative (20) (0.255 g; 0.477×10$^{-3}$ mole) is dissolved under argon in a degassed solution of benzene (0.1M: degassed with a stream of argon for 30 minutes; 5 ml). AIBN (0.008 g; 0. 047×10$^{-3}$ mole) and n-tributyltin hydride (0.347 g; 1.19×10$^{-3}$ mole) are added at room temperature. The mixture is heated at 80° C. for 5 hours. The solvent is evaporated under reduced pressure. The residue is chromatographed on silica gel (gradient CHCl3:MeOH, 50:1→10:1). Compound (21) is isolated as a pale yellow oil (0.23 g; 0.452×10$^{-3}$ mole; 95%). $^1$H-NMR (CDCl$_3$, 500 MHz, δ (ppm), J(Hz)): 2.12 (H$_{2'}$, ddd, $^3$J$_{2'-1}$=6.9); 2.24 (H$_{2'}$, ddd, $^3$J$_{2'-1}$=4.0); 2.38 (H$_{3'}$, m); 3.74 (H$_{4'}$, ddd, $^3$J$_{3'-4'}$=8.0); 6.09 (H$_{1'}$, dd). MS(FD, m/e): 508 (M$^+$).

E. Compound (22), Structure (IV) wherein R$_{E1}$ is C(O)OH, R$_{E2}$ is O-(t-butyldiphenylsilyl), and R$_{E3}$ is H.

Compound (22) was prepared generally according to the procedures described in Tetrahedron Letters, 30 (37): 4969–4972 (1989 ).

F. Compound (23), Structure (V) wherein R$_{E1}$ is O-(t-butyldiphenylsilyl), R$_{E2}$ is O-(t-butyldiphenylsilyl), and R$_{E3}$ is H.

Compound (22) (2.205 g; 4.459×10$^{-3}$ mole) is dissolved in MeCN (80 ml) and THF (10 ml). To this solution are added N-methyl morpholine (0.496 g; 4.905×10$^{-3}$ mole), N-hydroxy benzotriazole (0.301 g; 2.229×10$^{-3}$ mole), and O-(1H-N-hydroxy benzotriazole-1-yl) N,N,N',N'-tetramethyl uronium tetrafluoroborate (1.575 g; , 4.9×10$^{-3}$ mole). The mixture is stirred 30 minutes at room temperature. Compound (21) (2.264 g; 4.45×10$^{-3}$ mole), dissolved in MeCN (20 ml ), is added with N'-methyl morpholine (0.676 g; 6.688×10$^{-3}$ mole). After 20 hours at room temperature, the solvents are evaporated under reduced pressure. The residue is dissolved in CH$_2$Cl$_2$ (100 ml) and NaH$_2$PO$_4$ aq. (50 ml). The organic phase is washed with NaH$_2$PO$_4$ (2×50 ml) and with brine (2×50 ml) and dried over Na$_2$SO$_4$. The solvent is evaporated and the residue is chromatographed on silica gel (Hexane:AcOEt, 1:2). Compound (23) is isolated as a white solid (4.11 g; 4.175×10$^{-3}$ mole; 93%). $^1$H-NMR (CDCl$_3$, 500 MHz, δ (ppm), J(Hz)): 2.34 (H$_{2'}$, ddd, $^2$J=14.3, $^3$J$_{2'-3'}$, =4.3, $^3$J$_{2'-1}$=9.9); 4.01 (H$_{5'}$, m); 4.28 (H$_{4'}$, s); 4.55 (H$_{3'}$, d) ; 6.07 (H$_{1'}$, dd, $^3$J$_{1'-2}$=6.5, $^3$J$_{1'-2}$=3.8 ); 6.17 (H$_{1'}$, dd, $^3$J$_{1'-2}$=5.0). MS (CI; m/e): 984 M$^+$.

G. Compound (24), Structure (V) wherein R$_{E1}$ is hydroxyl, R$_{E2}$ is hydroxyl, and R$_{E3}$ is H.

Compound (23) (1.292 g; 1.312×10$^{-3}$ mole) is dissolved under argon in THF (30 ml). Acetic acid (0.236 g; 3.937×10$^{-3}$ mole) and tetra-n-butylammonium fluoride (3.58 ml of a 1.1M solution in THF; 3.937×10$^{-3}$ mole) are added. After 24 hours at room temperature, the mixture is coevaporated with toluene (3×) under reduced pressure. The residue is chromatographed on silica gel (AcOEt:MeOH, 20:1). Compound (24) is isolated as a white solid (0.647 g; 1.27×10$^{-3}$ mole; 97%). 1H-NMR (CD$_3$OD, 500 MHz, δ (ppm), J(Hz)): 4.25 (H$_{4'}$, d, $^3$J$_{4'-3'}$=1.9); 6.05 (H$_{1'}$, dd, $^3$J$_{1'-2}$=2.1, $^3$J$_{1'-2}$=7.8); 6.21 (H$_{1'}$, dd, $^3$J$_{1'-2}$=5.9, $^3$J$_{1'-2}$=8.4); 7.88 (H$_6$, q); 8.03 (H$_6$, q).

H. Compound (25), Structure (V) wherein R$_{E1}$ is O-(dimethoxytrityl), R$_{E2}$ is hydroxyl, and R$_{E3}$ is H.

Compound (24) (0.64 g; 1.261×10$^{-3}$ mole) is dissolved under argon in pyridine (10 ml). DMTCl (4,4'-dimethoxy triphenylmethyl chloride; 0.428 g; 1.263×10$^{-3}$ mole) is added. After 17 hours stirring at room temperature, an additional amount of DMTCl (0.428 g; 1.263×10$^{-3}$ mole) is introduced. The reaction mixture is quenched with MeOH (1 ml) after 40 hours and diluted with CH$_2$Cl$_2$ (60 ml) and Na$_2$CO$_3$ aq. (50 ml). The organic phase is washed with brine (2×30 ml) and dried over Na$_2$SO$_4$. The solvent is coevaporated with toluene (3×) under reduced pressure. The residue is chromatographed on silica gel (AcOEt:MeOH, gradient 50:1→10:1+1% N-methyl morpholine). Compound (25) (0.902 g; 1.11×10$^{-3}$ mole; 88%) is isolated as a white solid. $^1$H-NMR(CD$_3$OD, 500 MHz, δ (ppm), J(Hz)): 4.23 (H$_{4'}$, d, $^3$J$_{4'-3'}$ =1.8); 6.06 (H$_{1'}$, dd, $^3$J$_{1'-2}$=2.4, $^3$J$_{1'-2}$=7.5); 6.19 (H$_{1'}$, dd, $^3$J$_{1'-2}$=5.9, $^3$J$_{1'-2}$=9.0) MS(CI: m/e): 809 (M+).

I. Compound (26), Structure (V) wherein R$_{E1}$ is O-(dimethyoxytrityl), R$_{E2}$ is O-(2-cyanoethyl-N,N,N',N'-tetraisopropyl phosphordiamidyl), and R$_{E3}$ is H.

Compound (25) (0.89 g; 1.121×10$^{-3}$ mole) is added under argon to a solution of 2-cyanoethyl-N,N,N',N'-tetraisopropyl phosphordiamidite (0.371 g; 1.233×10$^{-3}$ mole) and of N,N'-diisopropylammonium tetrazolide (0.23 g; 1.345×10$^{-3}$ mole) in CH$_2$Cl$_2$ (30 ml). After 18 hours at room temperature, an additional amount of 2-cyanoethyl-N,N,N',N'-tetraisopropyl phosphordiamidite (0.371 g; 1.233×10$^{-3}$ mole) is introduced. After 24 hours at room temperature, the mixture is quenched with NaHCO$_3$ aq. (20 ml). The organic phase is washed with brine (2×30 ml) and dried over Na$_2$SO$_4$. After evaporation of the solvent, the residue is chromatographed on silica gel (hexane:AcOEt, 1:2+1% N-methyl morpholine). Compound (26) is isolated as a pale yellow solid (0.624 g; 0.617×10$^{-3}$ mole; 55%). $^{31}$P-NMR (CDCl$_3$, 101 MHz, δ (ppm)): 148.17 and 150.57.

EXAMPLE 24

Synthesis of Compound (30), Structure (IV) wherein $R_{E1}$ is O-(t-butyldiphenylsilyl), $R_{E2}$ i aminomethyl, and $R_{E3}$ is H.

A. Compound (27), Structure (IV) wherein $R_{E1}$ is O-(t-butyldiphenylsilyl), $R_{E2}$ is hydroxymethyl, and $R_{E3}$ is H.

Aldehyde (15) (0.759 g; $1.541 \times 10^{-3}$ mole), prepared as described in Example 22A–B, is dissolved under argon in MeOH (6 ml). The solution is cooled to 0° C. and $NaBH_4$ (0.291 g; $7.708 \times 10^{-3}$ mole) is added. After 30 minutes at this temperature, the mixture is stirred at 25° C. for 20 hours. To this solution is added $NaH_2PO_4$ aq. (30 ml). The MeOH is evaporated under reduced pressure and the aqueous phase is extracted with $CH_2Cl_2$ (3×30 ml). The organic phase is washed with brine (2×20 ml) and dried over $Na_2SO_4$. After removal of the solvent, the residue is chromatographed on silica gel (Hexane:AcOEt, 1:2). Compound (27) is isolated as a white solid (0.381 g; $0.77 \times 10^{-3}$ mole; 50%). $^1$H-NMR ($CDCl_3$, 500 MHz, δ (ppm), J(Hz) ): 2.14 ($H_{2'}$, ddd, $^2J=14.0$, $^3J_{2'-1}=5.2$, $^3J_{2'-3}=8.8$); 2.29 ($H_{2'}$, ddd, $^3J_{2'-1}=6.8$, $^3J_{2'-3}=5.9$); 2.60 ($H_{3'}$, m); 3.94 ($H_{4'}$, ddd); 6.13 ($H_{1'}$, dd). MS(FD, m/e): 495 ($M^+$).

B. Compound (28), Structure (IV) wherein $R_{E1}$ is O-(t-butyldiphenylsilyl), $R_{E2}$ is methoxy p-toluene sulfonyl, and $R_{E3}$ is H.

Compound (27) (0.397 g; $0.802 \times 10^{-3}$ mole) is dissolved under argon in $CHCl_3$ (15 ml). To this solution, cooled at 0° C., are added pyridine (0.254 g; $3.21 \times 10^{-3}$ mole); DMAP (0.294 g; $2.407 \times 10^{-3}$ mole), and tosylchloride (0.459 g; $2.407 \times 10^{-3}$ mole). After 10 minutes at 0° C., the mixture is stirred at room temperature. Analytical thin-layer chromatography (Hexane:AcOEt, 1:1) reveals that some starting material remains. Therefore, adds tosyl chloride (0.306 g; $1.6 \times 10^{-3}$ mole), pyridine (0.127 g; $1.605 \times 10^{-3}$ mole), and DMAP (0.196 g; $1.6 \times 10^{-3}$ mole) were added. After 40 hours, this solution is diluted with $CHCl_3$ (50 ml), washed with $NaH_2PO_4$ aq. (2×40 ml ), with $NaHCO_3$ aq. (2×40 ml), and with brine (2×40 ml), and dried over $Na_2SO_4$. After evaporation of the solvent under reduced pressure, the residue is chromatographed on silica gel (Hexane:AcOEt, 2:1). Compound (28) is isolated as a colorless solid (0.429 g; $0.661 \times 10^{-3}$ mole; 82%). $^1$H-NMR ($CDCl_3$, 500 MHz, δ (ppm), J(Hz) ): 2.14 ($H_{2'}$, ddd, $^2J=14.8$, $^3J_{2'-1}=5.6$, $^3J_{2'-3}=9.0$); 2.22 ($H_{2'}$, ddd, $^3J_{2'-1}=6.8$, $^3J_{2'-3}=6.8$); 2.84 ($H_{3',m}$); 3.85 ($H_{4'}$, ddd, $^3J_{3'-4}=7.0$); 6.05 ($H_{1'}$, dd). MS(FD, m/e): 649 ($M^+$).

C. Compound (29), Structure (IV) wherein $R_{E1}$ is O-(t-butyldiphenylsilyl), $R_{E2}$ is azidomethyl, and $R_{E3}$ is H.

Tosyl derivative (28) (0.425 g; $0.655 \times 10^{-3}$ mole) is dissolved under argon in DMF (15 ml). To this solution are added $LiN_3$ (0.16 g; $3.275 \times 10^{-3}$ mole) and NaI (0.196 g; $1.31 \times 10$ mole) at room temperature. The mixture is stirred for 20 hours at 100° C. The reaction is followed by analytical thin-layer chromatography (hexane:AcOEt, 1:3). When the reaction is finished, ether is added (100 ml). This solution is washed with brine (3×50 ml) and dried over $Na_2SO_4$. After filtration, the residue is chromatographed on silica gel (Hexane:AcOEt, 2:1). Azide derivative (29) is obtained as a colorless glass (0.262 g; $0.504 \times 10^{-3}$ mole; 77%). $^1$H-NMR ($CDCl_3$, 500 MHz, δ (ppm), J(Hz)): 2.18 ($H_{2'}$, ddd, $^2J=14.3$, $^3J_{2'-3}=8.9$, $^3J_{2'-1}=5.5$); 2.28 ($H_{2'}$, ddd, $^3J_{2'-3}=^3J_{2'-1}=6.5$); 2.67 ($H_{3'}$, m); 3.37 ($CH_2-N_3$, d, $^3J=6.3$); 7.46 ($H_6$, q, $^4J=1.0$) MS(FD, m/e): 520 ($M^+$).

D. compound (30), Structure (IV) wherein $R_{E1}$ is O-(t-butyldiphenylsilyl), $R_{E2}$ is aminomethyl, and $R_{E3}$ is H.

Azide derivative (29) (0.245 g; $0.471 \times 10^{-3}$ mole) is dissolved under argon in a degassed solution of benzene (0.1M: degassed with a stream of argon for 30 minutes). AIBN (0.008 g; $0.0471 \times 10^{-3}$ mole) and $nBu_3SnH$ (n-tributyltin hydride; 0.343 g; $1.178 \times 10^{-3}$ mole) are added at room temperature. The mixture is heated at 80° C. during 7 hours. Analytical thin layer chromatography (Hexane:AcOEt, 1: 1) reveals that some starting material is still present in the reaction mixture. Therefore, AIBN is added (0.008 g; $0.0471 \times 10^{-3}$ mole). The reaction mixture is heated for and additional 17 hours at 80° C. The solvent is evaporated under reduced pressure. The residue (pale yellow oil) is chromatographed on silica gel (flash-chromatography; gradient AcOEt:MeOH, 50:1→20:1→10:1 containing 1% of $NEt_3$). Amine (30) is isolated as a white powder (0.196 g; $0.397 \times 10^{-3}$ mole; 84%). $^1$H-NMR ($CD_3OD$, 500 MHz, δ (ppm), J(Hz)): 2.28 ($2H_{2'}$; m); 2.58 ($H_{3'}$, m); 2.70 ($C_{3'}-CH_2-NH_2$, dd, $^2J=12.2$, $^3J=8.0$); 2.82 ($C_{3'}-CH_2-NH_2$, dd, $^3J=5.4$); 6.11 ($H_{1'}$, dd, $^3J=5.9$); 7.54 ($H_6$, q, $^4J=1.1$). MS (FD, m/e): 494 ($M^+$).

EXAMPLE 25

Synthesis of Compound (42), Structure (VI) wherein $R_{E1}$ is O-(dimethyoxytrityl), $R_{E2}$ is O-(2-cyanoethyl-N,N,N',N' tetraisopropyl phosphoramidyl), and $R_{E3}$ is H.

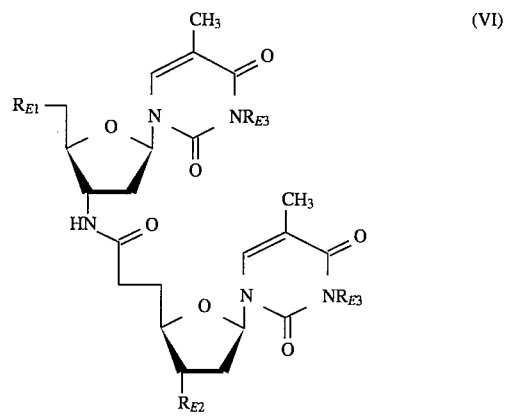

A. Compound (31), Structure (IV) wherein $R_{E1}$ is hydroxyl, $R_{E2}$ is O-(t-butyldiphenylsilyl), and $R_{E3}$ is H.

Compound (31) was prepared generally in accordance with the methods described in *Tetrahedron Letters*, 23(26): 2641-2644 (1982).

B. Compound (32), Structure (IV) wherein $R_{E1}$ is hydroxyl, $R_{E2}$ is O-(t-butyldiphenylsilyl), and $R_{E3}$ is $CH_2OCH_2Ph$.

To a stirred solution of (31) (3.53 g, 7.4 mmol) in ml of dry acetonitrile at room temperature under argon was added DBU (2.2 ml, 14.8 mmol) followed by benzylchloromethylether (2.0 g, 12.8 mmol). After 4 hours at room temperature, the reaction was diluted with 150 ml of $CH_2Cl_2$, and the organic phase was washed with two 25 ml portions of a 10% aqueous $KHSO_4$, one 70 ml portion of $H_2O$ and one 50 ml portion of brine. After drying over $Na_2SO_4$, the organic phase was concentrated under reduced pressure. Chromatography of the residue on silica gel (gradient Hexane:AcOEt) afforded the protected thymidine (32) as a white foam (3.21 g, 73%). $^1$H NMR ($CDCl^3$, 300 MHz) δ: 1.01 (9H, s, 3'-O'-SitBu), 1.79 (3H, s, Me-5), 4.61 (2H, s, O—$CH_2$—Ph), 5.40 (2H,s,-N-$CH_2$—O).

C. Compound (33), Structure (IV) wherein $R_{E1}$ is $CHC(O)OCH_3$, $R_{E2}$ is O-(t-butyldiphenylsilyl), and $R_{E3}$ is $CH_2OCH_2Ph$.

To a stirred solution of oxalyl chloride (0.65 ml, 7.3 midol) in 25 ml of dry $CH_2Cl_2$ at −78° C. under argon was added a solution of dry DMSO (1.05 ml, 14.6 mmol) in 5 ml of $CH_2Cl_2$. The addition was performed over 5 minutes. The resultant mixture was stirred for 1 hour at −78° C. and a solution of compound (32) (2.91 g, 4.84 mmol) in 25 ml of $CH_2Cl_2$ was added over 10 minutes. After 1 h at −78° C., dry triethylamine (4.1 ml, 29.2 mmol) was added and the reaction mixture was allowed to warm to 0° C. Methoxycarbonyl methylene triphenylphosphorane (2.45 g, 7.2 mmol) was added as a solid and the reaction was stirred at room temperature for 2 hours. A 200 ml portion of $CH_2Cl_2$ was added, followed by 50 ml of $H_2O$. The resulting mixture was stirred 10 minutes and the layers were separated. The organic layer was washed with two 50 ml portions of $H_2O$ and one 50 ml portion of brine. The organic layer was dried over $Na_2SO_4$ and concentrated under reduced pressure. Chromatography of the residue on silica gel (4:1 hexane/ethyl acetate) afforded α,β-unsaturated methylester (33) (2.95 g; 93%). $^1H$ NMR ($CDCl_3$, 300 MHz)δ: 0.875 (9H,s, 3'-OSitBu); 5.66 (1H, dd, J=16 Hz, J=1.5 Hz, H-6'), 6.45 (1H, dd, J=7Hz, H-1'), 6.41 (1H, dd, J=16 Hz and J=6 Hz).

D. Compound (34), Structure (IV) wherein $R_{E1}$ is $CH_2C(O)OCH_3$, $R_{E2}$ is O-(t-butyldiphenylsilyl), and $R_{E3}$ is H.

A vigorously stirred solution of (33) (2.7 g, 4.1 mmol) in 85 ml of MeOH was hydrogenated under hydrogen (atmospheric pressure) at room temperature in the presence of powdered Pd/C 10% (960 mg) for 3 days. The reaction mixture was filtered through a path of $SiO_2$, and the filter cake was washed with MeOH (~100 ml). Concentration of the filtrate under reduced pressure afforded crude (34) (2.1 g, 95%) as an colorless foam. This material was used for the next step without further purification. $^1H$-NMR ($CDCl_3$, 300 MHz) δ:1.82 (3H, s, Me-5), 3.56 (3H, s, OMe), 6.25 (1H, dd, J=6 Hz, H-1'), 6.92 (1H,s, H-6), 8.6 (1H, s broad, N-H).

E. Compound (35), Structure (IV) wherein $R_{E1}$ is $CH_2C(O)OH$, $R_{E2}$ is O-(t-butyldiphenylsilyl), and $R_{E3}$ is H.

To a solution of the crude compound (34) (2.1 g, 3.9 mmol) in MeOH (10 ml) at room temperature, was added 40 ml of a 2M solution of KOH in MeOH/$H_2O$ (7:3). After 2 hours at room temperature, the solution was acidified to pH 4 with Dowex 50W×4 (Fluka). The suspension then was filtered and the solid washed with 150 ml of $CH_2Cl_2$ and 50 ml $H_2O$. The layers were separated. The aqueous layer was extracted with $CH_2Cl_2$. The combined organic layers were washed with 50 ml portions of $H_2O$ and brine. The organic layer was dried over $Na_2SO_4$ and concentrated under reduced pressure to give acid (34) (1.27 g, 84%) as a white powder. $^1H$ NMR ($CDCl_3$, 300 MHz) δ: 1.82 (3H, s; Me-5) 3.9 (1H, m, H-4'), 6.25 (1H, s, H-1') 6.95 (1H, s, H-6).

F. Compound (36), Structure (IV) wherein $R_{E1}$ is O-(trityl), $R_{E2}$ is azido, and $R_{E3}$ is H.

Compound (36) was prepared generally according to the procedures described in Lin, T. and W. Prusoff, *J. Med. Chem.* 21: 109 (1978).

G. Compound (37), Structure (IV) wherein $R_{E1}$ is O-(trityl), $R_{E2}$ is amino, and $R_{E3}$ is H.

A 10.5 g (0.02 Mol) portion of azide (36) is dissolved in 100 ml dioxane. After the addition of 0.5 g of 10% pd/C, hydrogenation is carried out under atmospheric pressure at 25° C. Filtration after 16 h and evaporation under reduced pressure afforded the crude amine, which was crystallized with $CH_2Cl_2/Et_2O$. Yield 7.0 g of amino derivative (37). $^1H$-NMR (DMSO-$d_6$): 1.50 (s, 3H, $CH_3$); 6.15 (m, 1H, H(1')); 7.50 (s, 1H, H(6)).

H. Compound (38), Structure (VI) wherein $R_{E1}$ is O-(trityl), $R_{E2}$ is O-(t-butyldiphenylsilyl), and $R_{E3}$ is H. (38)

To a stirred mixture of (35) (313 mg, 0.6 mmol) and amine (37) (289 mg, 0.6 mmol) in 5 ml of dry $CH_2Cl_2$ under argon at room temperature was added N,N'-dicyclohexylcarbodiimide (144 mg, 0.7 mmol) and DMAP (30 mg, 0.25 mmol). After 12 hours at room temperature, the mixture was diluted with 100 ml of $CH_2Cl_2$ and was washed with 20 ml of 0.1N HCl, 3×20 ml of $H_2O$ and 2×20 ml of brine. The organic layer was dried over $Na_2SO_4$ and concentrated under reduced pressure to furnish an oil (0.95 g), which was chromatographed on silica gel (98:2 chloroform; methanol) to afford dimer (38) (0.46 g, 78%) as a white foam. $^1H$ NMR ($CDCl^3$, 300 MHz) δ: 1.32 and 1.80 (3H, s, Me-5), 5.96 and 6.25 (1H, dd, J=6 Hz, H-1'), 6.52 (1H, d, J=6Hz, N-H (chain)), 6.9 and 7.5 (1H, s, H-6) 9.18 and 9.37 (1H, s broad, N3-H).

I. Compound (39), Structure (VI) wherein $R_{E1}$ is hydroxyl, $R_{E2}$ is O-(t-butyldiphenylsilyl), and $R_{E3}$ is H.

A solution of (38) (1.01 g, 1.02 mmol) in a mixture of acetic acid (1.6 ml) and water (0.4 ml) was heated at 80° C. for 1 hour 30 minutes. The solvent then was removed under reduced pressure and the residue was chromatographed on silica gel ($CH_2Cl_2$/MeOH/$Et_3$N, 95:4:1) to afford (39) (591 mg, 78%) as a white foam. $^1H$-NMR ($CDCl_3$, 300 MHz) δ: 1.76 and 1.82 (3H, s, Me-5), 6.02 and 6.10 (1H, dd, J=6 Hz, H-1') 6.9 and 7.6 (1H, 1s, H-6), 7;05 (1H, d broad, NH (chain)), 9.82 and 9.92 (1H, s broad, N3-H).

J. Compound (40), Structure (VI) wherein $R_{E1}$ is O-(dimethoxytrityl), $R_{E2}$ is O-(t-butyldiphenylsilyl), and $R_{E3}$ is H.

To a solution of (39) (860 mg, 1.15 mmol) in 20 ml of $CH_2Cl_2$ at room temperature under argon was added DMAP (210 mg, 1.7 mmol) and $Et_3N$ (0.5 ml, 3.5 mmol), followed by dimethoxytrityl chloride (575 mg, 1.7 mmol). After stirring for 12 hours at room temperature, more dimethoxytrityl chloride (300 mg, 8.8 mmol) was added. After 24 hours at room temperature, the reaction mixture was diluted with $CH_2Cl_2$ (~100 ml) and was washed with brine. The organic phase was dried over $Na_2SO_4$ and concentrated under reduced pressure to give an oil, which was purified by chromatography on silica gel ($CH_2Cl_2$/MeOH/$Et_3$N 94:5:1) to afford (40) (575 mg, 48%). $^1H$NMR ($CDCl_3$; 300 MHz) δ: 1.46 and 1.92 (3H, s, Me-5), 3.88 (6H, s, OMe), 6.13 and 6.4 (1H, s, H-1'), 7.07 (1H, s, H6) 9.5 and 9.6 (1H, s broad, $N_3$-H).

K. Compound (41), Structure (VI) wherein $R_{E1}$ is O-(dimethoxytrityl), $R_{E2}$ is hydroxyl, and $R_{E3}$ is H.

To a solution of (40) (405 mg, 0.39 mmol) in 3 ml of THF at room temperature was added tetra-n-butylammonium fluoride (141 mg, 0.5 mmol) at once as a solid. After 3 hours at room temperature, the solvent was removed under reduced pressure and the residues was purified by chromatography on silica gel ($CH_2Cl_2/Et_3$N/methanol, 93:1:6) to afford (41) (310 mg, 100%) as a white foam. $^1H$ NMR ($CDCl^3$, 300 MHz) δ: 1.21 and 1.73 (3H, s, Me-5), 3.64 (6H, s, OMe), 6.00 and 6.22 (3H, dd, J=6 Hz, H-1'), 7.25 and 7.55 (1H, s, H-6).

L. Compound (42), Structure (VI) wherein $R_{E1}$ is O-(dimethoxytrityl), $R_{E2}$ is O-(2-cyanoethyl-N,N,N',N' tetraisopropyl phosphoramidyl), and $R_{E3}$ is H.

To a stirred solution of (41) (310 mg, 0.39 μ/mol) in 5 ml of dry $CH_2Cl_2$ containing diisopropylammonium tetrazolide (55 mg, 0.32 mmol) under argon at room temperature was added the 2-cyanoethyl-N,N,N',N ' tetraisopropyl phosporadiamidite (0.180 ml, 0.6 mmol). After 13 hours at room temperature, the reaction mixture was diluted with 100 ml of $CH_2Cl_2$, washed with 5% aqueous solution of $NaHCO_3$, $H_2O$ and brine. After drying over $Na_2SO_4$, the solvent was removed under reduced pressure. The crude oil was purified by chromatography on silica gel ($CH_2Cl_2$/N-methyl morpholine/methanol 98:1:1) to afford (42) (285 mg, 74%) [which was coevaporated 3 times with 150 ml of dry benzene to give a white foam]. $^{31}P$ NMR ($CDCl^3$, 100 MHz) δ: 148.658 and 148.070 ppm.

EXAMPLE 26

Synthesis of Compound (48), Structure (IV) wherein $R_{E1}$ is C(O)OH, $R_{E2}$ is O-(t-butyldiphenylsilyl), and $R_{E3}$ is H.

A. Compound (43), Structure (IV) wherein $R_{E1}$ is aminomethyl, $R_{E2}$ is hydroxyl, and $R_{E3}$ is H.

Compound (43) was prepared generally in accordance with the procedures described in *Chem. Comm.* p. 422 (1968).

B. Compound (44), Structure (IV) wherein $R_{E1}$ is aminomethyl, $R_{E2}$ is O-(t-butyldimethylsilyl), and $R_{E3}$ is H.

To a mixture of crude aminoalcohol (43) (1.40 g, 5.5 mmol) in dry DMF 10 ml and dry $CH_2Cl_2$ 5 ml was added at room temperature under argon, imidazole (520 mg, 7.6 mmol) and t-butyl dimethylchlorosilane (1.08 g, 7.2 mmol). The resulting mixture was stirred 8 hours at room temperature and more reagents were added: imidazole (210 mg, 3.1 mmol ); t-butyldimethylchlorosilane (420 mg, 2.8 mmol). After 22 hours, the solvents were removed under high vacuum (~10-2 mmHg, 45° C.). The crude solid was purified on Silica gel ($CH_2Cl_2$/MeOH/$Et_3N$) to give (44) (1.70 g, 83%) as pale yellow foam. $^1$HNMR ($CDCl_3$; 300 MHz) δ: 0.00 (6H, s, 3'-$OSiMe_2$); 0.81 (9H, s, 3'-O'SitButyl); 1.75 (2H, m, H-5'); 1.97 (3H, s, Me-T); 2.15 (2H, m, H-2'); 3.40 (2H, m, H-6'); 3.74 (1H, m, H-4'); 4.05 (1H, m, H-3'); 6.07 (1H, t, J=6.5 Hz; H-1'); 7.06 (1H, s, H-6), 8.10 (1H, s, N-H).

C. Compound (45) Structure (IV) wherein $R_{E1}$ is CH=$CH_2$, $R_{E2}$ is O-(t-butydiphenylsilyl), and $R_{E3}$ is $CH_2OCH_2Ph$.

To a stirred solution of oxalyl chloride (2.2 ml, 25 mmol) in 45 ml of dry $CH_2Cl_2$ at −78° C. under argon was added a solution of dry DMSO (3.6 ml, 50 mmol) in 15 ml of $CH_2Cl_2$ over 5 min After stirring for 1 hour at −78° C. a solution of compound (32) (10 g, 10.64 mmol), prepared in accordance with examples 25A-B, in 50 ml of $CH_2Cl_2$ was added. After 45 min. at −78° C., dry triethylamine (14.8 ml, 0.1 mol) was added over 5 min and the reaction mixture was allowed to warm to −30° C. over 1 hour. To the latter solution at −78° C. was added a solution of methylene triphenylphosphorane, prepared by addition of 1.6N n-butyl lithium in hexane (62.5 ml, 0.1 mol) to a stirred slurry solution of methyl-triphenylphosphonium bromide (35.7 g, 0.1 mol) in 150 ml of dry THF at −78° C., followed by stirring at RT for 2 hours. The resulting mixture was allowed to warm to RT and was stirred 2 hours. Then 100 ml $H_2O$ was added and the mixture concentrated under reduced pressure to about 150 ml whereupon it was diluted with 300 ml ether. The organic layer was washed with water and brine and was dried over sodium sulfate. Removal of the solvent gave an oil which was purified by chromatography on silica (hexane-ethyl acetate 4:1) to afford compound (45) (3.55 g, 35%). $^1$HNMR ($CDCl_3$; 300 MHz) δ: 1.02 (9H, s, 3'-OSitBu); 1.80 (3H, s, Me-5); 4.62 (2H, s, Ph-$Ch_2$-O); 5.5 (1H, m, H-5'); 6.32 (1H, dd, J=6.0 Hz, H-1'); 6.95 (1H, s, H-8).

D. Compound (46), Structure (IV) wherein $R_{E1}$ is hydroxymethyl, $R_{E2}$ is O-(t-butyldiphenylsilyl), and $R_{E3}$ is $CH_2OCH_2Ph$.

To a stirred solution of compound (45) (252 mg, 0.42 mmol) in 5 ml of dry THF, cooled to 0° C. under an argon atmosphere, was added 0.25 ml (2.5 mmol) of 10M borane dimethyl sulphide complex in THF. After 2 hours at 0° C., the mixture was quenched by the slow continuous concurrent addition of 4 ml of 2N aqueous NaOH solution and 1 ml of 30% aqueous $H_2O_2$ solution. The reaction mixture was allowed to warm to room temperature for 10 minutes, diluted with 50 ml of $CH_2Cl_2$, and washed with $H_2O$ and brine. After being dried ($MgSO_4$), the organic phase was concentrated under reduced pressure. Chromatography of the residue on silica gel (hexane-ethyl acetate, 2:1 to 1:1) afforded compound (46) (186 mg, 72%) as a colorless oil. $^1$H NMR ($CDCl_3$, 300 MHz) δ: 1.01 (9H, s, 3'-OSitBu), 1.80 (3H, s, Me-5), 3.51 (2H, m, $CH_2$-6'), 5.41 (2H, s, O-$CH_2$-N), 6.27 (1H, dd, J=6 HZ, H-1'), 6.87 (1H, S, H-6).

E. Compound (46), Structure (IV) wherein $R_{E1}$ is hydroxymethyl, $R_{E2}$ is O-(t-butydiphenylsilyl), and $R_{E3}$ is H.

A vigorously stirred solution of compound (46) (1.03 g, 1.67 mmol) in 37 ml of MeOH was hydrogenated (atmospheric pressure) at room temperature in the presence of powdered Pd/C 10% (520 mg) for 3 days. The reaction mixture was filtered through a path of silica gel. The solid was washed with MeOH (100 ml). To the filtrate was added KOH (~200 mg, 3.6 mmol), and the resulting solution was stirred for 1 hour at room temperature. The solution was concentrated under reduced pressure to approximately 20 ml and was diluted with $CH_2Cl_2$ (100 ml) and the organic phase was washed with $H_2O$ and brine. After being dried ($MgSO_4$), the solvent was removed under reduced pressure to give compound (47) (742 mg, 90%). This material was used for the next step without further purification. $^1$H NMR ($CDCl_3$-300 MHz) δ: 0.94 (9H,s, 3'-OSitBu), 1.73 (s, 3H, Me-5), 3.45 (2H, m, $CH_2$-6'), 6.17 (1H, dd, J=6.5 Hz, H-1'), 6.85 (1H, s, H6).

F. Compound (48), Structure (IV) wherein $R_{E1}$ is C(O)OH, $R_{E2}$ is O-(t-butyldiphenylsilyl), and $R_{E3}$ is H.

To a vigorously stirred solution of compound (47) (710 mg, 1.5 mmol) in 5 ml of dry DMF at room temperature under argon was added the pyridinium dichromate (PDC) (1.5 g, 4 mmol). After 14 hours the brown solution was diluted with 35 ml of EtOAc and stirred 5 min. The suspension was filtered through a path of silica gel and the solid was washed with 75 ml of EtOAc. Removal of the solvents and chromatography of the residue on silica gel (ethyl acetate-methanol 95:5) afforded acid (48). $^1$H NMR ($CDCl_3$, 300 MHz) δ: 1.09 (9H,s, 3'-O-SitBu), 1.83 (3H, s, Me-5), 2.38 (2H, m, $CH_2$-5'), 6.32 (1H, dd, J=6.5 Hz, H-1'), 7.23 (1H, s, H-6).

EXAMPLE 27

Synthesis of (50), Structure (IV) wherein $R_{E1}$ is C(O)$CH_3$, $R_{E2}$ is O-t-butyldiphenylsilyl, and $R_{E3}$ is $CH_2OCH_2Ph$.

A. Compound (49), Structures (IV) wherein $R_{E1}$ is (1,3-dithian-2-yl), $R_{E2}$ is O-(t-butyldiphenylsilyl), and $R_{E3}$ is $CH_2OCH_2Ph$.

To a stirred solution of oxalyl chloride (2.2 ml, 25 mmol) in 45 ml of dry $CH_2Cl_2$ at −78° C. under argon was added a solution of dry DMSO (3.6 ml, 50 mmol) in 15 ml of $CH_2Cl_2$ over 5 minutes. After stirring for 1 hour at −78° C., a solution of compound (32) (10 g, 10.64 mmol) in 50 ml of $CH_2Cl_2$ was added over 20 minutes. After 45 minutes at −78° C., dry triethylamine (14.8 ml, 0.1 mol) was added over 5 minutes and the reaction mixture was allowed to warm to −30° C. over 1 hour. To the latter solution at −78° C. was added a solution of phosphonium ylide [prepared by addition of 0.5N potassium his (trimethylsilyl) amide in toluene (85 ml, 42.2 mmol) to a stirred slurry solution of 1,3-dithian-2-yl-triphenylphosphonium chloride (16 g, 38.4 mmol) in 135 ml of dry THF at −78° C., followed by stirring at room temperature for 3 hours]. The resulting mixture was allowed to warm to room temperature and was stirred 2 hours. Then, 300 ml of $CH_2Cl_2$ and 100 ml of $H_2O$ were added. The mixture was stirred 10 minutes and the layers were separated. The aqueous layer was extracted with one 200 ml portion of $CH_2Cl_2$. The combined organic layers were washed with brine, dried over $MgSO_4$, and concentrated under reduced pressure. The residue was purified by chromatography on silica gel (hexane-EtOAc) to give compound (49) (10.1 g, 7%), MS(FD; m/e): 701 ($M^+$).

B. Compound (50), Structure (IV) wherein $R_{E1}$ is $C(O)OCH_3$, $R_{E2}$ is O-(t-butydiphenylsily), and $R_{E3}$ is $CH_2OCH_2Ph$.

To a stirred solution of (49) (1.3 g, 1.85 mmol) in $MeOH:H_2O$ (9:1; 50 ml) at reflux under argon was added mercuric chloride (2.9 g, 10.7 mmol). After 40 minutes, the reaction mixture was cooled to room temperature, the salts were filtered, the mother liquor was concentrated under reduced pressure, and the residue was diluted with 100 ml of $CH_2Cl_2$. The organic layer was washed with two 30 ml portions of $H_2O$ and one portion of brine. After drying over $MgSO_4$, the solvent was removed and the residue was purified by chromatography on silica gel (hexane-ethyl acetate, 7:3) to afford compound (50). $^1H$ NMR ($CDCl_3$,300 MHz) δ: 1.02 (9H, s, 3'-OSitBu), 1.80 (3H, s, Me-5), 2.28 (2H, m, $CH_2$-5'), 3.52 (3H, s, MeO), 5.41 (2H, s. O-$CH_2$-N), 6.29 (1H, dd, J=6.5 Hz, H-1'), 7.03 (1H, H-6).

EVALUATION

PROCEDURE 1—Hybridization Analysis

The relative ability of an oligonucleotide, an oligonucleotide analog or oligonucleoside of the invention to bind to complementary nucleic acids can be compared by determining the melting temperature of a particular hybridization complex. The melting temperature ($T_m$), a characteristic physical property of double standard RNA, denotes the temperature in degrees centigrade at which 50% helical versus coil (unhybridized) forms are present. $T_m$ is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the $T_m$, the greater the strength of the binding of the strands. Non-Watson-Crick base pairing has a strong destabilizing effect on the $T_m$. Consequently, absolute fidelity of base pairing is necessary to have optimal binding of an antisense oligonucleotide or oligonucleoside to its targeted RNA.

A. Evaluation of the thermodynamics of hybridization of oligonucleotide analogs.

The ability of the oligonucleotide analogs of the invention to hybridize to their complementary RNA or DNA sequences can be determined by thermal melting analysis. The RNA complement is synthesized from T7 RNA polymerase and a template-promoter of DNA synthesized with an Applied Biosystems, Inc. 380B nucleic acid synthesizer. The RNA species is purified by ion exchange using FPLC (LKB Pharmacia, Inc.). Antisense oligonucleotide analogs are added to either the RNA or DNA complement at stoichiometric concentrations and the absorbance (260 nm) hyperchromicity upon duplex to random coil transition monitored using a Gilford Response II spectrophotometer. These measurements are performed in a buffer of 10 mM Na-phosphate, pH 7.4, 0.1 mM EDTA, and NaCl to yield an ionic strength of either 0.1M or 1.0M. Data can be analyzed by a graphic representation of $1/T_m$ vs ln[Ct], where [Ct] is the total oligonucleotide concentration.

The thermodynamic parameters are determined from this analysis. Based upon the information gained concerning the stability of the duplex of hetero-duplex formed, the placement of modified linkages into oligonucleotide analogs is assessed for their effects on helix stability. Modifications that drastically alter the stability of the hybrid exhibit reductions in the free energy (delta G) and decisions concerning their usefulness as antisense oligonucleotides are made.

B. Fidelity of hybridization of oligonucleotide analogs

The ability of the antisense oligonucleotide analogs of the invention to hybridize with absolute specificity to a targeted mRNA can be shown by Northern blot analysis of purified target mRNA in the presence of total cellular RNA. Target mRNA is synthesized from a vector containing the cDNA for the target mRNA located downstream from a T7 RNA polymerase promoter. Synthesized mRNA is electrophoresed in an agarose gel and transferred to a suitable support membrane (e.g., nitrocellulose). The support membrane is blocked and probed using [$^{32}P$]-labeled oligonucleotide analogs. The stringency is determined by replicate blots and washing in either elevated temperatures or decreased ionic strength of the wash buffer. Autoradiography is performed to assess the presence of heteroduplex formation and the autoradiogram quantitated by laser densitometry (LKB Pharmacia, Inc.). The specificity of hybrid formation is determined by isolation of total cellular RNA by standard techniques and its analysis by agarose electrophoresis, membrane transfer and probing with the labelled oligonucleotide analogs. Stringency is predetermined for an unmodified antisense oligonucleotide and the conditions used such that only the specifically targeted mRNA is capable of forming a heteroduplex with the oligonucleotide analog.

PROCEDURE 2—Nuclease Resistance

A. Evaluation of the resistance of oligonucleotide analogs to serum and cytoplasmic nucleases.

Oligonucleotide analogs of the invention can be assessed for their resistance to serum nucleases by incubation of the oligonucleotide analog in media containing various concentrations of fetal calf serum or adult human serum. Labeled oligonucleotide analogs are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the oligonucleotide, it is possible to determine the effect on nuclease degradation by the particular modification. For the cytoplasmic nucleases, an HL 60 cell line can be used. A post-mitochondrial supernatant is prepared by differential centrifugation and the labelled oligonucleotide analogs are incubated in this supernatant for various times. Following the incubation, the oligonucleotide analogs are assessed for degradation as outlined above for serum nucleolytic degradation. Autoradiography results are quantitated for comparison of the unmodified and the oligonucleotide analogs of the invention.

B. Evaluation of the resistance of oligonucleotide analogs to specific endo- and exo-nucleases.

Evaluation of the resistance of natural oligonucleotides and oligonucleotide analogs of the invention to specific nucleases (i.e., endonucleases, 3',5'-exo-, and 5',3'-exonucleases) can be done to determine the exact effect of the modified linkage on degradation. The oligonucleotide analogs are incubated in defined reaction buffers specific for various selected nucleases. Following treatment of the products with protease K, urea is added and analysis on 20% polyacrylamide gels containing urea is performed. Gel products are visualized by staining with Stains All reagent (Sigma Chemical Co.). Laser densitometry is used to quantitate the extent of degradation. The effects of the modified linkage are determined for specific nucleases and compared with the results obtained from the serum and cytoplasmic systems.

PROCEDURE 3—5-Lipoxygenase Analysis, Therapeutics and Assays

A. Therapeutics

For therapeutic use, an animal suspected of having a disease characterized by excessive or abnormal supply of 5-lipoxygenase is treated by administering oligonucleotide analogs in accordance with this invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleoide analogs of this invention will also be useful as research reagents when used to cleave or otherwise modulate 5-lipoxygenase. mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 mg of total RNA in a buffer consisting, for example, of 50 mM phosphate, pH ranging from about 4–10 at a temperature from about 30° to about 50° C. The cleaved 5-lipoxygenase RNA can be analyzed by agarose gel electrophoresis and hybridization with radiolabeled DNA probes or by other standard methods.

C. Diagnostics

The oligonucleotide analogs of this invention will also be useful in diagnostic applications, particularly for the determination of the expression of specific mRNA species in various tissues or the expression of abnormal or mutant RNA species. In this example, the oligonucleotide analogs target a hypothetical abnormal mRNA by being designed complementary to the abnormal sequence, but would not hybridize to or cleave the normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved by the invention compound, would not be bound to the support and therefore would be separated from the normal mRNA.

Targeted mRNA species for modulation relates to 5-lipoxygenase. However, persons of ordinary skill in the art will appreciate that the present invention is not so limited and that it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of antisense oligonucleotides analogs which interfere with 5-lipoxygenase synthesis in these cells.

A second test system for antisense oligonucleotides makes use of the fact that 5-lipoxygenase is a "suicide" enzyme in that it inactivates itself upon reacting with substrate. Treatment of differentiated HL-60 or other cells expressing 5 lipoxygenase, with 10 µM A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. The cells take approximately 24 hours to recover from A23187 treatment as measured by their ability to synthesize leukotriene $B_4$. Oligonucleotide analogs directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

The most direct effect which oligonucleotide analogs can exert on intact cells and which can be easily be quantitated is specific inhibition of 5-lipoxygenase protein synthesis. To perform this technique, cells can be labelled with $^{35}$S-methionine (50 µCi/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 µM, 10 µM, and 30 µM of effective oligonucleotide analogs for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 µM $^{14}$C-arachidonic acid, 2mM ATP, 50 µM free calcium, 100 µg/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective oligonucleotide analogs at 1 µM, 10 µM, and 30 µM would be as follows. Control cells oxidize 200 pmol arachidonic acid/5 min/10$^6$ cells. Cells treated with 1 µM, 10 µM, and 30 µM of an-effective oligonucleotide analogs would oxidize 195 pmol, 140 pmol, and 60 pmol of arachidonic acid/5 min/10$^6$ cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. A 25 ng portion of purified 5-lipoxygenase is bound to the microtiter plates overnight at 4° C. The wells are blocked for 90 min with 5% goat serum diluted in 20 mM Tris® HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 µL in the microtiter wells for 90 min. The antibodies are prepared by immunizing rabbits with purified human recombinant 5-lipoxygenase. The wells are washed with TBS containing 0.05% tween 20 (TBST), then incubated with 100 µL of a 1:1000 dilution of peroxidase conjugated goat anti-rabbit IgG (Cappel Laboratories, Malvern, Pa.) for 60 min at 25° C. The wells are washed with TBST and the amount of peroxidase labelled second antibody determined by development with tetramethylbenzidine.

Predicted results from such an assay using a 30 mer oligonucleotide analog at 1 µM, 10 µM, and 30 µM would be 30 ng, 18 ng and 5 ng of 5-lipoxygenase per 10$^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells (2×10$^5$ cells/mL) will be treated with increasing concentrations of oligonucleotide analogs for 48–72 hours in the presence of 1.3% DMSO. The cells are washed and resuspended at a concentration of 2×10$^6$ cell/mL in Dulbecco's phosphate buffered saline containing 1% delipidated bovine serum albumin. Cells are stimulated with 10 µM calcium ionophore A23187 for 15 min and the quantity of LTB4 produced from 5×10$^5$ cell determined by radioimmunoassay as described by the manufacturer.

Using this assay the following results would likely be obtained with a 15-mer modified linkage bearing antisense oligonucleotide (GCAAGGTCACTGAAG) directed to the 5-LO mRNA. Cells will be treated for 72 hours with either 1 µM, 10 µM or 30 µM oligonuclotide analog in the presence of 1.3% DMSO. The quantity of LTB$_4$ produced from 5×10$^5$ cells would be expected to be about 75 pg, 50 pg, and 35 pg, respectively with untreated differentiated cells producing 75 pg LTB$_4$.

E. In Vivo Assay

Inhibition of the production of 5-lipoxygenase in the mouse can be demonstrated in accordance with the following protocol. Topical application of arachidonic acid results in the rapid production of leukotriene B$_4$, leukotriene C$_4$ and prostaglandin E$_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene B$_4$ produced in biopsy specimens is performed as a direct measurement of 5-lipoxygenase activity in the tissue. Oligonucleotide analogs will be applied topically to both ears 12 to 24 hours prior to administration of arachidonic acid to allow optimal activity of the compounds. Both ears are pretreated for 24 hours with either 0.1 µmol, 0.3 µmol, or 1.0 µmol of the oligonucleotide analog prior to challenge with arachidonic acid. Values are expressed as the mean for three animals per concentration. Inhibition of polymorphonuclear cell infiltration for 0.1 µmol, 0.3 µmol, and 1 µmol is expected to be about 10%, 75% and 92% of control activity, respectively. Inhibition of edema is expected to be about 3%, 58% and 90%, respectively while inhibition of leukotriene B$_4$ production would be expected to be about 15%, 79% and 99%, respectively.

What is claimed is:

1. An oligonucleotide analog comprising the structure:

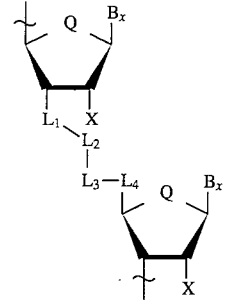

wherein:

$B_x$ is a variable base moiety;

Q is O, $CH_2$, CHF or $CF_2$;

X is H; OH; $C_1$ to $C_{10}$ lower alkyl, substituted lower alkyl, alkaryl or aralkyl; F; Cl; Br; CN; $CF_3$; $OCF_3$; OCN;

O—, S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; or substituted silyl;

L$_1$—L$_2$—L$_3$—L$_4$ is selected from NR—C(O)—CH$_2$—CH$_2$—, NR—C(S)—CH$_2$—CH$_2$, CH$_2$—NR—C(O)—CH$_2$, CH$_2$—NR—C(S)—CH$_2$, CH$_2$—CH$_2$—NR—C(O), CH$_2$—CH$_2$—NR—C(S), C(O)—NR—CH$_2$—CH$_2$, C(S)—NR—CH$_2$—CH$_2$, CH$_2$—C(O)—NR—CH$_2$, and CH$_2$—C(S)—NR—CH$_2$ where R is hydrogen, alkyl, substituted alkyl, aralkyl, alkenyl, alkaryl, aminoalkyl, hydroxyalkyl, heterocycloalkyl, or heterocycloaralkyl; and the remaining subunits are natural or synthetic.

2. The oligonucleotide analog of claim 1 wherein Q is 0.
3. The oligonucleotide analog of claim 1 wherein X is H.
4. The oligonucleotide analog of claim 1 wherein X is OH.
5. The oligonucleotide analog of claim 1 wherein X is H, OH, F, O-alkyl or O-alkenyl and Q is 0.
6. The oligonucleotide analog of claim 1 wherein B$_x$ is adenine, guanine, uracil, thymine, cytosine, 2-aminoadenosine or 5-methylcytosine.
7. The oligonucleotide analog of claim 1 comprising from about 4 to about 50 subunits having said structure.
8. The oligonucleotide analog of claim 1 wherein substantially all of the subunits have said structure.
9. The oligonucleotide analog of claim 1 wherein substantially alternating subunits have said structure.
10. A compound having the structure:

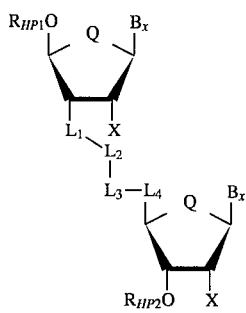

wherein:

B$_x$ is a variable base moiety;

Q is 0, CH$_2$, CHF or CF$_2$;

X is H; OH; C$_1$ to C$_{10}$ lower alkyl, substituted lower alkyl, alkaryl or aralkyl; F; Cl; Br; CN; CF$_3$; OCF$_3$; OCN; O—, S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; or aminoalkylamino; polyalkylamino; substituted silyl;

L$_1$—L$_2$—L$_3$—L$_4$ is selected from NR—C(O)—CH$_2$—CH$_2$, NR—C(S)—CH$_2$—CH$_2$, CH$_2$—NR—C(O)—CH$_2$, CH$_2$—NR—C(S)—CH$_2$, CH$_2$—CH$_2$—NR—C(O), CH$_2$—CH$_2$—NR—C(S), C(O)—NR—CH$_2$—CH$_2$, C(S)—NR—CH$_2$—CH$_2$, CH$_2$—C(O)—NR—CH$_2$, and CH$_2$—C(S)—NR—CH$_2$ where R is hydrogen, alkyl, substituted alkyl, aralkyl, alkenyl, alkaryl, aminoalkyl, hydroxyalkyl, heterocycloalkyl, or heterocycloaralkyl; and R$_{HP1}$ and R$_{HP2}$ are, independently, H or a hydroxyl protecting group.

11. The compound of claim 10 wherein Q is 0.
12. The compound of claim 10 wherein X is H.
13. The compound of claim 10 wherein X is OH.
14. The compound of claim 10 wherein X is H, OH, F, O-alkyl or O-alkenyl and Q is 0.
15. The compound claim 10 wherein B$_x$ is adenine, guanine, uracil, thymine, cytosine, 2-aminoadenosine or 5-methylcytosine.
16. A process for preparing a compound having the structure:

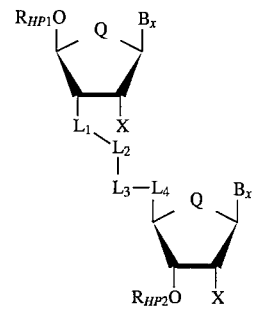

wherein:

B$_x$ is a variable base moiety;

Q is 0, CH$_2$, CHF or CF$_2$;

X is H; OH; C$_1$ to C$_{10}$ lower alkyl, substituted lower alkyl, alkaryl or aralkyl; F; Cl; Br; CN; CF$_3$; OCF$_3$; OCN; O—, S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; or substituted silyl;

L$_1$—L$_2$—L$_3$—L$_4$ is selected from NR—C(O)—CH$_2$—CH$_2$, NR—C(S)—CH$_2$—CH$_2$, CH$_2$—NR—C(O)—CH$_2$, CH$_2$—NR—C(S)—CH$_2$, CH$_2$—CH$_2$—NR—C(O), CH$_2$—CH$_2$—NR—C(S), C(O)—NR—CH$_2$—CH$_2$, C(S)—NR—CH$_2$—CH$_2$, CH$_2$—C(O)—NR—CH$_2$, and CH$_2$—C(S)—NR—CH$_2$ where R is hydrogen, alkyl, substituted alkyl, aralkyl, alkenyl, alkaryl, aminoalkyl, hydroxyalkyl, heterocycloalkyl, or heterocycloaralkyl; and R$_{HP1}$ and R$_{HP2}$ are, independently, H or a hydroxyl protecting group.

comprising the steps of:

providing a first synthon having structure (I) and second synthon having structure (II):

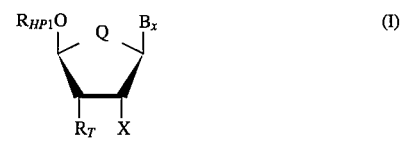

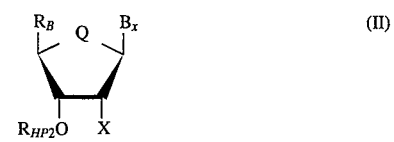

wherein:

(a) R$_T$ is NH$_2$ and R$_B$ is R$_A$—CH$_2$—CH$_2$;
(b) R$_T$ is CH$_2$—NH$_2$ and R$_B$ is R$_A$—CH$_2$;
(c) R$_T$ is CH$_2$—CH$_2$—NH$_2$ and R$_B$ is R$_A$;
(d) R$_T$ is R$_A$ and R$_B$ is NH$_2$—CH$_2$—CH$_2$; or (e) $R_T$ is $CH_2$—$R_A$ and $R_B$ is $NH_2$—$CH_2$;

where $R_A$ is C(O) OH, C(S)OH, or an activated derivative thereof; and coupling said first synthon and said second synthon to form an amide or thioamide linkage through said $R_T$ and $R_B$ groups.

17. The oligonucleotide analog of claim 1 wherein $L_1$—$L_2$—$L_3$—$L_4$ is $CH_2$—NR—C(O)—$CH_2$.

18. The oligonucleotide analog of claim 1 wherein $L_1$—$L_2$—$L_3$—$L_4$ is $CH_2$—C(O)—NR—$CH_2$.

19. The compound of claim 10 wherein $L_1$—$L_2$—$L_3$—$L_4$ is $CH_2$—NR—C(O)—$CH_2$.

20. The compound of claim 10 wherein $L_1$—$L_2$—$L_3$—$L_4$ is $CH_2$—C(O)—NR—$CH_2$.

* * * * *